United States Patent
Cronin et al.

(10) Patent No.: US 7,846,659 B2
(45) Date of Patent: *Dec. 7, 2010

(54) ARRAYS OF NUCLEIC ACID PROBES FOR ANALYZING BIOTRANSFORMATION GENES

(75) Inventors: Maureen T. Cronin, Los Altos, CA (US); Charles G Miyada, San Jose, CA (US); Earl A. Hubbell, Los Angeles, CA (US); Mark Chee, Palo Alto, CA (US); Stephen P. A. Fodor, Palo Alto, CA (US); Xiaohua C. Huang, Mountain View, CA (US); Robert J. Lipshutz, Palo Alto, CA (US); Peter E. Lobban, Mountain View, CA (US); MacDonald S. Morris, Felton, CA (US); Edward L. Sheldon, San Diego, CA (US)

(73) Assignee: Affymetrix, Inc., Santa Clara, CA (US)

( * ) Notice: Subject to any disclaimer, the term of this patent is extended or adjusted under 35 U.S.C. 154(b) by 791 days.

This patent is subject to a terminal disclaimer.

(21) Appl. No.: 11/401,482

(22) Filed: Apr. 11, 2006

(65) Prior Publication Data

US 2007/0054286 A1    Mar. 8, 2007

Related U.S. Application Data

(63) Continuation of application No. 11/367,800, filed on Mar. 3, 2006, now abandoned, which is a continuation of application No. 09/798,260, filed on May 1, 2002, now abandoned, which is a continuation of application No. 08/778,794, filed on Jan. 3, 1997, now Pat. No. 6,309,823, which is a continuation-in-part of application No. 08/544,381, filed on Oct. 10, 1995, now Pat. No. 6,027,880, which is a continuation-in-part of application No. 08/510,521, filed on Aug. 2, 1995, now Pat. No. 7,115,364, which is a continuation-in-part of application No. PCT/US94/12305, filed on Oct. 26, 1994, which is a continuation-in-part of application No. 08/284,064, filed on Aug. 2, 1994, now abandoned, which is a continuation-in-part of application No. 08/143,312, filed on Oct. 26, 1993, now abandoned.

(51) Int. Cl.
| C12Q 1/68 | (2006.01) |
| C12P 19/34 | (2006.01) |
| C07H 21/02 | (2006.01) |
| C07H 21/04 | (2006.01) |

(52) U.S. Cl. .......................... 435/6; 536/23.1; 536/24.3; 536/24.33

(58) Field of Classification Search .................. None
See application file for complete search history.

(56) References Cited

U.S. PATENT DOCUMENTS 4,656,127 A    4/1987    Mundy
4,683,195 A    7/1987    Mullis et al.
5,002,867 A    3/1991    Macevicz
5,143,854 A    9/1992    Pirrung et al.
5,202,231 A    4/1993    Drmanac et al.
5,273,632 A    12/1993   Stockham et al.
5,281,540 A    1/1994    Merkh et al.
5,314,829 A    5/1994    Coles
5,404,523 A    4/1995    DellaFera et al.
5,472,842 A    12/1995   Stokke et al.
5,527,681 A    6/1996    Holmes
5,620,848 A    4/1997    Levine et al.
5,670,314 A    9/1997    Christman et al.
5,690,894 A    11/1997   Pinkel et al.
5,700,637 A    12/1997   Southern (Continued)

FOREIGN PATENT DOCUMENTS

EP    0463395    1/1992

(Continued)

OTHER PUBLICATIONS

Johansson et al., "Inherited amplification of an active gene in the cytochrome P450 CYP2D locus as a cause of ultrarapid metabolism of debrisoquine," PNAS, USA, Dec. 1993, vol. 90, pp. 11825-11829.*

(Continued)

*Primary Examiner*—Young J Kim
(74) *Attorney, Agent, or Firm*—Sandra E. Wells

(57) ABSTRACT

The invention provides arrays of immobilized probes, and methods employing the arrays, for detecting mutations in the biotransformation genes, such as cytochromes P450. For example, one such array comprises four probe sets. A first probe set comprises a plurality of probes, each probe comprising a segment of at least three nucleotides exactly complementary to a subsequence of a reference sequence from a biotransformation gene, the segment including at least one interrogation position complementary to a corresponding nucleotide in the reference sequence. Second, third and fourth probe sets each comprise a corresponding probe for each probe in the first probe set. The probes in the second, third and fourth probe sets are identical to a sequence comprising the corresponding probe from the first probe set or a subsequence of at least three nucleotides thereof that includes the at least one interrogation position, except that the at least one interrogation position is occupied by a different nucleotide in each of the four corresponding probes from the four probe sets.

16 Claims, 22 Drawing Sheets

U.S. PATENT DOCUMENTS

| | | | |
|---|---|---|---|
| 5,812,793 | A | 9/1998 | Shakib et al. |
| 5,837,454 | A | 11/1998 | Cozzette et al. |
| 5,837,832 | A * | 11/1998 | Chee et al. .................... 506/16 |
| 5,861,242 | A * | 1/1999 | Chee et al. ...................... 506/3 |
| 6,027,880 | A * | 2/2000 | Cronin et al. ................... 435/6 |
| 6,090,566 | A | 7/2000 | Vogelstein et al. |
| 6,215,894 | B1 | 4/2001 | Zeleny et al. |
| 6,309,823 | B1 * | 10/2001 | Cronin et al. ................... 435/6 |
| 6,406,849 | B1 | 6/2002 | Dorsel et al. |
| 6,468,744 | B1 * | 10/2002 | Cronin et al. ................... 435/6 |
| 6,470,277 | B1 | 10/2002 | Chin et al. |
| 6,879,915 | B2 | 4/2005 | Cattell |
| 7,115,364 | B1 * | 10/2006 | Chee et al. ..................... 435/6 |
| 2002/0055102 | A1 | 5/2002 | Stern |
| 2002/0086319 | A1 | 7/2002 | Ellson et al. |
| 2002/0168639 | A1 | 11/2002 | Muraca |
| 2002/0177135 | A1 | 11/2002 | Doung |
| 2003/0165823 | A1 | 9/2003 | Cronin et al. |
| 2003/0165830 | A1 | 9/2003 | Cronin et al. |

FOREIGN PATENT DOCUMENTS

| | | |
|---|---|---|
| EP | 0512342 | 11/1992 |
| GB | 2319838 | 6/1998 |
| WO | 89/10977 | 11/1989 |
| WO | 89/11548 | 11/1989 |
| WO | 90/00626 | 1/1990 |
| WO | 90/03382 | 4/1990 |
| WO | 91/10745 | 7/1991 |
| WO | 92/10092 | 6/1992 |
| WO | 92/10588 | 6/1992 |
| WO | 93/17126 | 9/1993 |
| WO | 94/03638 | 2/1994 |
| WO | 94/05394 | 3/1994 |
| WO | 95/00530 | 1/1995 |
| WO | 95/11995 | 5/1995 |
| WO | 95/26973 | 10/1995 |
| WO | 95/33846 | 12/1995 |
| WO | 96/18903 | 6/1996 |

OTHER PUBLICATIONS

Chee et al., "Accessing Genetic Information with High-Density DNA Arrays", Science, 274:610-614 (1996).
Lipshutz et al., "Using Oligonucleotide Probe Arrays to Access Genetic Diversity", Biotechniques 19(3):442-447 (1995).
Chee et al., "Towards Sequencing Mitochondrial DNA Polymorphisms by Hybridization to a Custom Oligonucleotide Probe Array", American Society of Human Genetics, 43rd Annual Meeting, Oct. 5-9, 1993, abstract.
Chee et al., "Genetic Analysis by Hybridization to Sequence-Specific DNA Arrays", American Society of Human Genetics, 43rd Annual Meeting, Oct. 5-9, 1993, Abstract.
Chee et al., "A New Method for Rapid Sequence Analysis: Detection of HIV Reverse Transcriptase Mutations", HIV Drug Resistance Third International Workshop, Aug. 2-5, 1994, Abstract.
Chee et al., "Sequence Analysis by Hybridization: the Human Mitochondrial Genome on a Chip," poster and slide presentation, Genome Sequencing and Analysis Conference V, Sep. 17-21, 1994, Hilton Head, SC (Abstract).
Chee et al., "Sequencing Mitochondrial DNA Polymorphisms by Hybridization", American Society of Human Genetics, 44th Annual Meeting, Oct. 18-22, 1994, Abstract.
Chee, "Resequencing DNA by Hybridization to Olignucleotide Arrays", Western Biotech Conference, Oct. 18-21, 1995, Abstract.
Cronin et al., "Hybridization to Arrays of Olignucleotides," poster, Nucleic Acids in Medical Applications Conference sponsored by ACC, Jan. 1993, Abstract.
Cronin et al., "Detection of Cystic Fibrosis Gene Mutations by Hybridization to GeneChip™ Probe Arrays," poster, Nucleic Acids in Medical Applications Conference sponsored by ACC, Nov. 1993.
Cronin et al., "GeneChip™ Screening Assay for Cystic Fibrosis Mutations", American Society of Human Genetics Meeting, Oct. 1994, Abstract.
Cronin et al., "Detecting Cystic Fibrosis Mutations by Hybridization to DNA Probe Arrays," slide presentation, UCSF School of Medicine Symposium: Molecular Approaches to Laboratory Diagnosis, Feb. 1995, Abstract.
Elder, "Analysis of DNA Oligonucleotide Hybridization Data by Maximum Entropy," Maximum Entropy and Bayesian Methods, pp. 1-10 (1995).
Hagstrom et al., "Maximum Likelihood Genetic Sequence Reconstruction form Oligo Content", Argonne Nat'l Laboratory Prepring MSC-P309-0592, (1992).
Lipshutz, "Likelihood DNA Sequencing by Hybridization," J. Biomol. Struct. Dyn., 11:637-653 (1993).
Lipshutz, "Olignucleotide Arrays for Hybridization Analysis," poster, Genome Sequencing and Analysis Conference V, Oct. 23-27, 1993, Abstract.
Lobban et al., "DNA Chips for Genetic Analysis", Genome Sequencing and Analysis Conference V, Oct. 23-27, 1993, Abstract.
Lockhart et al., "DNA Sequencing by Hybridization on High Density Probe Arrays: Enzymatic Enhancement and Sequence Reconstruction", American Society of Human Genetics 44th Annual Meeting, Oct. 18-22, 1994.
Luo et al., "Cellular Protein Modulates Effects of Human Immunodeficiency Virus Type 1 Rev," J. Virol. 69:3850-3856 (1994).
Maxam et al., "A New Method for Sequencing DNA," Proc. Natl. Acad. Sci. USA, 74:560-564 (1977).
Maxam et al., "Sequencing End-Labeled DNA with Base-Specific Chemical Cleavages," Methods in Enzymology, 65:499-560 (1980).
Miyada et al., "Detection of Cystic Fibrosis Mutations in a GeneChip™. Assay Format", Amer. Society of Human Genetics 44th Annual Meeting, Oct. 1994, abstract.
Querat et al., "Nucleotide Sequence Analysis of SA-OMVV, a Visna-Related Ovine Lentivirus: Phylogenetic History of Lentiviruses," Virology, 175:434-447 (1990).
Ratner et al., "Complete Nucleotide Sequence of the AIDS Virus, HLTV-III," Nature, 313:277-284 (1985).
Sambrook et al., "Molecular Cloning," Cold Spring Harbor Press, pp. 1145-1147 (1989).
Sanger et al., "DNA Sequencing with Chain-Terminating Inhibitors," Proc. Natl. Acad. Sci. USA, 74:5463-5467 (1977).
Southern et al., "Analyzing and Comparing Nucleic Acid Sequences by Hybridization to Arrays of Oligonucleotides: Evaluation Using Experimental Models," Genomics, 13:1008-1017 (1992).
Stratagene 1988 Catalog, "Gene Characterization Kits," p. 39.
Wain-Hobson et al., "Nucleotide Sequence of the AIDS Virus, LAV," Cell, 40:9-17 (1985).
Cocco et al., "Lack of Evidence for a Role of the Myelin Basic Protein Gene in Multiple Sclerosis Susceptibility in Sardinian Patients", J. Neurology, 24(11):1552-1555 (2002).
Cronin et al., "cystic Fibrosis Mutation Detection by Hybridization to Light-Generated DNA Probe Array", Human Mutation, 7(3):244-255 (1996).
Finch et al., "PCR/RFLP Assay for Copy Number of Mutant and Wild-Type Alleles", BioTechiques, 21:1055-1060 (1996).
Gonzales et al., "Pharmacogenetic Phenotyping and Genotyping, Present Status and Future Potential", Clin. Pharmacokinet, 26(1):59-70 (1994).
Hacia et al., "Detection of Heterozygous Mutations in BRCA1 Using High Density Oligonucleotide Arrays and Two-Colour Fluorescence Analysis", Nature Genetics, 14:441-447 (1996).
Laan et al., "solid-Phase Minisequencing Confirmed by FISH Analysis in Determination of Gene Copy Number", Human Genetics, 96:275-280 (1995).
Rudert et al., "Rapid Detection of Sequence Variations Using Polymers for Specific Oligonucleoties", Nuc. Acids Res., 20(5):1146 (1992).

Stickland et al., "Quantification of Oncogene Dosage in Tumors by Simultaneous Dual Label Hydridization", Oncogene, 8:223-227 (1993).

Strachan et al., Human Molecular Genetics, pp. 466-471, Bios Scientific Publishers Limited, Oxford OX4 1RE, UK (1996).

Takeda et al., "An Increased NM23H1 Copy Number May be a Poor Prognostic Factor Independent of LOH on 1p in Neuroblastomas", Br. J. Cancer, 74:1620-1626 (1996).

Tully et al., "Analysis of 6 VNTR Loci by Multiplex PCR and Automated Florescent Detection", Human Genetics, 92:554-562 (1993).

Cronin et al., Abstract: Comparison of CY2D6 Genotyping by Oligonucleotide Array Hybridization and a PCR Based Method, International Society for the Study of Xenobiotics Meeting, Oct. 24-26, 1996.

Lin et al. Abstract: A Method for Genotyping CYP2D6 and CYP2C19 Genotyping Using Oligonucleptide Array Hybridization, International Society for the Study of Xenobiotics Meeting, Oct. 24-26, 1996.

* cited by examiner

Position
Reference    5'...A A A G A A A A A G A C A G T A C T A A T G G A....

Position n   3'         t t t t t t A t g t c a t ⎤
Probe Set    3'         t t t t t t G t g t c a t ⎬ Probe Sets A, B & C
             3'         t t t t t t T t g t c a t ⎦
                                    └─ Interrogation Position
                                       Corresponding to n n+1          3'           t t t t t c A g t c a t g ⎤
             3'           t t t t t c C g t c a t g ⎬ Probe Sets A, B & C
             3'           t t t t t c G g t c a t g ⎦
                                      └─ Interrogation Position
                                         Corresponding to n+1 n+2          3'             t t t t c t A t c a t g a ⎤
             3'             t t t t c t C t c a t g a ⎬ Probe Sets A, B & C
             3'             t t t t c t T t c a t g a ⎦
                                        └─ Interrogation Position
                                           Corresponding to n+2

FIG. 3B

```
                ACTGTTAGCTAATTGG  Ref. Seq.

A-lane    TG[A]C  GA[A]A  AC[A]A  CA[A]T  AA[A]C
C-lane    TG[C]C  GA[C]A  AC[C]A  CA[C]T  AA[C]C
G-lane    TG[G]C  GA[G]A  AC[G]A  CA[G]T  AA[G]C
T-lane    TG[T]C  GA[T]A  AC[T]A  CA[T]T  AA[T]A
           |I₁     |I₂     |I₃     |I₄     |I₅
wt. lane  TG[A]C  GA[C]A  -AC[A]A  CA[A]T  AA[T]C
```

FIG. 4A

CENTRAL INTERROGATION POSITION
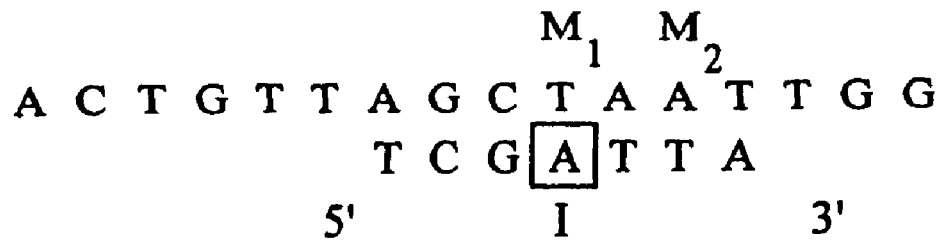
3' INTERROGATION POSITION
5' INTERROGATION POSITION
FIG. 4B

Tiled Array with Probes for the
Detection of Point Mutations

```
                         CORRESPONDING NUCLEOTIDES
        n₁  n₂  n₃
A C T G  T   T  A G  C  T A A T T G ──── REF. SEQ.
      C [A] A [T] C [G] A
         │     │     │       ──── PROBE FROM FIRST SET
         1     2     3   ──── INTERROGATION POSITIONS

C [C] A  T  C  G  A  ⎫ CORRESPONDING PROBES
      C [G] A  T  C  G  A  ⎬ FROM SECOND, THIRD AND
      C [T] A  T  C  G  A  ⎭ FOURTH PROBE SETS
         │
         1

C  A  A [A] C  G  A  ⎫ CORRESPONDING PROBES
      C  A  A [C] C  G  A  ⎬ FROM FIFTH, SIXTH AND
      C  A  A [G] C  G  A  ⎭ SEVENTH PROBE SETS
               │
               2

C  A  A  T  C [A] A  ⎫ CORRESPONDING PROBES
      C  A  A  T  C [C] A  ⎬ FROM EIGHTH, NINTH AND
      C  A  A  T  C [T] A  ⎭ TENTH PROBE SETS
                     │
                     3
```

FIG. 7

```
         n₃    n₄ n₁         n₂
A  C  T  G  T  T  T  A  G  C  T  A  A  T  T  G  G ——— REF. SEQ.
            C  A  A  T  C  C  A  A  T
            C  C  C  T  C  C  C  A  T
            C  A  G  T  C  C  G  A  T
            C  A  T  T  C  C  T  A  T
                  │                │
                  I₁               I₂ ———INTERROGATION POSITIONS

T  G  A  C  T  A  T
T  G  C  C  C  A  T
T  G  G  C  C  A  T
T  G  T  C  A  A  T
      │  │
      I₃ I₄ ———INTERROGATION POSITIONS
```

FIG. 8

```
              n CORRESPONDING NUCLEOTIDE
A  T  T  C  C  C  G  G  G  A  T  C ——— PROBE FROM FIRST PROBE SET
         A  G  G  G  C  C  A  T
         A  G  G  C  C  C  A  T      CORRESPONDING PROBES
         A  G  G  A  C  C  A  T  ┤   FROM SECOND, THIRD AND
         A  G  G  T  C  C  A  T      FOURTH PROBE SETS
                  │
                  │ ——— HELPER MUTATION
                  ——— INTERROGATION POSITIONS
```

CYP2D6 P34S MUTATION DETECTION BLOCK
P34S Heterozygote Hybridization
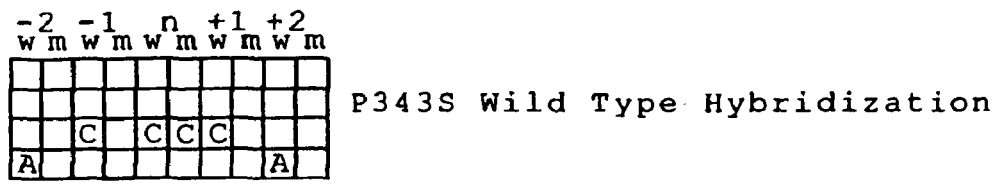
P343S Wild Type Hybridization
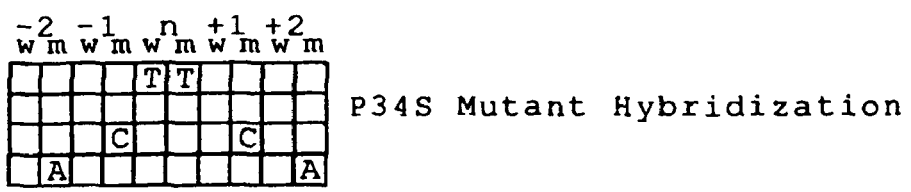
P34S Mutant Hybridization
FIG. 12

DIMERS:
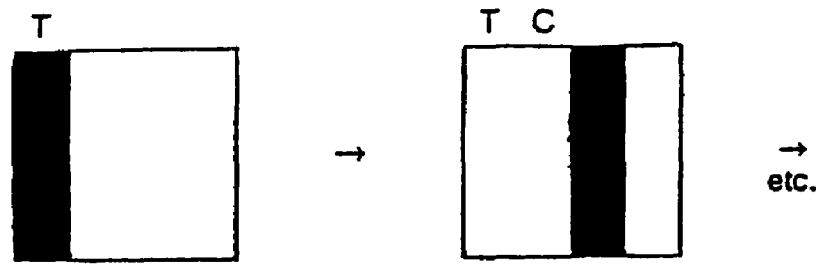
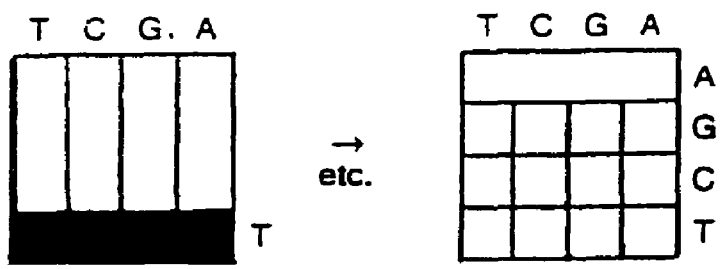
IN POLYNOMIAL NOTATION:
$(T + C + A + G)^2 =$ ALL DIMERS
TRIMERS:
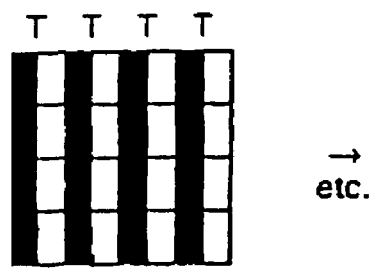
FIG. 17

SEQUENCE LISTING

```
<160> NUMBER OF SEQ ID NOS: 156

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence: Reference
      sequence

<400> SEQUENCE: 1
actgttagct aattgg                                                    16

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 2 gggggggagct aacggg                                                   16

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Probe

<400> SEQUENCE: 3
aaagaaaaaa gacagtacta aatgga                                         26

<210> SEQ ID NO 4
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 4
tactgtattt ttt                                                       13
```

<210> SEQ ID NO 5
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 5
tactgtcttt ttt                                                              13

<210> SEQ ID NO 6
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 6
tactgtgttt ttt                                                              13

<210> SEQ ID NO 7
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 7
tactgttttt ttt                                                              13

<210> SEQ ID NO 8
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 8
gtactgactt ttt                                                              13

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 9
gtactgcctt ttt                                                              13

<210> SEQ ID NO 10
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 10
gtactggctt ttt                                                              13

<210> SEQ ID NO 11
<211> LENGTH: 13
<212> TYPE: DNA
<213> ORGANISM: Artificial Sequence
<220> FEATURE:

```
<223> OTHER INFORMATION: Description of Artificial Sequence: Probe

<400> SEQUENCE: 11
gtactgtctt ttt                                                              13

<210> SEQ ID NO 12
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 12
agtactatct ttt                                                              13

<210> SEQ ID NO 13
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 13
agtactctct ttt                                                              13

<210> SEQ ID NO 14
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 14
agtactgtct ttt                                                              13

<210> SEQ ID NO 15
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 15
agtactttct ttt                                                              13

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Probe

<400> SEQUENCE: 16
aaagaaaaaa gacagtacta atgga                                                 25

<210> SEQ ID NO 17
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 17
ggttaatcga ttgtca                                                           16
```

```
<210> SEQ ID NO 18
<211> LENGTH: 11
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: misc_feature
<222> LOCATION: (1)..(11)
<223> OTHER INFORMATION: N is A, C, G, or T.

<400> SEQUENCE: 18 gggncccctta a                                                              11

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 19
taaagtaaga cataac                                                          16

<210> SEQ ID NO 20
<211> LENGTH: 16
<212> TYPE: DNA
<213> ORGANISM: Artificial Sequence
<220> FEATURE:
<223> OTHER INFORMATION: Description of Artificial Sequence: Probe

<400> SEQUENCE: 20
ggctgacgtc agcaat                                                          16

<210> SEQ ID NO 21
<211> LENGTH: 12
<212> TYPE: DNA
<213> ORGANISM: Artificial Sequence
<220> FEATURE:
<223> OTHER INFORMATION: Description of Artificial Sequence: Reference
      sequence

<400> SEQUENCE: 21
attcccggga tc                                                              12

<210> SEQ ID NO 22
<211> LENGTH: 17
<212> TYPE: DNA
<213> ORGANISM: Artificial Sequence
<220> FEATURE:
<223> OTHER INFORMATION: Description of Artificial Sequence: CYP2D6-B
      target sequence

<400> SEQUENCE: 22
cccccrgacg ccccttt                                                         17

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Target
      sequence

<400> SEQUENCE: 23
taaccactca cgggagca                                                        18
```

```
<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Pool 1
      probes

<400> SEQUENCE: 24
attggmgagt gccc                                                        14

<210> SEQ ID NO 25
<211> LENGTH: 14
<212> TYPE: DNA
<213> ORGANISM: Artificial Sequence
<220> FEATURE:
<223> OTHER INFORMATION: Description of Artificial Sequence: Pool 1
      probes

<400> SEQUENCE: 25
attggagagt gccc                                                        14

<210> SEQ ID NO 26
<211> LENGTH: 14
<212> TYPE: DNA
<213> ORGANISM: Artificial Sequence
<220> FEATURE:
<223> OTHER INFORMATION: Description of Artificial Sequence: Pool 1
      probes

<400> SEQUENCE: 26
attggcgagt gccc                                                        14

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Pool 2
      probe

<400> SEQUENCE: 27
attggkgagt gccc                                                        14

<210> SEQ ID NO 28
<211> LENGTH: 14
<212> TYPE: DNA
<213> ORGANISM: Artificial Sequence
<220> FEATURE:
<223> OTHER INFORMATION: Description of Artificial Sequence: Pool 2
      probe

<400> SEQUENCE: 28 attgggagt gccc                                                         14

<210> SEQ ID NO 29
<211> LENGTH: 14
<212> TYPE: DNA
<213> ORGANISM: Artificial Sequence
<220> FEATURE:
<223> OTHER INFORMATION: Description of Artificial Sequence: Pool 2
      probe

<400> SEQUENCE: 29
attggtgagt gccc                                                        14

<210> SEQ ID NO 30
```

```
<211> LENGTH: 14
<212> TYPE: DNA
<213> ORGANISM: Artificial Sequence
<220> FEATURE:
<223> OTHER INFORMATION: Description of Artificial Sequence: Pool 3
      probe

<400> SEQUENCE: 30
attggrgagt gccc                                                       14

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 31
taacccctca cgggagca                                                   18

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 32
taaccgctca cgggagca                                                   18

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 33
taacctctca cgggagca                                                   18

<210> SEQ ID NO 34
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence

<400> SEQUENCE: 34
nnnnmmnnnn n                                                          11

<210> SEQ ID NO 35
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
```

```
<223> OTHER INFORMATION: N is any nucleotide complementary to the
      reference sequence.

<400> SEQUENCE: 35
nnnnmknnnn n                                                              11

<210> SEQ ID NO 36
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence

<400> SEQUENCE: 36
nnnnmrnnnn n                                                              11

<210> SEQ ID NO 37
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to  the
      reference sequence.

<400> SEQUENCE: 37
nnnnmynnnn n                                                              11

<210> SEQ ID NO 38
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 38
nnnnmwnnnn n                                                              11

<210> SEQ ID NO 39
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 39
nnnnmsnnnn n                                                              11
```

```
<210> SEQ ID NO 40
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 40
nnnnkmnnnn n                                                              11

<210> SEQ ID NO 41
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 41
nnnnkknnnn n                                                              11

<210> SEQ ID NO 42
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 42
nnnnkrnnnn n                                                              11

<210> SEQ ID NO 43
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 43
nnnnkynnnn n                                                              11

<210> SEQ ID NO 44
<211> LENGTH: 11
<212> TYPE: DNA
<213> ORGANISM: Artificial Sequence
<220> FEATURE:
<223> OTHER INFORMATION: Description of Artificial Sequence: Pooled
```

```
         probe sequence
<220> FEATURE:
<221> NAME/KEY: misc_feature
<222> LOCATION: (1)..(11)
<223> OTHER INFORMATION: n is any nucleotide complementary to the
      reference sequence.

<400> SEQUENCE: 44
nnnnkwnnnn n                                                               11

<210> SEQ ID NO 45
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 45
nnnnksnnnn n                                                               11

<210> SEQ ID NO 46
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 46
nnnnrmnnnn n                                                               11

<210> SEQ ID NO 47
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 47
nnnnrknnnn n                                                               11

<210> SEQ ID NO 48
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.
```

```
<400> SEQUENCE: 48
nnnnrrnnnn n                                                           11

<210> SEQ ID NO 49
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 49
nnnnrynnnn n                                                           11

<210> SEQ ID NO 50
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 50
nnnnrwnnnn n                                                           11

<210> SEQ ID NO 51
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 51
nnnnrsnnnn n                                                           11

<210> SEQ ID NO 52
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 52
nnnnymnnnn n                                                           11

<210> SEQ ID NO 53
<211> LENGTH: 11
```

```
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 53
nnnnyknnnn n                                                               11

<210> SEQ ID NO 54
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 54
nnnnyrnnnn n                                                               11

<210> SEQ ID NO 55
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 55
nnnnyynnnn n                                                               11

<210> SEQ ID NO 56
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 56
nnnnywnnnn n                                                               11

<210> SEQ ID NO 57
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
```

```
<222> LOCATION: (1)..(11)
<223> OTHER INFORMATION: N is any nucleotide complementary to the
      reference sequence.

<400> SEQUENCE: 57
nnnnysnnnn n                                                          11

<210> SEQ ID NO 58
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 58
nnnnwmnnnn n                                                          11

<210> SEQ ID NO 59
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 59
nnnnwknnnn n                                                          11

<210> SEQ ID NO 60
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 60
nnnnwrnnnn n                                                          11

<210> SEQ ID NO 61
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 61
nnnnwynnnn n                                                          11
```

```
<210> SEQ ID NO 62
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 62
nnnnwwnnnn n                                                          11

<210> SEQ ID NO 63
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 63
nnnnwsnnnn n                                                          11

<210> SEQ ID NO 64
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 64
nnnnsmnnnn n                                                          11

<210> SEQ ID NO 65
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 65
nnnnsknnnn n                                                          11

<210> SEQ ID NO 66
<211> LENGTH: 11
<212> TYPE: DNA
<213> ORGANISM: Artificial Sequence
<220> FEATURE:
```

```
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 66
nnnnsrnnnn n                                                            11

<210> SEQ ID NO 67
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 67
nnnnsynnnn n                                                            11

<210> SEQ ID NO 68
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any nucleotide complementary to the
      reference sequence.

<400> SEQUENCE: 68
nnnnswnnnn n                                                            11

<210> SEQ ID NO 69
<211> LENGTH: 11
<212> TYPE: DNA
<213> ORGANISM: Artificial Sequence
<220> FEATURE:
<223> OTHER INFORMATION: Description of Artificial Sequence: Pooled
      probe sequence
<220> FEATURE:
<221> NAME/KEY: misc_feature
<222> LOCATION: (1)..(11)
<223> OTHER INFORMATION: N is any sequence complementary to the
      reference sequence.

<400> SEQUENCE: 69
nnnnssnnnn n                                                            11

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Target
      sequence

<400> SEQUENCE: 70
attaaccact cacgggagct ct                                                22
```

```
<210> SEQ ID NO 71
<211> LENGTH: 13
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: misc_feature
<222> LOCATION: (1)..(13)
<223> OTHER INFORMATION: N is A, C, G, or T.

<400> SEQUENCE: 71
tggtgnkygc cct                                                            13

<210> SEQ ID NO 72
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 72
tggtgagcgc cct                                                            13

<210> SEQ ID NO 73
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 73
tggtgcgcgc cct                                                            13

<210> SEQ ID NO 74
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 74
tggtgggcgc cct                                                            13

<210> SEQ ID NO 75
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 75
tggtgtgcgc cct                                                            13

<210> SEQ ID NO 76
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 76
tggtgatcgc cct                                                            13

<210> SEQ ID NO 77
<211> LENGTH: 13
```

```
<212> TYPE: DNA
<213> ORGANISM: Artificial Sequence
<220> FEATURE:
<223> OTHER INFORMATION: Description of Artificial Sequence: Probe

<400> SEQUENCE: 77
tggtgctcgc cct                                                              13

<210> SEQ ID NO 78
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 78
tggtggtcgc cct                                                              13

<210> SEQ ID NO 79
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 79
tggtgttcgc cct                                                              13

<210> SEQ ID NO 80
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 80
tggtgagtgc cct                                                              13

<210> SEQ ID NO 81
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 81
tggtgcgtgc cct                                                              13

<210> SEQ ID NO 82
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 82
tggtgggtgc cct                                                              13

<210> SEQ ID NO 83
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 83
```

```
tggtgtgtgc cct                                                         13

<210> SEQ ID NO 84
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 84
tggtgattgc cct                                                         13

<210> SEQ ID NO 85
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 85
tggtgcttgc cct                                                         13

<210> SEQ ID NO 86
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 86
tggtggttgc cct                                                         13

<210> SEQ ID NO 87
<211> LENGTH: 13
<212> TYPE: DNA
<213> ORGANISM: Artificial Sequence
<220> FEATURE:
<223> OTHER INFORMATION: Description of Artificial Sequence: Probe

<400> SEQUENCE: 87
tggtgtttgc cct                                                         13

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 88
attaaccact cccgggagct ct                                               22

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 89
attaaccact cgcgggagct ct                                               22

<210> SEQ ID NO 90
<211> LENGTH: 22
```

```
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 90
attaaccact ctcgggagct ct                                                  22

<210> SEQ ID NO 91
<211> LENGTH: 13
<212> TYPE: DNA
<213> ORGANISM: Artificial Sequence
<220> FEATURE:
<223> OTHER INFORMATION: Description of Artificial Sequence: Pool 4
      probe
<220> FEATURE:
<221> NAME/KEY: misc_feature
<222> LOCATION: (1)..(13)
<223> OTHER INFORMATION: N is A, C, G, or T.

<400> SEQUENCE: 91
taattnkyga gtg                                                            13

<210> SEQ ID NO 92
<211> LENGTH: 13
<212> TYPE: DNA
<213> ORGANISM: Artificial Sequence
<220> FEATURE:
<223> OTHER INFORMATION: Description of Artificial Sequence: Pool 5
      probe
<220> FEATURE:
<221> NAME/KEY: misc_feature
<222> LOCATION: (1)..(13)
<223> OTHER INFORMATION: N is A, C, G, or T.

<400> SEQUENCE: 92
aattgnkrag tgc                                                            13

<210> SEQ ID NO 93
<211> LENGTH: 13
<212> TYPE: DNA
<213> ORGANISM: Artificial Sequence
<220> FEATURE:
<223> OTHER INFORMATION: Description of Artificial Sequence: Pool 6
      probe
<220> FEATURE:
<221> NAME/KEY: misc_feature
<222> LOCATION: (1)..(13)
<223> OTHER INFORMATION: N is A, C, G, or T.

<400> SEQUENCE: 93
attggnkrgt gcc                                                            13

<210> SEQ ID NO 94
<211> LENGTH: 13
<212> TYPE: DNA
<213> ORGANISM: Artificial Sequence
<220> FEATURE:
<223> OTHER INFORMATION: Description of Artificial Sequence: Mutant
      sequence
<220> FEATURE:
<221> NAME/KEY: misc_feature
<222> LOCATION: (1)..(13)
<223> OTHER INFORMATION: N is A, C, G, or T.

<400> SEQUENCE: 94
ttggtnmrtg ccc                                                            13
```

```
<210> SEQ ID NO 95
<211> LENGTH: 13
<212> TYPE: DNA
<213> ORGANISM: Artificial Sequence
<220> FEATURE:
<223> OTHER INFORMATION: Description of Artificial Sequence: Pool 8
      probe
<220> FEATURE:
<221> NAME/KEY: misc_feature
<222> LOCATION: (1)..(13)
<223> OTHER INFORMATION: N is A, C, G, or T.

<400> SEQUENCE: 95
tggtgnkygc cct                                                       13

<210> SEQ ID NO 96
<211> LENGTH: 13
<212> TYPE: DNA
<213> ORGANISM: Artificial Sequence
<220> FEATURE:
<223> OTHER INFORMATION: Description of Artificial Sequence: Pool 9
      probe
<220> FEATURE:
<221> NAME/KEY: misc_feature
<222> LOCATION: ()..()
<223> OTHER INFORMATION: N is A ,C, G, or T.

<400> SEQUENCE: 96
ggtgankrcc ctc                                                       13

<210> SEQ ID NO 97
<211> LENGTH: 13
<212> TYPE: DNA
<213> ORGANISM: Artificial Sequence
<220> FEATURE:
<223> OTHER INFORMATION: Description of Artificial Sequence: Pool 10
      probe
<220> FEATURE:
<221> NAME/KEY: misc_feature
<222> LOCATION: (1)..(13)
<223> OTHER INFORMATION: N is A, C, G, or T.

<400> SEQUENCE: 97
gtgagnkycc tcg                                                       13

<210> SEQ ID NO 98
<211> LENGTH: 13
<212> TYPE: DNA
<213> ORGANISM: Artificial Sequence
<220> FEATURE:
<223> OTHER INFORMATION: Description of Artificial Sequence: Pool 11
      probe
<220> FEATURE:
<221> NAME/KEY: misc_feature
<222> LOCATION: (1)..(13)
<223> OTHER INFORMATION: N is A, C, G, or T.

<400> SEQUENCE: 98
tgagtnmyct cga                                                       13

<210> SEQ ID NO 99
<211> LENGTH: 13
<212> TYPE: DNA
<213> ORGANISM: Artificial Sequence
<220> FEATURE:
<223> OTHER INFORMATION: Description of Artificial Sequence: Pool 12
      probe
<220> FEATURE:
<221> NAME/KEY: misc_feature
<222> LOCATION: (1)..(13)
<223> OTHER INFORMATION: N is A, C, G, or T.
```

```
<400> SEQUENCE: 99
gagtgnmytc gag                                                        13

<210> SEQ ID NO 100
<211> LENGTH: 13
<212> TYPE: DNA
<213> ORGANISM: Artificial Sequence
<220> FEATURE:
<223> OTHER INFORMATION: Description of Artificial Sequence: Pool 13
      probe
<220> FEATURE:
<221> NAME/KEY: misc_feature
<222> LOCATION: (1)..(13)
<223> OTHER INFORMATION: N is A, C, G, or T.

<400> SEQUENCE: 100
agtgcnmycg aga                                                        13

<210> SEQ ID NO 101
<211> LENGTH: 13
<212> TYPE: DNA
<213> ORGANISM: Artificial Sequence
<220> FEATURE:
<223> OTHER INFORMATION: Description of Artificial Sequence: Probe 55
<220> FEATURE:
<221> NAME/KEY: misc_feature
<222> LOCATION: (1)..(13)
<223> OTHER INFORMATION: N is A, C, G, or T.

<400> SEQUENCE: 101
attnkygagt gcc                                                        13

<210> SEQ ID NO 102
<211> LENGTH: 13
<212> TYPE: DNA
<213> ORGANISM: Artificial Sequence
<220> FEATURE:
<223> OTHER INFORMATION: Description of Artificial Sequence: Probe 56
<220> FEATURE:
<221> NAME/KEY: misc_feature
<222> LOCATION: (1)..(13)
<223> OTHER INFORMATION: N is A, C, G, or T.

<400> SEQUENCE: 102
attgnkragt gcc                                                        13

<210> SEQ ID NO 103
<211> LENGTH: 13
<212> TYPE: DNA
<213> ORGANISM: Artificial Sequence
<220> FEATURE:
<223> OTHER INFORMATION: Description of Artificial Sequence: Probe 58
<220> FEATURE:
<221> NAME/KEY: misc_feature
<222> LOCATION: (1)..(13)
<223> OTHER INFORMATION: N is A, C, G, or T.

<400> SEQUENCE: 103
attrgtnmgt gcc                                                        13

<210> SEQ ID NO 104
<211> LENGTH: 13
<212> TYPE: DNA
<213> ORGANISM: Artificial Sequence
<220> FEATURE:
<223> OTHER INFORMATION: Description of Artificial Sequence: Probe 59
<220> FEATURE:
<221> NAME/KEY: misc_feature
```

```
<222> LOCATION: (1)..(13)
<223> OTHER INFORMATION: N is A, C, G, or T.

<400> SEQUENCE: 104
attkrtgngt gcc                                                          13

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 105
taagcactca cgggagca                                                     18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 106
taatcactca cgggagca                                                     18

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 107
taaacactca cgggagca                                                     18

<210> SEQ ID NO 108
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 108
taacgactca cgggagca                                                     18

<210> SEQ ID NO 109
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 109
taactactca cgggagca                                                     18

<210> SEQ ID NO 110
<211> LENGTH: 18
<212> TYPE: DNA
<213> ORGANISM: Artificial Sequence
<220> FEATURE:
<223> OTHER INFORMATION: Description of Artificial Sequence: Mutant
```

-continued
        sequence

<400> SEQUENCE: 110
taacaactca cgggagca                                                   18

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 111
taaccagtca cgggagca                                                   18

<210> SEQ ID NO 112
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 112
taaccattca cgggagca                                                   18

<210> SEQ ID NO 113
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 113
taaccaatca cgggagca                                                   18

<210> SEQ ID NO 114
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 114
taaccacaca cgggagca                                                   18

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

<400> SEQUENCE: 115
taaccaccca cgggagca                                                   18

<210> SEQ ID NO 116
<211> LENGTH: 18
<212> TYPE: DNA
<213> ORGANISM: Artificial Sequence
<220> FEATURE:
<223> OTHER INFORMATION: Description of Artificial Sequence: Mutant
      sequence

```
<400> SEQUENCE: 116
taaccacgca cgggagca                                                 18

<210> SEQ ID NO 117
<211> LENGTH: 10
<212> TYPE: DNA
<213> ORGANISM: Artificial Sequence
<220> FEATURE:
<223> OTHER INFORMATION: Description of Artificial Sequence: Target
      sequence

<400> SEQUENCE: 117
cacgggagca                                                          10

<210> SEQ ID NO 118
<211> LENGTH: 14
<212> TYPE: DNA
<213> ORGANISM: Artificial Sequence
<220> FEATURE:
<223> OTHER INFORMATION: Description of Artificial Sequence: Pool 1(1)
      probe
<220> FEATURE:
<221> NAME/KEY: misc_feature
<222> LOCATION: (1)..(14)
<223> OTHER INFORMATION: N is A, C, G, or T.

<400> SEQUENCE: 118
attgntnagt gccc                                                     14

<210> SEQ ID NO 119
<211> LENGTH: 14
<212> TYPE: DNA
<213> ORGANISM: Artificial Sequence
<220> FEATURE:
<223> OTHER INFORMATION: Description of Artificial Sequence: Pool 2(2)
      probe
<220> FEATURE:
<221> NAME/KEY: misc_feature
<222> LOCATION: (1)..(14)
<223> OTHER INFORMATION: N is A, C, G, or T.

<400> SEQUENCE: 119
attggnnagt gccc                                                     14

<210> SEQ ID NO 120
<211> LENGTH: 14
<212> TYPE: DNA
<213> ORGANISM: Artificial Sequence
<220> FEATURE:
<223> OTHER INFORMATION: Description of Artificial Sequence: Pool 3(4)
      probe

<400> SEQUENCE: 120
attgyrydgt gccc                                                     14

<210> SEQ ID NO 121
<211> LENGTH: 14
<212> TYPE: DNA
<213> ORGANISM: Artificial Sequence
<220> FEATURE:
<223> OTHER INFORMATION: Description of Artificial Sequence: Pool 4(8)
      probe

<400> SEQUENCE: 121
attgmwmbgt gccc                                                     14
```

```
<210> SEQ ID NO 122
<211> LENGTH: 14
<212> TYPE: DNA
<213> ORGANISM: Artificial Sequence
<220> FEATURE:
<223> OTHER INFORMATION: Description of Artificial Sequence: Pool 1(1)
<220> FEATURE:
<221> NAME/KEY: misc_feature
<222> LOCATION: (1)..(14)
<223> OTHER INFORMATION: N is A, C, G, or T.

<400> SEQUENCE: 122
attgnanagt gccc                                                          14

<210> SEQ ID NO 123
<211> LENGTH: 14
<212> TYPE: DNA
<213> ORGANISM: Artificial Sequence
<220> FEATURE:
<223> OTHER INFORMATION: Description of Artificial Sequence: Pool 3(4)

<400> SEQUENCE: 123
attgryrhgt gccc                                                          14

<210> SEQ ID NO 124
<211> LENGTH: 14
<212> TYPE: DNA
<213> ORGANISM: Artificial Sequence
<220> FEATURE:
<223> OTHER INFORMATION: Description of Artificial Sequence: Pool 4(8)

<400> SEQUENCE: 124
attgkwkvgt gccc                                                          14

<210> SEQ ID NO 125
<211> LENGTH: 14
<212> TYPE: DNA
<213> ORGANISM: Artificial Sequence
<220> FEATURE:
<223> OTHER INFORMATION: Description of Artificial Sequence: Pool 5(c)
      target sequence

<400> SEQUENCE: 125
attgdhsmgt gccc                                                          14

<210> SEQ ID NO 126
<211> LENGTH: 23
<212> TYPE: DNA
<213> ORGANISM: Artificial Sequence
<220> FEATURE:
<223> OTHER INFORMATION: Description of Artificial Sequence: Reference
      sequence

<400> SEQUENCE: 126
tggctacgag gaatcatctg tta                                                23

<210> SEQ ID NO 127
<211> LENGTH: 10
<212> TYPE: DNA
<213> ORGANISM: Artificial Sequence
<220> FEATURE:
<223> OTHER INFORMATION: Description of Artificial Sequence:
      Complementary sequence

<400> SEQUENCE: 127 tagccccctcg                                                              10
```

```
<210> SEQ ID NO 128
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 128
tagccccacg                                                              10

<210> SEQ ID NO 129
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 129
tagccccccg                                                              10

<210> SEQ ID NO 130
<211> LENGTH: 10
<212> TYPE: DNA
<213> ORGANISM: Artificial Sequence
<220> FEATURE:
<223> OTHER INFORMATION: Description of Artificial Sequence: Probe

<400> SEQUENCE: 130
tagccccgcg                                                              10

<210> SEQ ID NO 131
<211> LENGTH: 16
<212> TYPE: DNA
<213> ORGANISM: Artificial Sequence
<220> FEATURE:
<223> OTHER INFORMATION: Description of Artificial Sequence: Reference
      sequence

<400> SEQUENCE: 131
agtaccagat ctctaa                                                       16

<210> SEQ ID NO 132
<211> LENGTH: 12
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: misc_feature
<222> LOCATION: (1)..(12)
<223> OTHER INFORMATION: N is A, C, G, or T.

<400> SEQUENCE: 132
catggncaga ga                                                           12

<210> SEQ ID NO 133
<211> LENGTH: 25
<212> TYPE: DNA
<213> ORGANISM: Artificial Sequence
<220> FEATURE:
<223> OTHER INFORMATION: Description of Artificial Sequence: CYP2DE1F

<400> SEQUENCE: 133
gccaggtgtg tccagaggag cccat                                             25

<210> SEQ ID NO 134
<211> LENGTH: 25
```

```
<212> TYPE: DNA
<213> ORGANISM: Artificial Sequence
<220> FEATURE:
<223> OTHER INFORMATION: Description of Artificial Sequence: CYP2DE1R

<400> SEQUENCE: 134
ctggtagggg agcctcagca cctct                                           25

<210> SEQ ID NO 135
<211> LENGTH: 26
<212> TYPE: DNA
<213> ORGANISM: Artificial Sequence
<220> FEATURE:
<223> OTHER INFORMATION: Description of Artificial Sequence: CYP2DE2F

<400> SEQUENCE: 135
taggactagg acctgtagtc tggggt                                          26

<210> SEQ ID NO 136
<211> LENGTH: 24
<212> TYPE: DNA
<213> ORGANISM: Artificial Sequence
<220> FEATURE:
<223> OTHER INFORMATION: Description of Artificial Sequence: CYP2DE2R

<400> SEQUENCE: 136
ggtcccacgg aaatctgtct ctgt                                            24

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: CYP2DE34F

<400> SEQUENCE: 137
ctaatgcctt catggccacg cgca                                            24

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: CYP2DE34R

<400> SEQUENCE: 138
tcgggagctc gccctgcaga ga                                              22

<210> SEQ ID NO 139
<211> LENGTH: 24
<212> TYPE: DNA
<213> ORGANISM: Artificial Sequence
<220> FEATURE:
<223> OTHER INFORMATION: Description of Artificial Sequence: CYP2DE5F

<400> SEQUENCE: 139
gggcctgaga cttgtccagg tgaa                                            24

<210> SEQ ID NO 140
<211> LENGTH: 25
<212> TYPE: DNA
<213> ORGANISM: Artificial Sequence
<220> FEATURE:
<223> OTHER INFORMATION: Description of Artificial Sequence: CYP2DE5R

<400> SEQUENCE: 140
```

```
ccctcattcc tcctgggacg ctcaa                                          25

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: CYP2DE6F

<400> SEQUENCE: 141
cccgttctgt cccgagtatg ctct                                           24

<210> SEQ ID NO 142
<211> LENGTH: 24
<212> TYPE: DNA
<213> ORGANISM: Artificial Sequence
<220> FEATURE:
<223> OTHER INFORMATION: Description of Artificial Sequence: CYP2DE6R

<400> SEQUENCE: 142
tcggcccctg cactgtttcc caga                                           24

<210> SEQ ID NO 143
<211> LENGTH: 23
<212> TYPE: DNA
<213> ORGANISM: Artificial Sequence
<220> FEATURE:
<223> OTHER INFORMATION: Description of Artificial Sequence: CYP2DE7F

<400> SEQUENCE: 143
gctgacccat tgtggggacg cat                                            23

<210> SEQ ID NO 144
<211> LENGTH: 26
<212> TYPE: DNA
<213> ORGANISM: Artificial Sequence
<220> FEATURE:
<223> OTHER INFORMATION: Description of Artificial Sequence: CYP2DE7R

<400> SEQUENCE: 144
ctatcaccag gtgctggtgc tgagct                                         26

<210> SEQ ID NO 145
<211> LENGTH: 25
<212> TYPE: DNA
<213> ORGANISM: Artificial Sequence
<220> FEATURE:
<223> OTHER INFORMATION: Description of Artificial Sequence: CYP2DE89F

<400> SEQUENCE: 145
gggagacaaa ccaggacctg ccaga                                          25

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: CYP2DE89R

<400> SEQUENCE: 146
ctcagcctca acgtacccct gtct                                           24

<210> SEQ ID NO 147
<211> LENGTH: 27
<212> TYPE: DNA
<213> ORGANISM: Artificial Sequence
```

```
<220> FEATURE:
<223> OTHER INFORMATION: Description of Artificial Sequence: CYP2D678-F

<400> SEQUENCE: 147
tgagagcagc ttcaatgatg agaacct                                          27

<210> SEQ ID NO 148
<211> LENGTH: 25
<212> TYPE: DNA
<213> ORGANISM: Artificial Sequence
<220> FEATURE:
<223> OTHER INFORMATION: Description of Artificial Sequence: CYP2D678-R

<400> SEQUENCE: 148
gtaggatcat gagcaggagg cccca                                            25

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: CYP-PCR8-F

<400> SEQUENCE: 149
tcccccgtgt gtttggtggc a                                                21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: CYP-PCR9-R

<400> SEQUENCE: 150
tgctttattg tacattagag c                                                21

<210> SEQ ID NO 151
<211> LENGTH: 12
<212> TYPE: DNA
<213> ORGANISM: Artificial Sequence
<220> FEATURE:
<223> OTHER INFORMATION: Description of Artificial Sequence: Target
      sequence

<400> SEQUENCE: 151
agcctagctg aa                                                          12

<210> SEQ ID NO 152
<211> LENGTH: 12
<212> TYPE: DNA
<213> ORGANISM: Artificial Sequence
<220> FEATURE:
<223> OTHER INFORMATION: Description of Artificial Sequence:
      Hybridizable probe

<400> SEQUENCE: 152
tcggatcgac tt                                                          12

<210> SEQ ID NO 153
<211> LENGTH: 22
<212> TYPE: DNA
<213> ORGANISM: Artificial Sequence
<220> FEATURE:
<223> OTHER INFORMATION: Description of Artificial Sequence: T3 promoter
      sequence

<400> SEQUENCE: 153
```

```
cggaattaac cctcactaaa gg                                          22

<210> SEQ ID NO 154
<211> LENGTH: 22
<212> TYPE: DNA
<213> ORGANISM: Artificial Sequence
<220> FEATURE:
<223> OTHER INFORMATION: Description of Artificial Sequence: T3 promoter
      sequence

<400> SEQUENCE: 154
aattaaccct cactaaaggg ag                                          22

<210> SEQ ID NO 155
<211> LENGTH: 22
<212> TYPE: DNA
<213> ORGANISM: Artificial Sequence
<220> FEATURE:
<223> OTHER INFORMATION: Description of Artificial Sequence: T7 promoter
      sequence

<400> SEQUENCE: 155
taatacgact cactataggg ag                                          22

<210> SEQ ID NO 156
<211> LENGTH: 20
<212> TYPE: DNA
<213> ORGANISM: Artificial Sequence
<220> FEATURE:
<223> OTHER INFORMATION: Description of Artificial Sequence: SP6
      promoter sequence

<400> SEQUENCE: 156
atttaggtga cactatagaa                                             20
```

ARRAYS OF NUCLEIC ACID PROBES FOR ANALYZING BIOTRANSFORMATION GENES

CROSS-REFERENCE TO RELATED APPLICATIONS

The present application is a continuation of application Ser. No. 11/367,800 filed Mar. 3, 2006 now abandoned, which is a continuation of application Ser. No. 09/798,260, filed on May 1, 2002 now abandoned, which is a continuation of application Ser. No. 08/778,794, filed on Jan. 3, 1997, now U.S. Pat. No. 6,309,823, which is a continuation-in-part of application Ser. No. 08/544,381, filed on Oct. 10, 1995, now U.S. Pat. No. 6,027,880, which is a continuation-in-part of application Ser. No. 08/510,521, filed Aug. 2, 1995 now U.S. Pat. No. 7,115,364, which is a continuation-in-part of PCT/US94/12305, filed Oct. 26, 1994, which is a continuation-in-part of application Ser .No. 08/284,064, filed Aug. 2, 1994 (now abandoned), which is a continuation-in-part of application Ser. No. 08/143,312, filed Oct. 26, 1993 (now abandoned), each of which is incorporated by reference in its entirety for all purposes.

Research leading to the invention was funded in part by NIH grant No. 1R01HG00813-01, and the government may have certain rights to the invention.

BACKGROUND OF THE INVENTION

1. Field of the Invention

The present invention provides arrays of oligonucleotide probes immobilized in microfabricated patterns on chips for analyzing biotransformation genes, such as cytochromes P450.

2. Description of Related Art

Virtually all substances introduced into the human body (xenobiotics) as well as most endogenous compounds (endobiotics) undergo some form of biotransformation in order to be eliminated from the body. Many enzymes contribute to the phase I and phase II metabolic pathways responsible for this bioprocessing. Phase I enzymes include reductases, oxidases and hydrolases. Among the phase I enzymes are the cytochromes P450, a superfamily of hemoproteins involved in the oxidative metabolism of steroids, fatty adds, prostaglandins, leukotrienes, biogenic amines, pheromones, plant metabolites and chemical carcinogens as well as a large number of important drugs (Heim & Meyer, Genomics 14, 49-58 (1992)). Phase II enzymes are primarily transferases responsible for transferring glucuronic acid, sulfate or glutathione to compounds already processed by phase I enzymes (Gonzales & Idle, Clin. Pharmacokinet 26, 59-74 (1994)). Phase II enzymes include epoxide hydrolase, catalase, glutathione peroxidase, superoxide dismutase and glutathione S-transferase.

Many drugs are metabolized by biotransformation enzymes. For some drugs, metabolism occurs after the drug has exerted its desired effect, and result in detoxification of the drug and elimination of the drug from the body; Similarly, the biotransformation enzymes also have roles in detoxifying harmful environmental compounds. For other drugs, metabolism is required to convert the drug to an active state before the drug can exert its desired effect.

Genetic polymorphisms of cytochromes P450 and other biotransformation enzymes result in phenotypically-distinct subpopulations that differ in their ability to perform biotransformations of particular drugs and other chemical compounds. These phenotypic distinctions have important implications for selection of drugs. For example, a drug that is safe when administered to most human may cause intolerable side-effects in an individual suffering from a defect in an enzyme required for detoxification of the drug. Alternatively, a drug that is effective in most humans may be ineffective in a particular subpopulation because of lack of a enzyme required for conversion of the drug to a metabolically active form. Further, individuals lacking a biotransformation enzyme are often susceptible to cancers from environmental chemicals due to inability to detoxify the chemicals. Eichelbaum et al., Toxicology Letters 64/65, 155-122 (1992). Accordingly, it is important to identify individuals who are deficient in a particular P450 enzyme., so that drugs known or suspected of being metabolized by the enzyme are not used, or used only with special precautions (e.g., reduced dosage, close monitoring) in such individuals. Identification of such individuals is also important so that such individuals can be subjected to regular monitoring for the onset of cancers.

Existing methods of identifying deficiencies are not entirely satisfactory. Patient metabolic profiles are currently assessed with a bioassay after a probe drug administration. For example, a poor drug metabolizer with a CYP2D6 defect is identified by administering one of the probe drugs, debrisoquine, sparteine or dextromethorphan, then testing urine for the ratio of unmodified to modified drug. Poor metabolizers (PM) exhibit physiologic accumulation of unmodified drug and have a high metabolic ratio of probe drug to metabolite. This bioassay has a number of limitations: lack of patient cooperation, adverse reactions to probe drugs, and inaccuracy due to coadministration of other pharmacological agents or disease effects. Genetic assays by RFLP (restriction fragment length polymorphism), ASO PCR (allele specific oligonucleotide hybridization to PCR products or PCR using mutant/wildtype specific oligo primers), SSCP (single stranded conformation polymorphism) and TGGE/DGGE (temperature or denaturing gradient gel electrophoresis), MDE (mutation detection electrophoresis) are time-consuming, technically demanding and limited in the number of gene mutation sites that can be tested at one time.

The difficulties inherent in previous methods are overcome by the use of DNA chips to analyze mutations in biotransformation genes. The development of VLSIPS™ technology has provided methods for making very large arrays of oligonucleotide probes in very small areas. See U.S. Pat. No. 5,143,854, WO 90/15070 and WO 92/10092, each of which is incorporated herein by reference. U.S. Ser. No. 08/082,937, filed Jun. 25, 1993, describes methods for making arrays of oligonucleotide probes that can be used to provide the complete sequence of a target nucleic acid and to detect the presence of a nucleic acid containing a specific nucleotide sequence. Others have also proposed the use of large numbers of oligonucleotide probes to provide the complete nucleic acid sequence of a target nucleic acid but failed to provide an enabling method for using arrays of immobilized probes for this purpose. See U.S. Pat. Nos. 5,202,231, 5,002,867 and WO 93/17126.

Microfabricated arrays of large numbers of oligonucleotide probes, called "DNA chips" offer great promise for a wide variety of applications. The present application describes the use of such chips for inter alia analysis of the biotransformation genes, such as cytochromes P450.

SUMMARY OF THE INVENTION

The invention provides arrays of probes immobilized on a solid support for analyzing biotransformation genes. In a first embodiment, the invention provides a tiling strategy employing an array of immobilized oligonucleotide probes comprising at least two sets of probes. A first probe set comprises a plurality of probes, each probe comprising a segment of at least three nucleotides exactly complementary to a subsequence of a reference sequence from a biotransformation gene, the segment including at least one interrogation position complementary to a corresponding nucleotide in the reference sequence. A second probe set comprises a corresponding probe for each probe in the first probe set, the corresponding probe in the second probe set being identical to a sequence comprising the corresponding probe from the first probe set or a subsequence of at least three nucleotides thereof that includes the at least one interrogation position, except that the at least one interrogation position is occupied by a different nucleotide in each of the two corresponding probes from the first and second probe sets. The probes in the first probe set have at least two interrogation positions corresponding to two contiguous nucleotides in the reference sequence. One interrogation position corresponds to one of the contiguous nucleotides, and the other interrogation position to the other. In this, and other forms of array, biotransformation genes of particular interest for analysis include cytochromes P450, particularly 2D6 and 2C19, N-acetyl transferase II, glucose 6-phosphate dehydrogenase, pseudocholinesterase, catechol-O-methyl transferase, and dihydropyridine dehydrogenase.

In a second embodiment, the invention provides a tiling strategy employing an array comprising four probe sets. A first probe set comprises a plurality of probes, each probe comprising a segment of at least three nucleotides exactly complementary to a subsequence of a reference sequence from a biotransformation gene, the segment including at least one interrogation position complementary to a corresponding nucleotide in the reference sequence. Second, third and fourth probe sets each comprise a corresponding probe for each probe in the first probe set. The probes in the second, third and fourth probe sets are identical to a sequence comprising the corresponding probe from the first probe set or a subsequence of at least three nucleotides thereof that includes the at least one interrogation position, except that the at least one interrogation position is occupied by a different nucleotide in each of the four corresponding probes from the four probe sets.

In a third embodiment, the invention provides arrays comprising first and second groups of probe sets, each group comprising first, second and optionally, third and fourth probe sets as defined above. The first probe sets in the first and second groups are designed to be exactly complementary to first and second reference sequences. For example, the first reference can include a site of mutation rendering the gene nonfunctional, and the second reference sequence can include a site of a silent polymorphism.

In a fourth embodiment, the invention provides a block of oligonucleotides probes (sometimes referred to as an optiblock) immobilized on a support. The array comprises a perfectly matched probe comprising a segment of at least three nucleotides exactly complementary to a subsequence of a reference sequence from a biotransformation gene, the segment having a plurality of interrogation positions respectively corresponding to a plurality of nucleotides in the reference sequence. For each interrogation position, the array further comprises three mismatched probes, each identical to a sequence comprising the perfectly matched probe or a subsequence of at least three nucleotides thereof including the plurality of interrogation positions, except in the interrogation position, which is occupied by a different nucleotide in each of the three mismatched probes and the perfectly matched probe.

In a fifth embodiment (sometimes referred to as deletion tiling), the invention provides an array comprising at least four probes. A first probe comprises first and second segments, each of at least three nucleotides and exactly complementary to first and second subsequences of a reference sequence from a biotransformation gene, the segments including at least one interrogation position corresponding to a nucleotide in the reference sequence, wherein either (1) the first and second subsequences are noncontiguous, or (2) the first and second subsequences are contiguous and the first and second segments are inverted relative to the complement of the first and second subsequences in the reference sequence. The array further comprises second, third and fourth probes, identical to a sequence comprising the first probe or a subsequence thereof comprising at least three nucleotides from each of the first and second segments, except in the at least one interrogation position, which differs in each of the probes.

In a sixth embodiment, the invention provides a method of comparing a target nucleic acid with a reference sequence from a biotransformation gene. The method comprises hybridizing a sample comprising the target nucleic acid to one of the arrays of oligonucleotide probes described above. The method then determines which probes, relative to one another, specifically bind to the target nucleic acid, the relative specific binding of corresponding probes indicating whether a nucleotide in the target sequence is the same or different from the corresponding nucleotide in the reference sequence.

For example, for the array of the second embodiment which has four probe sets, the array can be analyzed by comparing the relative specific binding of four corresponding probes from the first, second, third and fourth probe sets, assigning a nucleotide in the target sequence as the complement of the interrogation position of the probe having the greatest specific binding, and repeating these steps until each nucleotide of interest in the target sequence has been assigned.

In some methods, the reference sequence includes a site of a mutation in the biotransformation gene and a silent polymorphism in or flanking the biotransformation gene, and the target nucleic acid comprises one or more different alleles of the biotransformation gene. In this situation, the relative specific binding of probes having an interrogation position aligned with the silent polymorphism indicates the number of different alleles and the relative specific binding of probes having an interrogation position aligned with the mutation indicates whether the mutation is present in at least one of the alleles.

BRIEF DESCRIPTION OF THE FIGURES

FIG. 3B (SEQ ID NOS:16, 4, 6-10, 12, 13, 15, respectively): Arrangement of probe sets in tiling arrays lacking a perfectly matched probe set.

FIG. 4A (SEQ ID NO:1): Exemplary arrangement of lanes on a chip. The chip shows four probe sets, each having five probes and each having a total of five interrogation positions (I1-I5), one per probe.

FIG. 4B (SEQ ID NO:17): A tiling strategy for analyzing closing spaced mutations.

FIG. 4C (SEQ ID NO:18): A tiling strategy for avoiding loss of a signal due to probe self-annealing.

FIG. 7 (SEQ ID NO:1): Block tiling strategy. The perfectly matched probe has three interrogation positions. The probes from the other probe sets have only one of these interrogation positions.

FIG. 8 (SEQ ID NO:1): Multiplex tiling strategy. Each probe has two interrogation positions.

FIG. 9 (SEQ ID NO:21): Helper mutation strategy. The segment of complementarity differs from the complement of the reference sequence at a helper mutation as well as the interrogation position.

FIG. 11: Alternative tiling for analysis of CYP2D6/CYP2D7 polymorphism.

FIG. 12: Optiblock for analysis of CYP2D6 P34S polymorphism.

FIG. 17: Use of the VLSIPS™ process to prepare "nucleoside combinatorials" or oligonucleotides synthesized by coupling all four nucleosides to form dimers, trimers, and so forth.

DETAILED DESCRIPTION OF THE INVENTION

Figure 1:
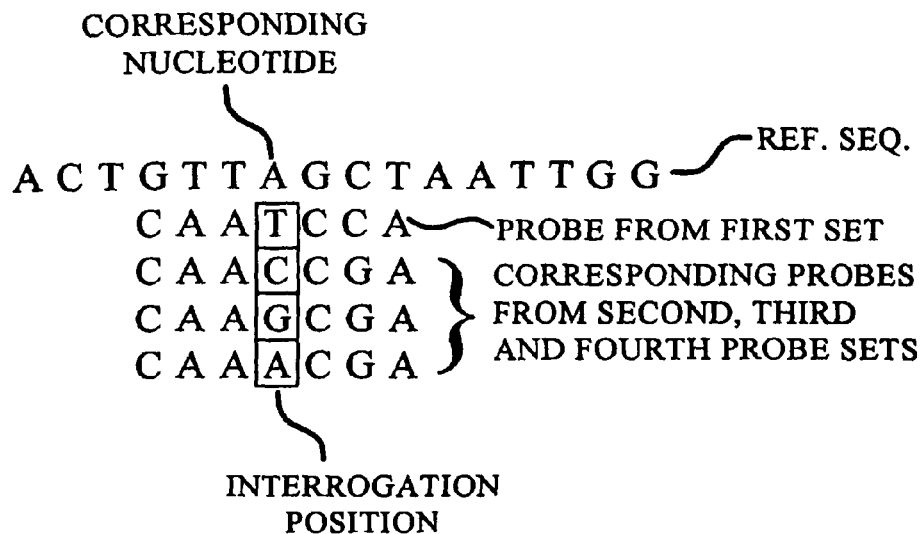
FIG. 1: Basic tilting strategy. The figure illustrates the relationship between an interrogation position (I) and a corresponding nucleotide (n) in the reference sequence (SEQ ID NO:1), and between a probe from the first probe set and corresponding probes from the second, third and fourth probe sets.

The invention provides a number of strategies for comparing a polynucleotide of known sequence (a reference sequence) with variants of that sequence (target sequences). The comparison can be performed at the level of entire genomes, chromosomes, genes, exons or introns, or can focus on individual mutant sites and immediately adjacent bases. The strategies allow detection of variations, such as mutations or polymorphisms, in the target sequence irrespective whether a particular variant has previously been characterized. The strategies both define the nature of a variant and identify its location in a target sequence.

The strategies employ arrays of oligonucleotide probes immobilized to a solid support. Target sequences are analyzed by determining the extent of hybridization at particular probes in the array. The strategy in selection of probes facilitates distinction between perfectly matched probes and probes showing single-base or other degrees of mismatches. The strategy usually entails sampling each nucleotide of interest in a target sequence several times, thereby achieving a high degree of confidence in its identity. This level of confidence is further increased by sampling of adjacent nucleotides in the target sequence to nucleotides of interest. The present tiling strategies result in sequencing and comparison methods suitable for routine large-scale practice with a high degree of confidence in the sequence output.

I. General Tiling Strategies

A. Selection of Reference Sequence

The chips are designed to contain probes exhibiting complementarity to one or more selected reference sequence whose sequence is known. The chips are used to read a target sequence comprising either the reference sequence itself or variants of that sequence. Target sequences may differ from the reference sequence at one or more positions but show a high overall degree of sequence identity with the reference sequence (e.g., at. least 75, 90, 95, 99, 99.9 or 99.99%). Any polynucleotide of known sequence can be selected as a reference sequence. Reference sequences of interest include sequences known to include mutations or polymorphisms associated with phenotypic changes having clinical significance in human patients. For example, the CFTR gene and P53 gene in humans have been identified as the location of several mutations resulting in cystic fibrosis or cancer respectively. Other reference sequences of interest include those that serve to identify pathogenic microorganisms and/or are the site of mutations by which such microorganisms acquire drug resistance (e.g., the HIV reverse transcriptase gene). Other reference sequences of interest include regions where polymorphic variations are known to occur (e.g., the D-loop region of mitochondrial DNA). These reference sequences have utility for, e.g., forensic or epidemiological studies. Other reference sequences of interest include p34 (related to p53), p65 (implicated in breast, prostate and liver cancer), and DNA segments encoding cytochromes P450 and other biotransformation genes (see Meyer et al., *Pharmac. Ther.* 46, 349-355 (1990)). Other reference sequences of interest include those from the genome of pathogenic viruses (e.g., hepatitis (A, B, or C), herpes virus (e.g., VZV, HSV-1, HAV-6, HSV-II, and CMV, Epstein Barr virus), *adenovirus*, influenza virus, *flaviviruses, echovirus, rhinovirus,* coxsackie virus, *cornovirus*, respiratory syncytial virus, mumps virus, *rotavirus,* measles virus, rubella virus, *parvovirus,* vaccinia virus, HTLV virus, dengue virus, *papillomavirus,* molluscum virus, *poliovirus,* rabies virus, JC virus and arboviral encephalitis virus. Other reference sequences of interest are from genomes or episomes. of pathogenic bacteria, particularly regions that confer drug resistance or allow phylogenic characterization of the host (e.g., 16S rRNA or corresponding DNA). For example, such bacteria include chlamydia, rickettsial bacteria, mycobacteria, staphylococci, treptocci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lymes disease bacteria. Other reference sequences of interest include those in which mutations result in the following autosomal recessive disorders: sickle cell anemia, β-thalassemia, phenylketonuria, galactosemia, Wilson's disease, hemochromatosis, severe combined immunodeficiency, alpha-1-antitrypsin deficiency, albinism, alkaptonuria, lysosomal storage diseases and Ehlers-Danlos syndrome. Other reference sequences of interest include those in which mutations result in X-linked recessive disorders: hemophilia, glucose-6-phosphate dehydrogenase, agammaglobulimenia, diabetes insipidus, Lesch-Nyhan syndrome, muscular dystrophy, Wiskott-Aldrich syndrome, Fabry's disease and fragile X-syndrome. Other reference sequences of interest includes those in which mutations result in the following autosomal dominant disorders: familial hyperchoiesterolemia, polycystic kidney disease, Huntingdon's disease, hereditary spherocytosis, Marfan's syndrome, von.Willebrand's disease, neurofibromatosis, tuberous sclerosis, hereditary hemorrhagic telangiectasia, familial colonic polyposis, Ehlers-Danlos syndrome, myotonic dystrophy, muscular dystrophy, osteogenesis imperfecta, acute intermittent porphyria, and von Hippel-Lindau disease.

The length of a reference sequence can vary widely from a full-length genome, to an individual chromosome, episome, gene, component of a gene, such as an exon, intron or regulatory sequences, to a few nucleotides. A reference sequence of between about 2, 5, 10, 20, 50, 100, 5000, 1000, 5,000 or 10,000, 20,000 or 100,000 nucleotides is common. Sometimes only particular regions of a sequence (e.g., exons of a gene) are of interest. In such situations, the particular regions can be considered as separate reference sequences or can be considered as components of a single reference sequence, as matter of arbitrary choice.

A reference sequence can be any naturally occurring, mutant, consensus or purely hypothetical sequence of nucleotides, RNA or DNA. For example, sequences can be obtained from computer data bases, publications or can be determined or conceived de novo. Usually, a reference sequence is selected to show a high degree of sequence identity to envisaged target sequences. Often, particularly, where a significant degree of divergence is anticipated between target sequences, more than one reference sequence is selected. Combinations of wildtype and mutant reference sequences are employed in several applications of the tiling strategy.

B. Chip Design

1. Basic Tiling Strategy

The basic tiling strategy provides an array of immobilized probes for analysis of target sequences showing a high degree of sequence identity to one or more selected reference sequences. The strategy is first illustrated for an array that is subdivided into four probe sets, although it will be apparent that in some situations, satisfactory results are obtained from only two probe sets. A first probe set comprises a plurality of probes exhibiting perfect complementarity with a selected reference sequence. The perfect complementarity usually exists throughout the length of the probe. However, probes having a segment or segments of perfect complementarity that is/are flanked by leading or trailing sequences lacking complementarity to the reference sequence can also be used. Within a segment of complementarity, each probe in the first probe set has at least one interrogation position that corresponds to a nucleotide in the reference sequence. That is, the interrogation position is aligned with the corresponding nucleotide in the reference sequence, when the probe and reference sequence are aligned to maximize complementarity between the two. If a probe has more than one interrogation position, each corresponds with a respective nucleotide in the reference sequence. The identity of an interrogation position and corresponding nucleotide in a particular probe in the first probe set cannot be determined simply by inspection of the probe in the first set. As will become apparent, an interrogation position and corresponding nucleotide is defined by the comparative structures of probes in the first probe set and corresponding probes from additional probe sets.

In principle, a probe could have an interrogation position at each position in the segment complementary to the reference sequence. Sometimes, interrogation positions provide more accurate data when located away from the ends of a segment of complementarity. Thus, typically a probe having a segment of complementarity of length x does not contain more than x-2 interrogation positions. Since probes are typically 9-21 nucleotides, and usually all of a probe is complementary, a probe typically has 1-19 interrogation positions. Often the probes contain a single interrogation position, at or near the center of probe.

Figure 2:
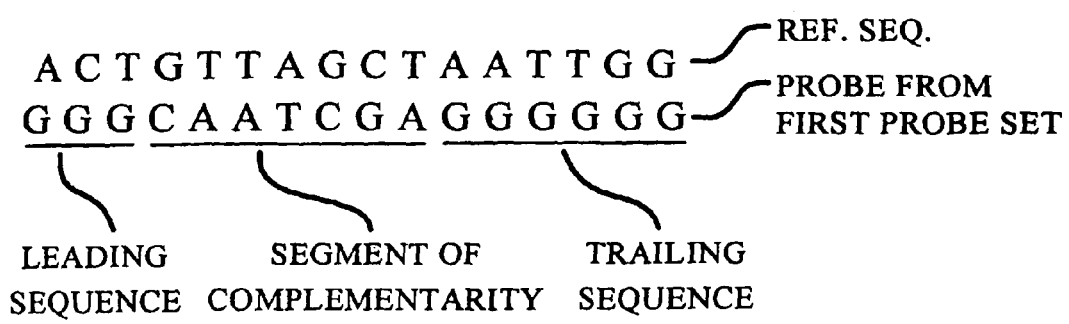
FIG. 2: Segment of complimentarily in a probe from the first probe set (SEQ ID NOS:1 and 2).

For each probe in the first set, there are, for purposes of the present illustration, up to three corresponding probes from three additional probe sets. See FIG. 1. Thus, there are four probes corresponding to each nucleotide of interest in the reference sequence. Each of the four corresponding probes has an interrogation position aligned with that nucleotide of interest. Usually, the probes from the three additional probe sets are identical to the corresponding probe from the first probe set with one exception. The exception is that at least one (and often only one) interrogation position, which occurs in the same position in each of the four corresponding probes from the four probe sets, is occupied by a different nucleotide in the four probe sets. For example, for an A nucleotide in the reference sequence, the corresponding probe from the first probe set has its interrogation position occupied by a T, and the corresponding probes from the additional three probe sets have their respective interrogation positions occupied by A, C, or G, a different nucleotide in each probe. Of course, if a probe from the first probe set comprises trailing or flanking sequences lacking complementarity to the reference sequences (see FIG. 2), these sequences need not be present in corresponding probes from the three additional sets. Likewise corresponding probes from the three additional sets can contain leading or trailing sequences outside the segment of complementarity that are not present in the corresponding probe from the first probe set. Occasionally, the probes from the additional three probe set are identical (with the exception of interrogation position(s)) to a contiguous subsequence of the full complementary segment of the corresponding probe from the first probe set. In this case, the subsequence includes the interrogation position and usually differs from the full-length probe only in the omission of one or both terminal nucleotides from the termini of a segment of complementarity. That is, if a probe from the first probe set has a segment of complementarity of length n, is corresponding probes from the other sets will usually include a subsequence of the segment of at least length n-2. Thus, the subsequence is usually at least 3, 4, 7, 9, 15, 21, or 25 nucleotides long, most typically, in the range of 9-21 nucleotides. The subsequence should be sufficiently long to allow a probe to hybridize detectably more strongly to a variant of the reference sequence mutated at the interrogation position than to the reference sequence.

The probes can be oligodeoxyribonucleotides or oligoribonucleotides, or any modified forms of these polymers that are capable of hybridizing with a target nucleic sequence by complementary base-pairing. Complementary base pairing means sequence-specific base pairing which includes e.g., Watson-Crick base pairing as well as other forms of base pairing such as Hoogsteen base pairing. Modified forms include 2'-O-methyl oligoribonucleotides and so-called PNAs, in which oligodeoxyribonucleotides are linked via peptide bonds rather than phophodiester bonds. The probes can be attached by any linkage to a support (e.g., 3', 5' or via the base). 3' attachment is more usual as this orientation is compatible with the preferred chemistry for solid phase synthesis of oligonucleotides.

The number of probes in the first probe set (and as a consequence the number of probes in additional probe sets) depends on the length of the reference sequence, the number of nucleotides of interest in the reference sequence and the number of interrogation positions per probe. In general, each nucleotide of interest in the reference sequence requires the same interrogation position in the four sets of probes. Consider, as an example, a reference sequence of 100 nucleotides, 50 of which are of interest, and probes each having a single interrogation position. In this situation, the first probe set requires fifty probes, each having one interrogation position corresponding to a nucleotide of interest in the reference sequence. The second, third and fourth probe sets each have a corresponding probe for each probe in the first probe set, and so each also contains a total of fifty probes. The identity of each nucleotide of interest in the reference sequence is determined by comparing the relative hybridization signals at four probes having interrogation positions corresponding to that nucleotide from the four probe sets.

In some reference sequences, every nucleotide is of interest. In other reference sequences, only certain portions in which variants (e.g., mutations or polymorphisms) are concentrated are of interest. In other reference sequences only particular mutations or polymorphisms and immediately adjacent nucleotides are of interest. Usually, the first probe set has interrogation positions selected to correspond to at least a nucleotide (e.g., representing a point mutation) and one immediately adjacent nucleotide. Usually, the probes in the first set have interrogation positions corresponding to at least 3, 10, 50, 100, 1000, or 20,000 contiguous nucleotides. The probes usually have interrogation positions corresponding to at least 5, 10, 30, 50, 75, 90, 99 or sometimes 100% of the nucleotides in a reference sequence. Frequently, the probes in the first probe set completely span the reference sequence and overlap with one another relative to the reference sequence. For example, in one common arrangement each probe in the first probe set differs from another probe in that set by the omission of a 3' base complementary to the reference sequence and the acquisition of a 5' base complementary to the reference sequence. See FIG. 3A.

The number of probes on the chip can be quite large (e.g., $10^5$-$10^6$). However, often only a relatively small proportion (i.e., less than about 50%, 25%, 10%, 5% or 1%) of the total number of probes of a given length are selected to pursue a particular tiling strategy. For example, a complete set of octomer probes comprises 65,536 probes; thus, an array of the invention typically has fewer than 32,768 octomer probes. A complete array of decamer probes comprises 1,048,576 probes; thus, an array of the invention typically has fewer than about 500,000 decamer probes. Often arrays have a lower limit of 25, 50 or 100 probes and an upper limit of 1,000,000, 100,000, 10,000 or 1000 probes. The arrays can have other components besides the probes such as linkers attaching the probes to a support.

Some advantages of the use of only a proportion of all possible probes of a given length include: (i) each position in the array is highly informative, whether or not hybridization occurs; (ii) nonspecific hybridization is minimized; (iii) it is straightforward to correlate hybridization differences with sequence differences, particularly with reference to the hybridization pattern of a known standard; and (iv) the ability to address each probe independently during synthesis, using high resolution photolithography, allows the array to be designed and optimized for any sequence. For example the length of any probe can be varied independently of the others.

Figure 3A:
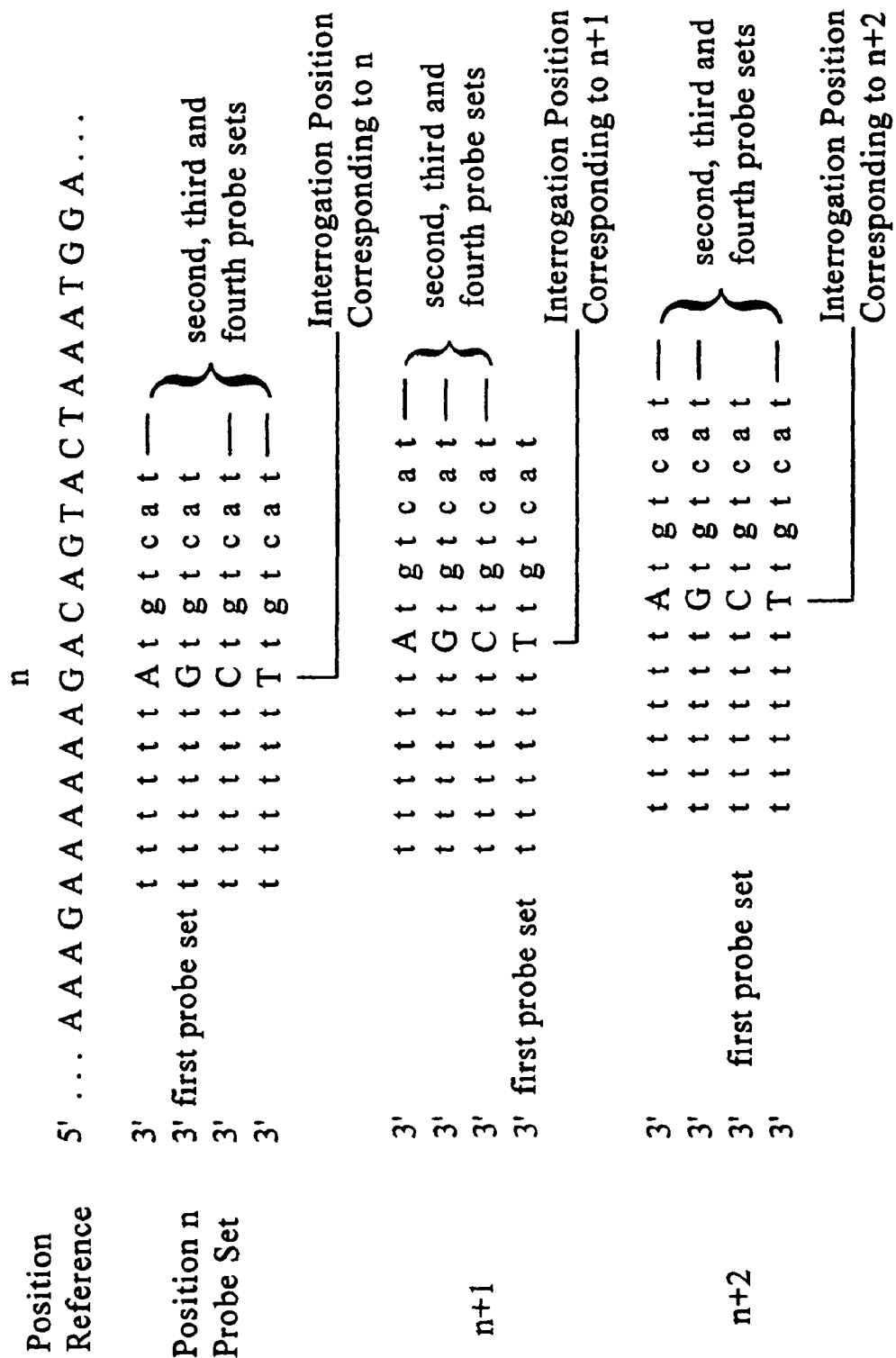
FIG. 3A (SEQ ID NOS:3-7): Incremental succession of probes in a basic tiling strategy. The figure shows four probe sets, each having three probes. Note that each probe differs from its predecessor in the same set by the acquisition of a 5' nucleotide and the loss of a 3' nucleotide, as well as in the nucleotide occupying the interrogation position.
Figure 5:
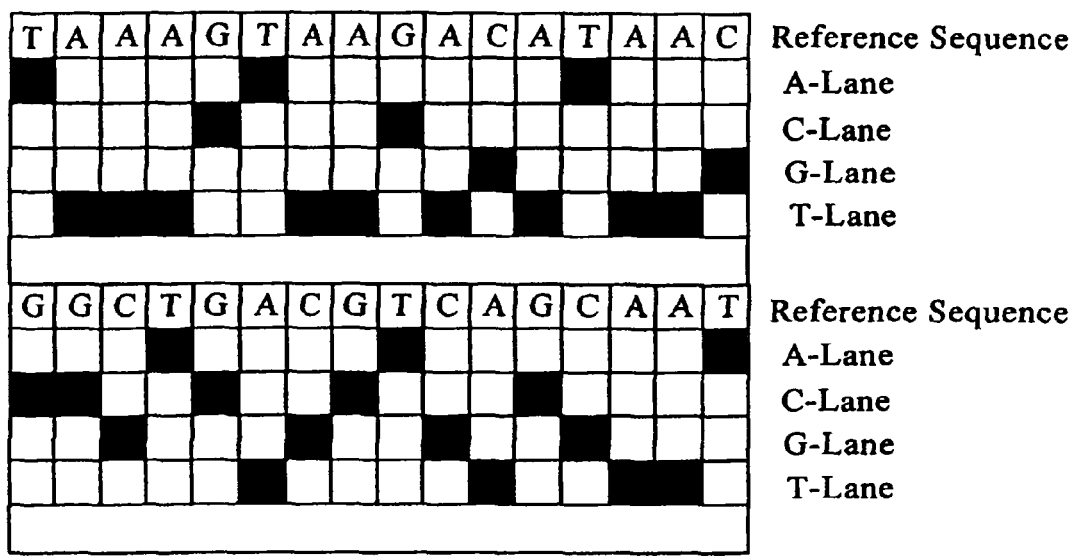
FIG. 5 (SEQ ID NOS:19-20): Hybridization pattern of chip having probes laid down in lanes. Dark patches indicate hybridization. The probes in the lower part of the figure occur at the column of the array indicated by the arrow when the probes length is 15 and the interrogation position 7.

For conceptual simplicity, the probes in a set are usually arranged in order of the sequence in a lane across the chip. A lane contains a series of overlapping probes, which represent or tile across, the selected reference sequence (see FIG. 3A). The components of the four sets of probes are usually laid down in four parallel lanes, collectively constituting a row in the horizontal direction and a series of 4-member columns in the vertical direction. Corresponding probes from the four probe sets (i.e., complementary to the same subsequence of the reference sequence) occupy a column. Each probe in a lane usually differs from its predecessor in the lane by the omission of a base at one end and the inclusion of additional base at the other end as shown in FIG. 3A. However, this orderly progression of probes can be interrupted by the inclusion of control probes or omission of probes in certain columns of the array. Such columns serve as controls to orient the chip, or gauge the background, which can include target sequence nonspecifically bound to the chip.

The probes sets are usually laid down in lanes such that all probes having an interrogation position occupied by an A form an A-lane, all probes having an interrogation position occupied by a C form a C-lane, all probes having an interrogation position occupied by a G form a G-lane, and all probes having an interrogation position occupied by a T (or U) form a T lane (or a U lane). Note that in this arrangement there is not a unique correspondence between probe sets and lanes. Thus, the probe from the first probe set is laid down in the A-lane, C-lane, A-lane, A-lane and T-lane for the five columns in FIG. 4A. The interrogation position on a column of probes corresponds to the position in the target sequence whose identity is determined from analysis of hybridization to the probes in that column. Thus, $I_1$-$I_5$ respectively correspond to $N_1$-$N_5$ in FIG. 4A. The interrogation position an be anywhere in a probe but is usually at or near the central position of the probe to maximize differential hybridization signals between a perfect match and a single-base mismatch. For example, for an 11 mer probe, the central position is the sixth nucleotide.

Although the array of probes is usually laid down in rows and columns as described above, such a physical arrangement of probes on the chip is not essential. Provided that the spatial location of each probe in an array is known, the data from the probes can be collected and processed to yield the sequence of a target irrespective of the physical arrangement of the probes on a chip. In processing the data, the hybridization signals from the respective probes can be reasserted into any conceptual array desired for subsequent data reduction whatever the physical arrangement; of probes on the chip.

A range of lengths of probes can be employed in the chips. As noted above, a probe may consist exclusively of a complementary segments, or may have one or more complementary segments juxtaposed by flanking, trailing and/or intervening segments. In the latter situation, the total length of complementary segment(s) is more important that the length of the probe. In functional terms, the complementary segment(s) of the first probe sets should be sufficiently long to allow the probe to hybridize detectably more strongly to a reference sequence compared with a variant of the reference including a single base mutation at the nucleotide corresponding to the interrogation position of the probe. Similarly, the complementary segment(s) in corresponding probes from additional probe sets should be sufficiently long to allow a probe to hybridize detectably more strongly to a variant of the reference sequence having a single nucleotide substitution at the interrogation position relative to the reference sequence. A probe usually has a single complementary segment having a length of at least 3 nucleotides, and more usually at least 5, 6, 7, 8, 9, 10, 11, 12, 13, 14, 15, 16, 17, 18, 19, 20, 21, 22, 23, 24, 25 or 30 bases exhibiting perfect complementarity (other than possibly at the interrogation position(s) depending on the probe set) to the reference sequence. In bridging strategies, where more than one segment of complementarity is present, each segment provides at least three complementary nucleotides to the reference sequence and the combined segments provide at least two segments of three or a total of six complementary nucleotides. As in the other strategies, the combined length of complementary segments is typically from 6-30 nucleotides, and preferably from about 9-21 nucleotides. The two segments are often approximately the same length. Often, the probes (or segment of complementarity within probes) have an odd number of bases, so that an interrogation position can occur in the exact center of the probe.

In some chips, all probes are the same length. Other chips employ different groups of probe sets, in which case the probes are of the same size within a group, but differ between different groups. For example, some chips have one group comprising four sets of probes as described above in which all the probes are 11 mers, together with a second group comprising four sets of probes in which all of the probes are 13 mers. Of course, additional groups of probes can be added. Thus, some chips contain, e.g., four groups of probes having sizes of 11 mers, 13 mers, 15 mers and 17 mers. Other chips have different size probes within the same group of four probe sets. In these chips, the probes in the first set can vary in length independently of each other. Probes in the other sets are usually the same length as the probe occupying the same column from the first set. However, occasionally different lengths of probes can be included at the same column position in the four lanes. The different length probes are included to equalize hybridization signals from probes irrespective of whether A-T or C-G bonds are formed at the interrogation position.

The length of probe can be important in distinguishing between a perfectly matched probe and probes showing a single-base mismatch with the target sequence. The discrimination is usually greater for short probes. Shorter probes are usually also less susceptible to formation of secondary structures. However, the absolute amount of target sequence bound, and hence the signal, is greater for larger probes. The probe length representing the optimum compromise between these competing considerations may vary depending on inter alia the GC content of a particular region of the target DNA sequence, secondary structure, synthesis efficiency and cross-hybridization. In some regions of the target, depending on hybridization conditions, short probes (e.g., 11 mers) may provide information that is inaccessible from longer probes (e.g., 19. mers) and vice versa. Maximum sequence information can be read by including several groups of different sized probes on the chip as noted above. However, for many regions of the target sequence, such a strategy provides redundant information in that the same sequence is read multiple times from the different groups of probes. Equivalent information can be obtained from a single group of different sized probes in which the sizes are selected to maximize readable sequence at particular regions of the target sequence. The strategy of customizing probe length within a single group of probe sets minimizes the total number of probes required to read a particular target sequence. This leaves ample capacity for the chip to include probes to other reference sequences.

The invention provides an optimization block which allows systematic variation of probe length and interrogation position to optimize the selection of probes for analyzing a particular nucleotide in a reference sequence. The block comprises alternating columns of probes complementary to the wildtype target and probes complementary to a specific mutation. The interrogation position is varied between columns and probe length is varied down a column. Hybridization of the chip to the reference sequence or the mutant form of the reference sequence identifies the probe length and interrogation position providing the greatest differential hybridization signal.

Variation of interrogation position in probes for analyzing different regions of a target sequence offers a number of advantages. If a segment of a target sequence contains two closely spaced mutations, m1, and m2, and probes for analyzing that segment have an interrogation position at or near the middle, then no probe has an interrogation position aligned with one of the mutations without overlapping the other mutation (see first probe in FIG. 4B) Thus, the presence of a mutation would have to be detected by comparing the hybridization signal of a single-mismatched probe with a double-mismatched probe. By contrast, if the interrogation position is near the 3' end of the probes, probes can have their interrogation position aligned with m1 without overlapping m2 (second probe in FIG. 4B). Thus, the mutation can be detected by a comparison of a perfectly matched probe with single based mismatched probes,. Similarly, if the interrogation position is near the 5' end of the probes, probes can have their interrogation position aligned with m2 without overlapping m1 (third probe in FIG. 4B).

Variation of the interrogation position also offers the advantage of reducing loss of signal due to self-annealing of certain probes. FIG. 4C shows a target sequence having a nucleotide X, which can be read either from the relative signals of the four probes having a central interrogation position (shown at the left of the figure) or from the four probes having the interrogation position near the three prime end (shown at the right of the figure). Only the probes having the central interrogation position are capable of self-annealing. Thus, a higher signal is obtained from the probes having the interrogation position near the terminus.

The probes are designed to be complementary to either strand of the reference sequence (e.g., coding or non-coding). Some chips contain separate groups of probes, one complementary to the coding strand, the other complementary to the noncoding strand. Independent analysis of coding and noncoding strands provides largely redundant information. However, the regions of ambiguity in reading the coding strand are not always the same as those in reading the noncoding strand. Thus, combination of the information from coding and noncoding strands increases the overall accuracy of sequencing.

Some chips contain additional probes or groups of probes designed to be complementary to a second reference sequence. The second reference sequence is often a subsequence of the first reference sequence bearing one or more commonly occurring mutations or interstrain variations. The second group of probes is designed by the same principles as described above except that the probes exhibit complementarity to the second reference sequence. The inclusion of a second group is particular useful for analyzing short subsequences of the primary reference sequence in which multiple mutations are expected to occur within a short distance commensurate with the length of the probes (i.e., two or more mutations within 9 to 21 bases). Of course, the same principle can be extended to provide chips containing groups of probes for any number of reference sequences. Alternatively, the chips may contain additional probe(s) that do not form part of a tiled array as noted above, but rather serves as probe(s) for a conventional reverse dot blot. For example, the presence of mutation can be detected from binding of a target sequence to a single oligomeric probe harboring the mutation. Preferably, an additional probe containing the equivalent region of the wildtype sequence is included as a control.

Although only a subset of probes is required to analyze a particular target sequence, it is quite possible that other probes superfluous to the contemplated analysis are also included on the chip. In the extreme case, the chip could can a complete set of all probes of a given length notwithstanding that only a small subset is required to analyze the particular reference sequence of interest. Although such a situation might appear wasteful of resources, a chip including a complete set of probes offers the advantage of including the appropriate subset of probes for analyzing any reference sequence. Such a chip also allows simultaneous analysis of a reference sequence from different subsets of probes (e.g., subsets having the interrogation site at different positions in the probe).

In its simplest terms, the analysis of a chip reveals whether the target sequence is the same or different from the reference sequence. If the two are the same, all probes in the first probe set show a stronger hybridization signal than corresponding probes from other probe sets. If the two are different, most probes from the first probe set still show a stronger hybridization signal than corresponding probes from the other probe sets, but some probes from the first probe set do not. Thus, when a probe from another probe sets light up more strongly than the corresponding probe from the first probe set, this provides a simple visual indication that the target sequence and reference sequence differ.

Figure 6:
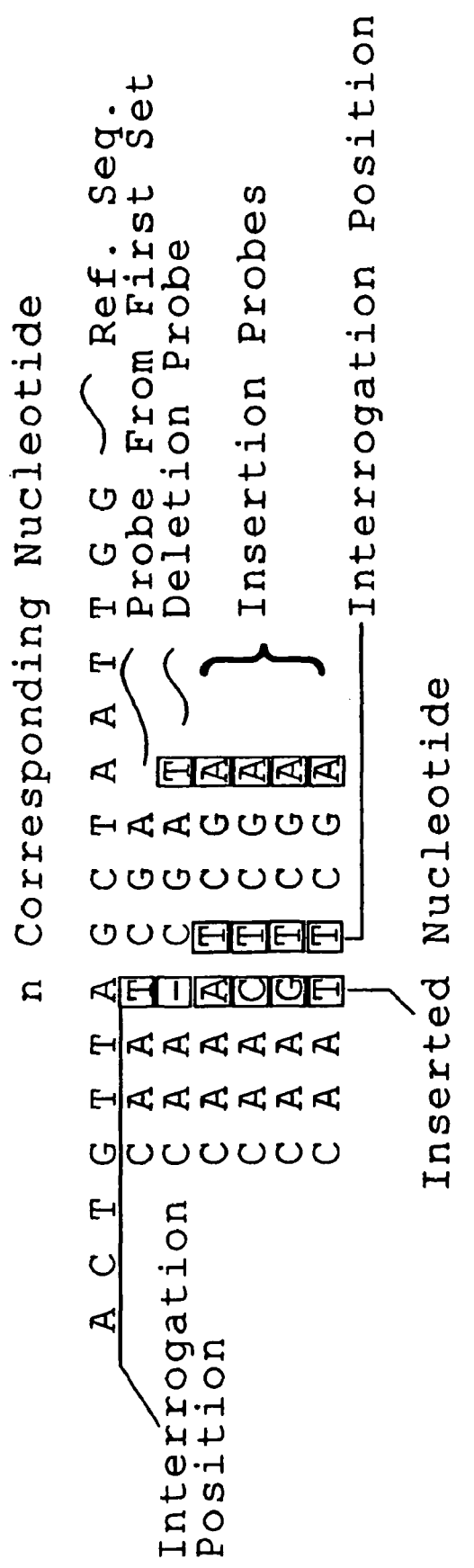
FIG. 6 (SEQ ID NO:1): Strategies for detecting deletion and insertion mutations. Bases in brackets may or may not be present.

The chips also reveal the nature and position of differences between the target and reference sequence. The chips are read by comparing the intensities of labelled target bound to the probes in an array. Specifically, for each nucleotide of interest in the target sequence, a comparison is performed between probes having an interrogation position aligned with that position. These probes form a column (actual or conceptual) on the chip. For example, a column often contains one probe from each of A, C, G and T lanes. The nucleotide in the target sequence is identified as the complement of the nucleotide occupying the interrogation position in the probe showing the highest hybridization signal from a column. FIG. 6 shows the hybridization pattern of a chip hybridized to its reference sequence. The dark square in each column represents the probe from the column having the highest hybridization signal. The sequence can be read by following the pattern of dark squares from left to right across the chip. The first dark square is in the A lane indicating that the nucleotide occupying the interrogation position of the probe represented by this square is an A. The first nucleotide in the reference sequence is the complement of nucleotide occupying the interrogation position of this probe (i.e., a T). Similarly, the second dark square is in the T-lane, from which it can be deduced that the second nucleotide in the reference sequence is an A. Likewise the third dark square is in the T-lane, from which it can be deduced that the third nucleotide in the reference sequence is also an A, and so forth. By including probes in the first probe set (and by implication in the other probe sets) with interrogation positions corresponding to every nucleotide in a reference sequence, it is possible to read substantially every nucleotide in a target sequence, thereby revealing the complete or nearly complete sequence of the target.

Of the four probes in a column, only one can exhibit a perfect match to the target sequence whereas the others usually exhibit at least a one base pair mismatch. The probe exhibiting a perfect match usually produces a substantially greater hybridization signal than the other three probes in the column and is thereby easily identified. However, in some regions of the target sequence, the distinction between a perfect match and a one-base mismatch is less clear. Thus, a call ratio is established to define the ratio of signal from the best hybridizing probes to the second best hybridizing probe that must be exceeded for a particular target position to be read from the probes. A high call ratio ensures that few if any errors are made in calling target nucleotides, but can result in some nucleotides being scored as ambiguous, which could in fact be accurately read. A lower call ratio results in fewer ambiguous calls, but can result in more erroneous calls. It has been found that at a call ratio of 1.2. virtually all calls are accurate. However, a small but significant number of bases (e.g., up to about 10%) may have to be scored as ambiguous.

Although small regions of the target sequence can sometimes be ambiguous, these regions usually occur at the same or similar segments in different target sequences. Thus, for precharacterized mutations, it is known in advance whether that mutation is likely to occur within a region of unambiguously determinable sequence.

An array of probes is most useful for analyzing the reference sequence from which the probes were designed and variants of that sequence exhibiting substantial sequence similarity with the reference sequence (e.g., several single-base mutants spaced over the reference sequence). When an array is used to analyze the exact reference sequence from which it was designed, one probe exhibits a perfect match to the reference sequence, and the other three probes in the same column exhibits single-base mismatches. Thus, discrimination between hybridization signals is usually high and accurate sequence is obtained. High accuracy is also obtained when an array is used for analyzing a target sequence comprising a variant of the reference sequence that has a single mutation relative to the reference sequence, or several widely spaced mutations relative to the reference sequence. At different mutant loci, one probe exhibits a perfect match to the target, and the other three probes occupying the same column exhibit single-base mismatches, the difference (with respect to analysis of the reference sequence) being the lane in which the perfect match occurs.

For target sequences showing a high degree of divergence from the reference strain or incorporating several closely spaced mutations from the reference strain, a single group of probes (i.e., designed with respect to a single reference sequence) will not always provide accurate sequence for the highly variant region of this sequence. At some particular columnar positions, it may be that no single probe exhibits perfect complementarity to the target and that any comparison must be based on different degrees of mismatch between the four probes. Such a comparison does not always allow the target nucleotide corresponding to that columnar position to be called. Deletions in target sequences can be detected by loss of signal from probes having interrogation positions encompassed by the deletion. However, signal may also be lost from probes having interrogation positions closely proximal to the deletion resulting in some regions of the target sequence that cannot be read. Target sequence bearing insertions will also exhibit short regions including and proximal to the insertion that usually cannot be read.

The presence of short regions of difficult-to-read target because of closely spaced mutations, insertions or deletions, does not prevent determination of the remaining sequence of the target as different regions of a target sequence are determined independently. Moreover, such ambiguities as might result from analysis of diverse variants with a single group of probes can be avoided by including multiple groups of probe sets on a chip. For example, one group of probes can be designed based on a full-length reference sequence, and the other groups on subsequences of the reference sequence incorporating frequently occurring mutations or strain variations.

A particular advantage of the present sequencing strategy over conventional sequencing methods is the capacity simultaneously to detect and quantify proportions of multiple target sequences. Such capacity is valuable, e.g., for diagnosis of patients who are heterozygous with respect to a gene or who are infected with a virus, such as HIV, which is usually present in several polymorphic forms. Such capacity is also useful in analyzing targets from biopsies of tumor cells and surrounding tissues. The presence of multiple target sequences is detected from the relative signals of the four probes at the array columns corresponding to the target nucleotides at which diversity occurs. The relative signals of the four probes for the mixture under test are compared with the corresponding signals from a homogeneous reference sequence. An increase in a signal from a probe that is mismatched with respect to the reference sequence, and a corresponding decrease in the signal from the probe which is matched with the reference sequence, signal the presence of a mutant strain in the mixture. The extent in shift in hybridization signals of the probes is related to the proportion of a target sequence in the mixture. Shifts in relative hybridization signals can be quantitatively related to proportions of reference and mutant sequence by prior calibration of the chip with seeded mixtures of the mutant and reference sequences. By this means, a chip can be used to detect variant or mutant strains constituting as little as 1, 5, 20, or 25% of a mixture of stains.

Similar principles allow the simultaneous analysis of multiple target sequences even when none is identical to the reference sequence. For example, with a mixture of two target sequences bearing first and second mutations, there would be a variation in the hybridization patterns of probes having interrogation positions corresponding to the first and second mutations relative to the hybridization pattern with the reference sequence. At each position, one of the probes having a mismatched interrogation position relative to the reference sequence would show an increase in hybridization signal, and the probe having a matched interrogation position relative to the reference sequence would show a decrease in hybridization signal. Analysis of the hybridization pattern of the mixture of mutant target sequences, preferably in comparison with the hybridization pattern of the reference sequence, indicates the presence of two mutant target sequences, the position and nature of the mutation in each strain, and the relative proportions of each strain.

In a variation of the above method, several target sequences target sequences are differentially labelled before being simultaneously applied to the array. For example, each different target sequence can be labelled with a fluorescent labels emitting at different wavelength. After applying a mixtures of target sequence to the arrays, the individual target sequences can be distinguished and independently analyzed by virtue of the differential labels. For example, the methods target sequences obtained from a patient at different stages of a disease can be differently labelled and analyzed simultaneously, facilitating identification of new mutations.

2. Omission of Probes

The basic strategy outlined above employs four probes to read each nucleotide of interest in a target sequence. One probe (from the first probe set) shows a perfect match to the reference sequence and the other three probes (from the second, third and fourth probe sets) exhibit a mismatch with the reference sequence and a perfect match with a target sequence bearing a mutation at the nucleotide of interest. The provision of three probes from the second, third and fourth probe sets allows detection of each of the three possible nucleotide substitutions of any nucleotide of interest. However, in some reference sequences or regions of reference sequences, it is known in advance that only certain mutations are likely to occur. Thus, for example, at one site it might be known that an A nucleotide in the reference sequence may exist as a T mutant in some target sequences but is unlikely to exist as a C or G mutant. Accordingly, for analysis of this region of the reference sequence, one might include only the first and second probe sets, the first probe set exhibiting perfect complementarity to the reference sequence, and the second probe set having an interrogation position occupied by an invariant A residue (for detecting the T mutant). In other situations, one might include the first, second and third probes sets (but not the fourth) for detection of a wildtype nucleotide in the reference sequence and two mutant variants thereof in target sequences. In some chips, probes that would detect silent mutations (i.e., not affecting amino acid sequence) are omitted.

Some chips effectively contain the second, third and optionally, the fourth probes sets described in the basic tiling strategy (i.e., the mismatched probe sets) but omit some or all of the probes from the first probe set (i.e., perfectly matched probes). Therefore, such chips comprise at least two probe sets, which will arbitrarily be referred to as probe sets A and B (to avoid confusion with the nomenclature used to describe the four probe sets in the basic tiling strategy). Probe set A has a plurality of probes. Each probe comprises a segment exactly complementary to a subsequence of a reference sequence except in at least one interrogation position. The interrogation position corresponds to a nucleotide in the reference sequence juxtaposed with the interrogation position when the reference sequence and probe are maximally aligned. Probe set B has a corresponding probe for each probe in the first probe set. The corresponding probe in probe set B is identical to a sequence comprising the corresponding probe from the first probe set or a subsequence thereof that includes the at least one (and usually only one) interrogation position except that the at least one interrogation position is occupied by a different nucleotide in each of the two corresponding probes from the probe sets A and B. An additional probe set C, if present, also comprises a corresponding probe for each probe in the probe set A except in the at least one interrogation position, which differs in the corresponding probes from probe sets A, B and C. The arrangement of probe sets A, B and C is shown in FIG. 3B. FIG. 3B is the same as FIG. 3A except that the first probe set has been omitted and the second, third and fourth probe sets in FIG. 3A have been relabelled as probe sets A, B and C in FIG. 3B.

Chips lacking perfectly matched probes are preferably analyzed by hybridization to both target and reference sequences. The hybridizations can be performed sequentially, or, if the target and reference are differentially labelled, concurrently. The hybridization data are then analyzed in two ways. First, considering only the hybridization signals of the probes to the target sequence, one compares the signals of corresponding probes for each position of interest in the target sequence. For a position of mismatch with the reference sequence, one of the probes having an interrogation position aligned with that position in the target sequence shows a substantially higher signal than other corresponding probes. The nucleotide occupying the position of mismatch in the target sequence is the complement of the nucleotide occupying the interrogation position of the corresponding probe showing the highest signal. For a position where target and reference sequence are the same, none of the corresponding probes having an interrogation position aligned with that position in the target sequence is matched, and corresponding probes generally show weak signals, which may vary somewhat from each other.

In a second level of analysis, the ratio of hybridization signals to the target and reference sequences is determined for each probe in the array. For most probes in the array the ratio of hybridization signals is about the same. For such a probe, it can be deduced that the interrogation position of the probe corresponds to a nucleotide that is the same in target and reference sequences. A few probes show a much higher ratio of target hybridization to reference hybridization than the majority of probes. For such a probe, it can be deduced that the interrogation position of the probe corresponds to a nucleotide that differs between target and reference sequences, and that in the target, this nucleotide is the complement of the nucleotide occupying the interrogation position of the probe. The second level of analysis serves as a control to confirm the identification of differences between target and reference sequence from the first level of analysis.

3. Wildtype Probe Lane

When the chips comprise four probe sets, as discussed supra, and the probe sets are laid down in four lanes, an A lane, a C-lane, a G lane and a T or U lane, the probe having a segment exhibiting perfect complementarity to a reference sequence varies between the four lanes from one column to another. This does not present any significant difficulty in computer analysis of the data from the chip. However, visual inspection of the hybridization pattern of the chip is sometimes facilitated by provision of an extra lane of probes, in which each probe has a segment exhibiting perfect complementarity to the reference sequence. See FIG. 4A. This extra lane of probes is called the wildtype lane and contains only probes from the first probe set. Each wildtype lane probe has a segment that is identical to a segment from one of the probes in the other four lanes (which lane depending on the column position). The wildtype lane hybridizes to a target sequence at all nucleotide positions except those in which deviations from the reference sequence occurs. The hybridization pattern of the wildtype lane thereby provides a simple visual indication of mutations.

4. Deletion, Insertion and Multiple-Mutation Probes

Some chips provide an additional probe set specifically designed for analyzing deletion mutations. The additional probe set comprises a probe corresponding to each probe in the first probe set as described above. However, a probe from the additional probe set differs from the corresponding probe in the first probe set in that the nucleotide occupying the interrogation position is deleted in the probe from the additional probe set. See FIG. 6 optionally, the probe from the additional probe set bears an additional nucleotide at one of its termini relative to the corresponding probe from the first probe set (shown in brackets in FIG. 6). The probe from the additional probe set will hybridize more strongly than the corresponding probe from the first probe set to a target sequence having a single base deletion at the nucleotide corresponding to the interrogation position. Additional probe sets are provided in which not only the interrogation position, but also an adjacent nucleotide is deleted.

Similarly, other chips provide additional probe sets for analyzing insertions. For example, one additional probe set has a probe corresponding to each probe in the first probe set as described above. However, the probe in the additional probe set has an extra T nucleotide inserted adjacent to the interrogation position. See FIG. 6 (the extra T is shown in a square box). Optionally, the probe has one fewer nucleotide at one of its termini relative to the corresponding probe from the first probe set (shown in brackets). The probe from the additional probe set hybridizes more strongly than the corresponding probe from the first probe set to a target sequence having an A insertion to the left of nucleotide in the reference sequence in FIG. 6. Similar additional probe sets can be constructed having C, G or A nucleotides inserted adjacent to the interrogation position.

Usually, four such additional probe sets, one for each nucleotide, are used in combination. Comparison of the hybridization signal of the probes from the additional probe sets with the corresponding probe from the first probe set indicates whether the target sequence contains and insertion. For example, if a probe from one of the additional probe sets shows a higher hybridization signal than a corresponding probe from the first probe set, it is deduced that the target sequence contains an insertion adjacent to the corresponding nucleotide (n) in the target sequence. The inserted base in the target is the complement of the inserted base in the probe from the additional probe set showing the highest hybridization signal. If the corresponding probe from the first probe set shows a higher hybridization signal than the corresponding probes from the additional probe sets, then the target sequence does not contain an insertion to the left of corresponding position (("n" in FIG. 6)) in the target sequence.

Other chips provide additional probes (multiple-mutation probes) for analyzing target sequences having multiple closely spaced mutations. A multiple-mutation probe is usually identical to a corresponding probe from the first set as described above, except in the base occupying the interrogation position, and except at one or more additional positions, corresponding to nucleotides in which substitution may occur in the reference sequence. The one or more additional positions in the multiple mutation probe are occupied by nucleotides complementary to the nucleotides occupying corresponding positions in the reference sequence when the possible substitutions have occurred.

5. Block Tiling

In block tiling, a perfectly matched (or wildtype) probe is compared with multiple sets of mismatched or mutant probes. The perfectly matched probe and the multiple sets of mismatched probes with which it is compared collectively form a group or block of probes on the chip. Each set comprises at least one, and usually, three mismatched probes. FIG. 7 shows a perfectly matched probe (CAATCGA) having three interrogation positions ($I_1$, $I_2$ and $I_3$). The perfectly matched probe is compared with three sets of probes (arbitrarily designated A, B and C), each having three mismatched probes. In set A, the three mismatched probes are identical to a sequence comprising the perfectly matched probe or a subsequence thereof including the interrogation positions, except at the first interrogation position. That is, the mismatched probes in the set A differ from the perfectly matched probe set at the first interrogation position. Thus, the relative hybridization signals of the perfectly matched probe and the mismatched probes in the set A indicates the identity of the nucleotide in a target'sequence corresponding to the first interrogation position. This nucleotide is the complement of the nucleotide occupying the interrogation position of the probe showing the highest signal. Similarly, set B comprises three mismatched probes, that differ from the perfectly matched probe at the second interrogation position. The relative hybridization intensities of the perfectly matched probe and the three mismatched probes of set B reveal the identity of the nucleotide in the target sequence corresponding to the second interrogation position (i.e., n2. in FIG. 7). Similarly, the three mismatched probes in set C in FIG. 7 differ from the perfectly matched probe at the third interrogation position. Comparison of the hybridization intensities of the perfectly matched probe and the mismatched probes in the set C reveals the identity of the nucleotide in the target sequence corresponding to the third interrogation position (n3).

As noted above, a perfectly matched probe may have seven or more interrogation positions. If there are seven interrogation positions, there are seven sets of three mismatched probe, each set serving to identify the nucleotide corresponding to one of the seven interrogation positions. Similarly, if there are 20 interrogation positions in the perfectly matched probe, then 20 sets of three mismatched probes are employed. As in other tiling strategies, selected probes can be omitted if it is known in advance that only certain types of mutations are likely to arise.

Each block of probes allows short regions of a target sequence to be read. For example, for a block of probes having seven interrogation positions, seven nucleotides in the target sequence can be read. Of course, a chip can contain any number of blocks depending on how many nucleotides of the target are of interest. The hybridization signals for each block can be analyzed independently of any other block. The block tiling strategy can also be combined with other tiling strategies, with different parts of the same reference sequence being tiled by different strategies.

The block tiling strategy is a species of the basic tiling strategy discussed above, in which the probe from the first probe set has more than one interrogation position. The perfectly matched probe in the block tiling strategy is equivalent to a probe from the first probe set in the basic tiling strategy. The three mismatched probes in set A in block tiling are equivalent to probes from the second, third and fourth probe sets in the basic tiling strategy. The three mismatched probes in set B of block tiling are equivalent to probes from additional probe sets in basic tiling arbitrarily designated the fifth, sixth and seventh probe sets. The three mismatched probes in set C of blocking tiling are equivalent to probes from three further probe sets in basic tiling arbitrarily designated the eighth, ninth and tenth probe sets.

The block tiling strategy offers two advantages over a basic strategy in which each probe in the first set has a single interrogation position. One advantage is that the same sequence information can be obtained from fewer probes. A second advantage is that each of the probes constituting a block (i.e., a probe from the first probe set and a corresponding probe from each of the other probe sets) can have identical 3' and 5' sequences, with the variation confined to a central segment containing the interrogation positions. The identity of 3' sequence between different probes simplifies the strategy for solid phase synthesis of the probes on the chip and results in more uniform deposition of the different probes on the chip, thereby in turn increasing the uniformity of signal to noise ratio for different regions of the chip.

6. Multiplex Tiling

In the block tiling strategy discussed above, the identity of a nucleotide in a target or reference sequence is determined by comparison of hybridization patterns of one probe having a segment showing a perfect match with that of other probes (usually three other probes) showing a single base mismatch. In multiplex tiling, the identity of at least two nucleotides in a reference or target sequence is determined by comparison of hybridization signal intensities of four probes, two of which have a segment showing perfect complementarity or a single base mismatch to the reference sequence, and two of which have a segment showing perfect complementarity or a double-base mismatch to a segment. The four probes whose hybridization patterns are to be compared each have a segment that is exactly complementary to a reference sequence except at two interrogation positions, in which the segment may or may not be complementary to the reference sequence. The interrogation positions correspond to the nucleotides in a reference or target sequence which are determined by the comparison of intensities. The nucleotides occupying the interrogation positions in the four probes are selected according to the following rule. The first interrogation position is occupied by a different nucleotide in each of the four probes. The second interrogation position is also occupied by a different nucleotide in each of the four probes. In two of the four probes, designated the first and second probes, the segment is exactly complementary to the reference sequence except at not more than one of the two interrogation positions. In other words, one of the interrogation positions is occupied by a nucleotide that is complementary to the corresponding nucleotide from the reference sequence and the other interrogation position may or may not be so occupied. In the other two of the four probes, designated the third and fourth probes, the segment is exactly complementary to the reference sequence except that both interrogation positions are occupied by nucleotides which are noncomplementary to the respective corresponding nucleotides in the reference sequence.

There are number of ways of satisfying these conditions depending on whether the two nucleotides in the reference sequence corresponding to the two interrogation positions are the same or different. If these two nucleotides are different in the reference sequence (probability 3/4), the conditions are satisfied by each of the two interrogation positions being occupied by the same nucleotide in any given probe. For example, in the first probe, the two interrogation positions would both be A, in the second probe, both would be C, in the third probe, each would be G, and in the fourth probe each would be T or U. If the two nucleotides in the reference sequence corresponding to the two interrogation positions are different, the conditions noted above are satisfied by each of the interrogation positions in any one of the four probes being occupied by complementary nucleotides. For example, in the first probe, the-interrogation positions could be occupied by A and T, in the second probe by C and G, in the third probe by G and C, and in the four probe, by T and A. See (FIG. 8).

When the four probes are hybridized to a target that is the same as the reference sequence or differs from the reference sequence at one (but not both) of the interrogation positions, two of the four probes show a double-mismatch with the target and two probes show a single mismatch. The identity of probes showing these different degrees of mismatch can be determined from the different hybridization signals. From the identity of the probes showing the different degrees of mismatch, the nucleotides occupying both of the interrogation positions in the target sequence can be deduced.

For ease of illustration, the multiplex strategy has been initially described for the situation where there are two nucleotides of interest in a reference sequence and only four probes in an array. Of course, the strategy can be extended to analyze any number of nucleotides in a target sequence by using additional probes. In one variation, each pair of interrogation positions is read from a unique group of four probes. In a block variation, different groups of four probes exhibit the same segment of complementarity with the reference sequence, but the interrogation positions move within a block. The block and standard multiplex tiling variants can of course be used in combination for different regions of a reference sequence. Either or both variants can also be used in combination with any of the other tiling strategies described.

7. Helper Mutations

Occasionally, small regions of a reference sequence give a low hybridization signal as a result of annealing of probes. The self-annealing reduces the amount of probe effectively available for hybridizing to the target. Although such regions of the target are generally small and the reduction of hybridization signal is usually not so substantial as to obscure the sequence of this region, this concern can be avoided by the use of probes incorporating helper mutations. A helper mutation refers to a position of mismatch in a probe other than at an interrogation position. The helper mutation(s) serve to break-up regions of internal complementarity within a probe and thereby prevent annealing. Usually, one or two helper mutations are quite sufficient for this purpose. The inclusion of helper mutations can be beneficial in any of the tiling strategies noted above. In general each probe having a particular interrogation position has the same helper mutation(s). Thus, such probes have a segment in common which shows perfect complementarity with a reference sequence, except that the segment contains at least one helper mutation (the same in each of the probes) and at least one interrogation position (different in all of the probes). For example, in the basic tiling strategy, a probe from the first probe set comprises a segment containing an interrogation position and showing perfect complementarity with a reference sequence except for one or two helper mutations. The corresponding probes from the second, third and fourth probe sets usually comprise the same segment (or sometimes a subsequence thereof including the helper mutation(s) and interrogation position), except that the base occupying the interrogation position varies in each probe. See FIG. 9.

Usually, the helper mutation tiling strategy is used in conjunction with one of the tiling strategies described above. The probes containing helper mutations are used to tile regions of a reference sequence otherwise giving low hybridization signal (e.g., because of self-complementarity), and the alternative tiling strategy is used to tile intervening regions.

8. Pooling Strategies

Pooling strategies also employ arrays of immobilized probes. Probes are immobilized in cells of an array, and the hybridization signal of each cell can be determined independently of any other cell. A particular cell may be occupied by pooled mixture of probes. Although the identity of each probe in the mixture is known, the individual probes in the pool are not separately addressable. Thus, the hybridization signal from a cell is the aggregate of that of the different probes occupying the cell. In general, a cell is scored as hybridizing to a target sequence if at least one probe occupying the cell comprises a segment exhibiting perfect complementarity to the target sequence.

A simple strategy to show the increased power of pooled strategies over a standard tiling is to create three cells each containing a pooled probe having a single pooled position, the pooled position being the same in each of the pooled probes. At the pooled position, there are two possible nucleotide, allowing the pooled probe to hybridize to two target sequences. In tiling terminology, the pooled position of each probe is an interrogation position. As will become apparent, comparison of the hybridization intensities of the pooled probes from the three cells reveals the identity of the nucleotide in the target sequence corresponding to the interrogation position (i.e., that is matched with the interrogation position when the target sequence and pooled probes are maximally aligned for complementarity).

The three cells are assigned probe pools that are perfectly complementary to the target except as the pooled position, which is occupied by a different pooled nucleotide in each probe as follows (SEQ ID NOS:23-30, 25 and 28, respectively):

```
[AC] = M, [GT] = K, [AG] = R
as substitutions in the probe
IUPAC standard ambiguity notation)

X - interrogation position
Target: TAACCACTCACGGGAGCA

Pool 1: ATTGGMGAGTGCCC
       =ATTGGaGAGTGCCC    (complement to mutant
                           't')
       +ATTGGcGAGTGCCC    (complement to mutant
                           'g')
Pool 2: ATTGGKGAGTGCCC
       =ATTGGgGAGTGCCC    (complement to mutant
                           'c')
       +ATTGGtGAGTGCCC    (complement to wild type
                           'a')
Pool 3: ATTGGRGAGTGCCC
       =ATTGGaGAGTGCCC    (complement to mutant
                           't')
       +ATTGGgGAGTGCCC    (complement to mutant
                           'c')
```

With 3 pooled probes, all 4 possible single base pair states (wild and 3 mutants) are detected. A pool hybridizes with a target if some probe contained within that pool is complementary to that target.

| Hybridization? | | Pool: (SEQ ID NOS: 23, 31-33, respectively) | | |
|---|---|---|---|---|
| | | 1 | 2 | 3 |
| Target: | TAACCACTCACGGGAGCA | n | y | n |
| Mutant: | TAACCCCTCACGGGAGCA | n | y | y |
| Mutant: | TAACCGCTCACGGGAGCA | y | n | n |
| Mutant: | TAACCtCTCACGGGAGCA | y | n | y |

A cell containing a pair (or more) of oligonucleotides lights up when a target complementary to any of the oligonucleotide in the cell is present. Using the simple strategy, each of the four possible targets (wild and three mutants) yields a unique hybridization pattern among the three cells.

Since a different pattern of hybridizing pools is obtained for each possible nucleotide in the target sequence corresponding to the pooled interrogation position in the probes, the identity of the nucleotide can be determined from the hybridization pattern of the pools. Whereas, a standard tiling requires four cells to detect and identify the possible single-base substitutions at one location, this simple pooled strategy only requires three cells.

A more efficient pooling strategy for sequence analysis is the 'Trellis' strategy. In this strategy, each pooled probe has a segment of perfect complementarity to a reference sequence except at three pooled positions. One pooled position is an N pool (IUPAC standard ambiguity code). The three pooled positions may or may not be contiguous in a probe. The other two pooled positions are selected from the group of three pools consisting of (1) M or K, (2) R or Y and (3) W or S, where the single letters are IUPAC standard ambiguity codes.

The sequence of a pooled probe is thus, of the form XXXN [(M/K) or (R/Y) or (W/S)] [(M/K) or (R/Y) or (W/S)] XXXXX, where XXX represents bases of complementary to the reference sequence (SEQ ID NOS:34-69). The three pooled positions may be in any order, and may be contiguous or separated by intervening nucleotides. For, the two positions occupied by [(M/K) or (R/Y) or (W/S)], two choices must be made. First, one must select one of the following three pairs of pooled nucleotides (1) M/K, (2) R/Y and (3) W/S. The one of three pooled nucleotides selected may be the same or different at the two pooled positions. Second, supposing, for example, one selects M/K at one position, one must then choose between M or K. This choice should result in selection of a pooled nucleotide comprising a nucleotide that complements the corresponding nucleotide in a reference sequence, when the probe and reference sequence are maximally aligned. The same principle governs the selection between R and Y, and between W and S. A trellis pool probe has one pooled position with four possibilities, and two pooled positions, each with two possibilities. Thus, a trellis pool probe comprises a mixture of 16 (4×2×2) probes. Since each pooled position includes one nucleotide that complements the corresponding nucleotide from the reference sequence, one of these 16 probes has a segment that is the exact complement of the reference sequence. A target sequence that is the same as the reference sequence (i.e., a wildtype target) gives a hybridization signal to each probe cell. Here, as in other tiling methods, the segment of complementarity should be sufficiently long to permit specific hybridization of a pooled probe to a reference sequence be detected relative to a variant of that reference sequence. Typically, the segment of complementarity is about 9-21 nucleotides.

A target sequence is analyzed by comparing hybridization intensities at three pooled probes, each having the structure described above. The segments complementary to the reference sequence present in the three pooled probes show some overlap. Sometimes-the segments are identical (other than at the interrogation positions). However, this need not be the case. For example, the segments can tile across a reference sequence in increments of one nucleotide (i.e., one pooled probe differs from the next by the acquisition of one nucleotide at the 5' end and loss of a nucleotide at the 3' end). The three interrogation positions may or may not occur at the same relative positions within each pooled probe (i.e., spacing from a probe terminus). All that is required is that one of the three interrogation positions from each of the three pooled probes aligns with the same nucleotide in the reference sequence, and that this interrogation position is occupied by a different pooled nucleotide in each of the three probes. In one of the three probes, the interrogation position is occupied by an N. In the other two pooled probes the interrogation position is occupied by one of (M/K) or (R/Y) or (WIS).

In the simplest form of the trellis strategy, three pooled probes are used to analyze a single nucleotide in the reference sequence. Much greater economy of probes is achieved when more pooled probes are included in an array. For example, consider an array of five pooled probes each having the general structure outlined above. Three of these pooled probes have an interrogation position that aligns with the same nucleotide in the reference sequence and are used to read that nucleotide. A different combination of three probes have an interrogation position that aligns with a different nucleotide in the reference sequence. Comparison of these three probe intensities allows analysis of this second nucleotide. Still another combination of three pooled probes from the set of five have an interrogation position that aligns with a third nucleotide in the reference sequence and these probes are used to analyze that nucleotide. Thus, three nucleotides in the reference sequence are fully analyzed from only five pooled probes. By comparison, the basic tiling strategy would require 12 probes for a similar analysis.

As an example, a pooled probe for analysis of a target sequence by the trellis strategy is shown below (SEQ ID NOS:70 and 71):

```
Target:      ATTAACCACTCACGGGAGCTCT
Pool:        TGGTGNKYGCCCT
```

The pooled probe actually comprises 16 individual probes (SEQ ID NOS: 72-87, respectively):

```
                TGGTGAGcGCCCT
               +TGGTGcGcGCCCT
               +TGGTGgGcGCCCT
               +TGGTGtGcGCCCT
               +TGGTGAtcGCCCT
               +TGGTGctcGCCCT
               +TGGTGgtcGCCCT
               +TGGTGttcGCCCT
               +TGGTGAGTGCCCT
               +TGGTGcGTGCCCT
               +TGGTGgGTGCCCT
               +TGGTGtGTGCCCT
               +TGGTGAtTGCCCT
               +TGGTGctTGCCCT
               +TGGTGgtTGCCCT
               +TGGTGttTGCCCT
```

The trellis strategy employs an array of probes having at least three cells, each of which is occupied by a pooled probe as described above.

Consider the use of three such pooled probes for analyzing a target sequence, of which one position may contain any single base substitution to the reference sequence (Le., there are four possible target sequences to be distinguished). Three cells are occupied by pooled probes having a pooled interrogation position corresponding to the position of possible substitution in the target sequence, one cell with an 'N', one cell with one of 'M' or 'K' and one cell with 'R' or 'Y'. An interrogation position corresponds to a nucleotide in the target sequence if it aligns adjacent with that nucleotide when the probe and target sequence are aligned to maximize complementarity. Note that although each of the pooled probes has two other pooled positions, these positions are not relevant for the present illustration The positions are only relevant when more than one position in the target sequence is to be read, a circumstance that will be considered later. For present purposes, the cell with the 'N' in the interrogation position lights up for the wildtype sequence and any of the three single base substitutions of the target sequence. The cell with M/K in the interrogation position lights up for the wildtype sequence and one of the single-base substitutions. The cell with R/Y in the interrogation position lights up for the wildtype sequence and a second of the single-base substitutions. Thus, the four possible target sequences hybridize to the three pools of probes in four distinct patterns, and the four possible target sequences can be distinguished.

To illustrate further, consider four possible target sequences (differing at a single position) and a pooled probe having three pooled positions, N, K and Y with the Y position as the interrogation position (i.e., aligned with the variable position in the target sequence):

|  | Target |  |  |
|---|---|---|---|
| Wild: | ATTAACCACTCACGGGAGCTCT | (w) | (SEQ ID NO: 70) |
| Mutants: | ATTAACCACTCcCGGGAGCTCT | (c) | (SEQ ID NO: 88) |
| Mutants: | ATTAACCACTCgCGGGAGCTCT | (g) | (SEQ ID NO: 89) |
| Mutants: | ATTAACCACTCtCGGGAGCTCT | (t) | (SEQ ID NO: 90) |
|  | TGGTGNKYGCCCT (pooled probe). |  | (SEQ ID NO: 71) |

The sixteen individual component probes of the pooled probe hybridize to the four possible target sequences as follows:

|  | TARGET |  |  |  |  |
|---|---|---|---|---|---|
|  | w | c | g | t |  |
| TGGTGAGcGCCCT | n | n | y | n | (SEQ ID NO: 72) |
| TGGTGcGcGCCGT | n | n | n | n | (SEQ ID NO: 73) |
| TGGTGgGcGCCCT | n | n | n | n | (SEQ ID NO: 74) |
| TGGTGtGcGCCCT | n | n | n | n | (SEQ ID NO: 75) |
| TGGTGAtcGCCCT | n | n | n | n | (SEQ ID NO: 76) |
| TGGTGctcGCCCT | n | n | n | n | (SEQ ID NO: 77) |
| TGGTGgtcGCCCT | n | n | n | n | (SEQ ID NO: 78) |
| TGGTGttcGCCCT | n | n | n | n | (SEQ ID NO: 79) |
| TGGTGAGTGCCCT | y | n | n | n | (SEQ ID NO: 80) |
| TGGTGcGTGCCCT | n | n | n | n | (SEQ ID NO: 81) |
| TGGTGgGTGCCCT | n | n | n | n | (SEQ ID NO: 82) |
| TGGTGtGTGCCCT | n | n | n | n | (SEQ ID NO: 83) |
| TGGTGAtTGCCCT | n | n | n | n | (SEQ ID NO: 84) |
| TGGTGctTGCCCT | n | n | n | n | (SEQ ID NO: 85) |
| TGGTGgtTGCCCT | n | n | n | n | (SEQ ID NO: 86) |
| TGGTGttTGCCCT | n | n | n | n | (SEQ ID NO: 87) |

The pooled probe hybridizes according to the aggregate of its components:
Pool: TGGTGNKYGCCCT y n y n (SEQ ID NO:71)

Thus, as stated above, it can be seen that a pooled probe having a y at the interrogation position hybridizes to the wildtype target and one of the mutants. Similar tables can be drawn to illustrate the hybridization patterns of probe pools having other pooled nucleotides at the interrogation position.

The above strategy of using pooled probes to analyze a single base in a target sequence can readily be extended to analyze any number of bases. At this point, the purpose of including three pooled positions within each probe will become apparent. In the example that follows, ten pools of probes, each containing three pooled probe positions, can be used to analyze a each of a contiguous sequence of eight nucleotides in a target sequence.

| Pools: |  |  |
|---|---|---|
| 4 | TAATTNKYGAGTG | (SEQ ID NO. 91) |
| 5 | AATTGNKRAGTGC | (SEQ ID NO. 92) |
| 6 | ATTGGNKRGTGCC | (SEQ ID NO. 93) |
| 7 | TTGGTNMRTGCCC | (SEQ ID NO. 94) |
| 8 | TGGTGNKYGCCCT | (SEQ ID NO. 95) |
| 9 | GGTGANKRCCCTC | (SEQ ID NO. 96) |
| 10 | GTGAGNKYCCTCG | (SEQ ID NO. 97) |
| 11 | TGAGTNMYCTCGA | (SEQ ID NO. 98) |
| 12 | GAGTGNMYTCGAG | (SEQ ID NO. 99) |
| 13 | AGTGCNMYCGAGA | (SEQ ID NO. 10) |

In this example, the different pooled probes tile across the reference sequence, each pooled probe differing from the next by increments of one nucleotide. For each of the readable nucleotides in the reference sequence, there are three probe pools having a pooled interrogation position aligned with the readable nucleotide. For example, the 12$^{th}$ nucleotide from the left in the reference sequence is aligned with pooled interrogation positions in pooled probes 8, 9, and 10. Comparison of the hybridization intensities of these pooled probes reveals the identity of the nucleotide occupying position 12 in a target sequence.

|  |  |  | Pools |  |  |
|---|---|---|---|---|---|
| Targets |  |  | 8 | 9 | 10 |
| Wild: | ATTAACCACTCACGGG AGCTCT | (SEQ ID NO: 70) | Y | Y | Y |
| Mutants: | ATTAACCACTCcCGGG AGCTCT | (SEQ ID NO: 88) | N | Y | Y |
| Mutants: | ATTAACCACTCgCGGG AGCTCT | (SEQ ID NO: 89) | Y | N | Y |
| Mutants: | ATTAACCACTCtCGGG AGCTCT | (SEQ ID NO: 90) | N | N | Y |

Example Intensities:

|  | Wild |  |
|---|---|---|
| = blank cell |  | 'C' |
|  |  | 'G' |
|  |  | 'T' |
|  |  | None |

Thus, for example, if pools 8, 9, and 10 all light up, one knows the target sequence is wildtype. If pools 9 and 10 light up, the target sequence has a C mutant at position 12. If pools 8 and 10 light up, the target sequence has a G mutant at position 12. If only pool 10 lights up, the target sequence has a t mutant at position 12.

The identity of other nucleotides in the target sequence is determined by a comparison of other sets of three pooled probes. For example, the identity of the 13th nucleotide in the target sequence is determined by comparing the hybridization patterns of the probe pools designated 9, 10 and 11. Similarly, the identity of the 14th nucleotide in the target sequence is determined by comparing the hybridization patterns of the probe pools designated 10, 11, and 12.

In the above example, successive probes tile across the reference sequence in increments of one nucleotide, and each probe has three interrogation positions occupying the same positions in each probe relative to the terminus of the probe (i.e., the 7, 8 and 9th positions relative to the 3' terminus). However, the trellis strategy does not require that probes tile in increments of one or that the interrogation position positions occur in the same position in each probe. In a variant of trellis tiling referred to as "loop" tiling, a nucleotide of interest in a target sequence is read by comparison of pooled probes, which each have a pooled interrogation position corresponding to the nucleotide of interest, but in which the spacing of the interrogation position in the probe differs from probe to probe. Analogously to the block tiling approach, this allows several nucleotides to be read from a target sequence from a collection of probes that are identical except at the interrogation position. The identity in sequence of probes, particularly at their 3' termini, simplifies synthesis of the array and result in more uniform probe density per cell.

To illustrate the loop strategy, consider a reference sequence of which the 4, 5, 6, 7 and 8$^{th}$ nucleotides (from the 3' termini are to be read. All of the four possible nucleotides at each of these positions can be read from comparison of hybridization intensities of five pooled probes. Note that the pooled positions in the probes are different (for example in probe 55, the pooled positions are 4, 5 and 6 and in probe 56, 5, 6 and 7).

```
     TAACCACTCACGGGAGCA   Reference   (SEQ ID NO: 23)
                          sequence
55   ATTNKYGAGTGCC                    (SEQ ID NO: 101)
56   ATTGNKRAGTGCC                    (SEQ ID NO: 102)
57   ATTGGNKRGTGCC                    (SEQ ID NO: 93)
58   ATTRGTNMGTGCC                    (SEQ ID NO: 103)
59   ATTKRTGNGTGCC                    (SEQ ID NO: 104)
```

Each position of interest in the reference sequence is read by comparing hybridization intensities for the three probe pools that have an interrogation position aligned with the nucleotide of interest in the reference sequence. For example, to read the fourth nucleotide in the reference sequence, probes 55, 58 and 59 provide pools at the fourth position. Similarly, to read the fifth nucleotide in the reference sequence, probes 55, 56 and 59 provide pools at the fifth position. As in the previous trellis strategy, one of the three probes being compared has an N at the pooled position and the other two have M or K, and (2) R or Y and (3) W or S.

The hybridization pattern of the five pooled probes to target sequences representing each possible nucleotide substitution at five positions in the reference sequence is shown below.

Each possible substitution results in a unique hybridization pattern at three pooled probes, and the identity of the nucleotide at that position can be deduced from the hybridization pattern.

| Targets (SEQ ID NOS: 23, 105-110, 31-33, and 111-116, respectively) | | | | | | |
|---|---|---|---|---|---|---|
| | | Pools | | | | |
| | | 55 | 56 | 57 | 58 | 59 |
| Wild: | TAACCACTCACGGGAGCA | Y | Y | Y | Y | Y |
| Mutant: | TAAgCACTCACGGGAGCA | Y | N | N | N | N |
| Mutant: | TAAtCACTCACGGGAGCA | Y | N | N | Y | N |
| Mutant: | TAAaCACTCACGGGAGCA | Y | N | N | N | Y |
| Mutant: | TAACgACTCACGGGAGCA | N | Y | N | N | N |
| Mutant: | TAACtACTCACGGGAGCA | N | Y | N | N | Y |
| Mutant: | TAACaACTCACGGGAGCA | Y | Y | N | N | N |
| Mutant: | TAACCcCTCACGGGAGCA | N | Y | Y | N | N |
| Mutant: | TAACCgCTCACGGGAGCA | Y | N | Y | N | N |
| Mutant: | TAACCtCTCACGGGAGCA | N | N | Y | N | N |
| Mutant: | TAACCAgTCACGGGAGCA | N | N | N | Y | N |
| Mutant: | TAACCAtTCATGGGAGTA | N | Y | N | Y | N |
| Mutant: | TAACCAaTCACGGGAGCA | N | N | Y | Y | N |
| Mutant: | TAACCACaCACGGGAGCA | N | N | N | N | Y |
| Mutant: | TAACCAcCACGGGAGCA | N | N | Y | N | Y |
| Mutant: | TAACCACgCACGGGAGCA | N | N | N | Y | Y |

Many variations on the loop and trellis tilings can be created. All that is required is that each position in sequence must have a probe with a 'N', a probe containing one of R/Y, M/K or W/S, and a probe containing a different pool from that set, complementary to the wild type target at that position, and at least one probe with no pool at all at that position. This combination allows all mutations at that position to be uniquely detected and identified.

A further class of strategies involving pooled probes are termed coding strategies. These strategies assign code words from some set of numbers to variants of a reference sequence. Any number of variants can be coded. The variants can include multiple closely spaced substitutions, deletions or insertions. The designation letters or other symbols assigned to each variant may be any arbitrary set of numbers, in any order. For example, a binary code is often used, but codes to other bases are entirely feasible. The numbers are often assigned such that each variant has a designation having at least one digit and at least one nonzero value for that digit. For example, in a binary system, a variant assigned the number 101, has a designation of three digits, with one possible nonzero value for each digit.

The designation of the variants are coded into an array of pooled probes comprising a pooled probe for each nonzero value of each digit in the numbers assigned to the variants. For example, if the variants are assigned successive number in a numbering system of base m, and the highest number assigned to a variant has n digits, the array would have about n×(m−1) pooled probes. In general, $\log_m (3N+1)$ probes are required to analyze all variants of N locations in a reference sequence, each having three possible mutant substitutions. For example, 10 base pairs of sequence may be analyzed with only 5 pooled probes using a binary coding system.

Each pooled probe has a segment exactly complementary to the reference sequence except that certain positions are pooled. The segment should be sufficiently long to allow specific hybridization of the pooled probe to the reference sequence relative to a mutated form of the reference sequence. As in other tiling strategies, segments lengths of 9-21 nucleotides are typical. Often the probe has no nucleotides other than the 9-21 nucleotide segment. The pooled positions comprise nucleotides that allow the pooled probe to hybridize to every variant assigned a particular nonzero value in a particular digit. Usually, the pooled positions further comprises a nucleotide that allows the pooled probe to hybridize to the reference sequence. Thus, a wildtype target (or reference sequence) is immediately recognizable from all the pooled probes being lit.

When a target is hybridized to the pools, only those pools comprising a component probe having a segment that is exactly complementary to the target light up. The identity of the target is then decoded from the pattern of hybridizing pools. Each pool that lights up is correlated with a particular value in a particular digit. Thus, the aggregate hybridization patterns of each lighting pool reveal the value of each digit in the code defining the identity of the target hybridized to the array.

As an example, consider a reference sequence having four positions, each of which can be occupied by three possible mutations. Thus, in total there are 4×3 possible variant forms of the reference sequence. Each variant is assigned a binary number 0011-1100 and the wildtype reference sequence is assigned the binary number 1111.

| XXXX - 4 Positions | | | | |
|---|---|---|---|---|
| Target (SEQ ID NO: 117): TAACCACGGGAGCA | C = 1111 | A = 1111 | C = 1111 | T = 1111 |
| | G = 0001 | C = 0010 | G = 0011 | A = 0100 |
| | T = 0101 | G = 0110 | T = 0111 | C = 1000 |
| | A = 1001 | T = 1010 | A = 1011 | G = 1100 |

A first pooled probe is designed by including probes that complement exactly each variant having a 1 in the first digit (SEQ ID NOS:23 and 108-113, respectively).

```
target (1111): TAAC   C      A      C      T CACGGGAGCA
Mutant (0001): TAAC   g      A      C      T CACGGGAGCA
Mutant (0101): TAAC   t      A      C      T CACGGGAGCA
Mutant (1001): TAAC   a      A      C      T CACGGGAGCA
Mutant (0011): TAAC   C      A      g      T CACGGGAGCA
Mutant (0111): TAAC   C      A      t      T CACGGGAGCA
Mutant (1101): TAAC   C      A      a      T CACGGGAGCA First pooled probe
              (SEQ ID NOS: 118 and 118, respectively)
= ATTG [GCAT]  T [GCAT]  A GTGCCC
= ATTG  N      T  N      A GTGCCC
```

Second, third and fourth pooled probes are then designed respectively, including component probes that hybridize to each variant having a 1 in the second, third and fourth digit (SEQ ID NOS:23 and 118-121, respectively):

| XXXX - 4 positions examined | | |
|---|---|---|
| Target: | TAACCACTCACGGGAGCA | |
| Pool 1(1): | ATTGnTnAGTGCCC = | 16 probes (4x1x4x1) |
| Pool 2(2): | ATTGGnnAGTGCCC = | 16 probes (1x4x4x1) |
| Pool 3(3): | ATTGyrydGTGCCC = | 24 probes (2x2x2x3) |
| Pool 1(1): | ATTGmwmbGTGCCC = | 16 probes (2x2x2x3) |

The pooled probes hybridize to valriant targets as follows:

| | | Pools | | | |
|---|---|---|---|---|---|
| Targets | | 1 | 2 | 3 | 4 |
| Wild (1111) | TAACCACTCACGGGAGCA (SEQ ID NO: 23) | Y | Y | Y | Y |
| Mutant (0001): | TAACgACTCACGGGAGCA (SEQ ID NO: 108) | Y | N | N | N |
| Mutant (0101): | TAACtACTCACGGGAGCA (SEQ ID NO: 109) | Y | N | Y | N |
| Mutant (1001): | TAACaACTCACGGGAGCA (SEQ ID NO: 110) | Y | N | N | Y |
| Mutant (0010): | TAACCcCTCACGGGAGCA (SEQ ID NO: 31) | N | Y | N | N |
| Mutant (0110): | TAACCgCTCACGGGAGCA (SEQ ID NO: 32) | N | Y | Y | N |
| Mutant (1010): | TAACCtCTCACGGGAGCA (SEQ ID NO: 33) | N | Y | N | Y |
| Mutant (0011): | TAACCAgTCACGGGAGCA (SEQ ID NO: 111) | Y | Y | N | N |

-continued

|  | Targets | Pools | | | |
|---|---|---|---|---|---|
|  |  | 1 | 2 | 3 | 4 |
| Mutant (0111): | TAACCAtTCACGGGAGCA (SEQ ID NO: 112) | Y | Y | Y | N |
| Mutant (1101): | TAACCAaTCACGGGAGCA (SEQ ID NO: 113) | Y | N | Y | Y |
| Mutant (0100): | TAACCACaCACGGGAGCA (SEQ ID NO: 114) | N | N | Y | N |
| Mutant (1000): | TAACCACcCACGGGAGCA (SEQ ID NO: 115) | N | N | N | Y |
| Mutant (1100): | TAACCACgCACGGGAGCA (SEQ ID NO: 116) | N | N | Y | Y |

The identity of a variant (i.e., mutant) target is read directly from the hybridization pattern of the pooled probes. For example the mutant assigned the number 0001 gives a hybridization pattern of NNNY with respect to probes 4, 3, 2 and 1 respectively.

In the above example, variants are assigned successive numbers in a numbering system. In other embodiments, sets of numbers can be chosen for their properties. If the codewords are chosen from an error-control code, the properties of that code carry over to sequence analysis. An error code is a numbering system in which some designations are assigned to variants and other designations serve to indicate errors that may have occurred in the hybridization process. For example, if all codewords have an odd number of nonzero digits ('binary coding+error detection'), any single error in hybridization will be detected by having an even number of pools lit.

```
Wild Target:
                                      (SEQ ID NO: 23)
          TAACCACTCACGGGAGCA (SEQ ID NOS: 122, 119, 123 and 124, respectively)
Pool 1(1):    ATTGnAnAGTGCCC  =    16 Probes (4x1x4x1)

Pool 2(2):    ATTGGnnAGTGCCC  =    16 Probes (1X4X4X1)

Pool 3(4):    ATTGryrhGTGCCC  =    24 Probes (2X2X2X3)

Pool 4(8):    ATTGkwkvGTGCCC  =    24 Probes (2X2X2X3)
```

A fifth probe can be added to make the number of pools that hybridize to any single mutation odd.

Pool 5(c) (SEQ ID NO: 125): ATTGdhsmGTGCCC = 36 probes (2x2x3x3)
Hybridization of pooled probes to targets:
(SEQ ID NOS: 23, 108-110, 31-33 and 111-116, respectively)

| Target | | Pool | | | | |
|---|---|---|---|---|---|---|
|  |  | 1 | 2 | 3 | 4 | 5 |
| Target (11111): | TAACCACTCACGGGAGCA | Y | Y | Y | Y | Y |
| Mutant (00001): | TAACgACTCACGGGAGCA | Y | N | N | N | N |
| Mutant (10101): | TAACtACTCACGGGAGCA | Y | N | N | N | N |
| Mutant (11001): | TAACaACTCACGGGAGCA | Y | N | N | Y | Y |
| Mutant (00010): | TAACCcCTCACGGGAGCA | N | Y | N | N | N |
| Mutant (10110): | TAACCgCTCACGGGAGCA | N | Y | N | N | Y |

Pool 5(c) (SEQ ID NO: 125): ATTGdhsmGTGCCC = 36 probes (2x2x3x3)
Hybridization of pooled probes to targets:
(SEQ ID NOS: 23, 108-110, 31-33 and 111-116, respectively)

| Target | | Pool | | | | |
|---|---|---|---|---|---|---|
|  |  | 1 | 2 | 3 | 4 | 5 |
| Mutant (11010): | TAACCtCTCACGGGAGCA | N | Y | N | Y | Y |
| Mutant (10011): | TAACCAgTCACGGGAGCA | Y | Y | N | N | Y |
| Mutant (00111): | TAACATTCACGGGAGCA | Y | Y | Y | N | N |
| Mutant (01101): | TAACCAaTCACGGGAGCA | Y | N | Y | Y | N |
| Mutant (00100): | TAACCACaCACGGGAGCA | N | N | Y | N | N |
| Mutant (01000): | TAACCACcCACGGGAGCA | N | N | N | Y | N |
| Mutant (11100): | TAACCACgCACGGGAGCA | N | N | Y | Y | Y |

9. Bridging Strategy

Probes that contain partial matches to two separate (i.e., non contiguous) subsequences of a target sequence sometimes hybridize strongly to the target sequence. In certain instances, such probes have generated stronger signals than probes of the same length which are perfect matches to the target sequence. It is believed (but not necessary to the invention) that this observation results from interactions of a single target sequence with two or more probes simultaneously. This invention exploits this observation to provide arrays of probes having at least first and second segments, which are respectively complementary to first and second subsequences of a reference sequence. Optionally, the probes may have a third or more complementary segments. These probes can be employed in any of the strategies noted above. The two segments of such a probe can be complementary to disjoint subsequences of the reference sequences or contiguous subsequences. If the latter, the two segments in the probe are inverted relative to the order of the complement of the reference sequence. The two subsequences of the reference sequence each typically comprises about 3 to 30 contiguous nucleotides. The subsequences of the reference sequence are sometimes separated by 0, 1, 2 or 3 bases often the sequences, are adjacent and nonoverlapping.

For example, a wildtype probe is created by complementing two sections of a reference sequence (indicated by subscript and superscript) and reversing their order. The interrogation position is designated (*) and is apparent from comparison of the structure of the wildtype probe with the three mismatched probes. The corresponding nucleotide in the reference sequence is the "a" in the superscripted segment.

```
Reference:
                                          (SEQ ID NO: 126)
        5' T_GGCTA^CGAGG AATCATCTGTTA Probes:
            (SEQ ID NOS: 127-130, respectively)
            *
        3' GCTCC CCGAT (Probe from first probe
                        set)
        3' GCACC CCGAT

3' GCCCC CCGAT

3' GCGCC CCGAT

The expected hybridizations are:
Match:
        (SEQ ID NOS: 127, 126 and 127, respectively)
            GCTCCCCGAT

TGGCTACGAGGAATCATCTGGTTA

GCTCCCCGAT

Mismatch:
        (SEQ ID NOS: 127, 126 and 130, respectively)
            GCTCCCCGAT

TGGCTACGAGGAATCATCTGTTA

GCGCCCCGAT
```

Bridge tilings are specified using a notation which gives the length of the two constituent segments and the relative position of the interrogation position. The designation n/m indicates a segment complementary to a region of the reference sequence which extends for n bases and is located such that the interrogation position is in the mth base from the 5' end. If m is larger than n, this indicates that the entire segment is to the 5' side of the interrogation position. If m is negative, it indicates that the interrogation position is the absolute value of m bases 5' of the first base of the segment (m cannot be zero). Probes comprising multiple segments, such as n/m+a/b+ . . . have a first segment at the 3' end of the probe and additional segments added 5' with respect to the first segment. For example, a 4/8 tiling consists of (from the 3' end of the probe) a 4 base complementary segment, starting 7' bases 5' of the interrogation position, followed by a 6 base region in which the interrogation position is located at the third base. Between these two segments, one base from the reference sequence is omitted. By this notation, the set shown above is a 5/3+5/8 tiling. Many different tilings are possible with this method, since the lengths of both segments can be varied, as well as their relative position (they may be in either order and there may be a gap between them) and their location relative to the interrogation position.

As an example, a 16 mer oligo target was hybridized to a chip containing all $4^{10}$ probes of length 10. The chip includes short tilings of both standard and bridging types. The data from a standard 10/5 tiling was compared to data from a 5/3+5/8 bridge tiling (see Table 1). Probe intensities (mean count/pixel) are displayed along with discrimination ratios (correct-probe intensity/highest incorrect probe intensity). Missing intensity values are less than 50 counts. Note that for each base displayed the bridge tiling has a higher discrimination value.

TABLE 1

Comparison of Standard and Bridge Tilings

| TILING | PROBE BASE: | CORRECT PROBE BASE | | | |
|---|---|---|---|---|---|
| | | C | A | C | C |
| STANDARD | A | 92 | 496 | 294 | 299 |
| (10/5) | C | 536 | 148 | 532 | 534 |
| | G | 69 | 167 | 72 | 52 |
| | T | 146 | 95 | 212 | 126 |
| DISCRIMINATION: | | 3.7 | 3.0 | 1.8 | 1.8 |
| BRIDGING | A | — | 404 | — | 156 |
| 5/3 + 5/8 | C | 276 | — | 345 | 379 |
| | G | — | 80 | — | — |
| | T | — | — | — | 58 |
| DISCRIMINATION: | | >5.5 | 5.1 | 2.4 | 1.26 |

The bridging strategy offers the following advantages:
(1) Higher discrimination between matched and mismatched probes,
(2) The possibility of using longer probes in a bridging tiling, thereby increasing the specificity of the hybridization, without sacrificing discrimination,
(3) The use of probes in which an interrogation position is located very off-center relative to the regions of target complementarity. This may be of particular advantage when, for example, when a probe centered about one region of the target gives low hybridization signal. The low signal is overcome by using a probe centered about an adjoining region giving a higher hybridization signal.
(4) Disruption of secondary structure that might result in annealing of certain probes (see previous discussion of helper mutations).

10. Deletion Tiling

Deletion tiling is related to both the bridging and helper mutant strategies described above. In the deletion strategy, comparisons are performed between probes sharing a common deletion strategy, comparisons are performed between probes sharing a common deletion but differing from each other at an interrogation position located outside the deletion. For example, a first probe comprises first and second subsequences of a reference sequence, wherein the first and second subsequences of the reference sequence are separated by a short distance (e.g., 1 or 2 nucleotides). The order of the first and second segments in the probe is usually the same as that of the complement to the first and second subsequences in the reference sequence. The interrogation position is usually separated from The comparison is performed with three other probes, which are identical to the first probe except at an interrogation position, which is different in each probe.

Reference (SEQ ID NO:131): . . . AGTACCAGATCTC - TAA . . .

Probe set (SEQ ID NO:132): CATGGNC AGAGA (N=interrogation position).

Such tilings sometimes offer superior discrimination in hybridization intensities between the probe having an interrogation position complementary to the target and other probes. Thermodynamically, the difference between the hybridizations to matched and mismatched targets for the probe set shown above is the difference between a single-base bulge, and a large asymmetric loop (e.g., two bases of target, one of probe). This often results in a larger difference in stability than the comparison of a perfectly matched probe with a probe showing a single base mismatch in the basic tiling strategy.

The superior discrimination offered by deletion tiling is illustrated by Table 2, which compares hybridization data from a standard 10/5 tiling with a (4/8+6/3) deletion tiling of the reference sequence. (The numerators indicate the length of the segments and the denominators, the spacing of the deletion from the far termini of the segments.) Probe intensities (mean count/pixel) are displayed along with discrimination ratios (correct probe intensity/highest incorrect probe intensity). Note that for each base displayed the deletion tiling has a higher discrimination value than either standard tiling shown.

TABLE 2

Comparison of Standard and Deletion Tilings

| TILING | PROBE BASE: | CORRECT PROBE BASE | | | |
|---|---|---|---|---|---|
| | | C | A | C | C |
| STANDARD | A | 92 | 496 | 294 | 299 |
| (10/5) | C | 536 | 148 | 532 | 534 |
| | G | 69 | 167 | 72 | 52 |
| | T | 146 | 95 | 212 | 126 |
| DISCRIMINATION: | | 3.7 | 3.0 | 1.8 | 1.8 |
| DELETION | A | 6 | 412 | 29 | 48 |
| 4/8 + 6/3 | C | 297 | 32 | 465 | 160 |
| | G | 8 | 77 | 10 | 4 |
| | T | 8 | 26 | 31 | 5 |
| DISCRIMINATION: | | 37.1 | 5.4 | 15 | 3.3 |
| STANDARD | A | 347 | 533 | 228 | 277 |
| (10/7) | C | 729 | 194 | 536 | 496 |
| | G | 232 | 231 | 102 | 89 |
| | T | 344 | 133 | 163 | 150 |
| DISCRIMINATION: | | 2.1 | 2.3 | 2.3 | 1.8 |

The use of deletion or bridging probes is quite general. These probes can be used in any of the tiling strategies of the invention. As well as offering superior discrimination, the use of deletion or bridging strategies is advantageous for certain probes to avoid self-hybridization (either within a probe or between two probes of the same sequence)

11. Nucleotide Repeats

Recently a new form of human mutation, expansion of trinucleotide repeats, has been found to cause the diseases of fragile X-syndrome, spinal and bulbar atrophy, myotonic dystrophy and Huntington's disease. See Ross et al., *TINS* 16, 254-259 (1993). Long lengths of trinucleotide repeats are associated with the mutant form of a gene. The longer the length, the more severe the consequences of the mutation and the earlier the age of onset. The invention provides arrays and methods for analyzing the length of such repeats.

The different probes in such an array comprise different numbers of repeats of the complement of the trinucleotide repeat of interest. For example, one probe might be a trimer, having one copy of the repeat, a second probe might be a sixmer, having two copies of the repeat, and a third probe might be a ninmer having three copies, and so forth. The largest probes can have up to about sixty bases or trinucleotide repeats.

The hybridization signal of such probes to a target of trinucleotide repeats is related to the length of the target. It has been found that on increasing the target size up to about the length of the probe, the hybridization signal shows a relatively large increase for each complete trinucleotide repeat unit in the target, and a small increase for each additional base in the target that does not complete a trinucleotide repeat. Thus, for example, the hybridization signals for different target sizes to a 20 mer probe show small increases as the target size is increased from 6-8 nucleotides and a larger increase as the target size is increased to 9 nucleotides.

Arrays of probes having different numbers of repeats are usually calibrated using known amounts of target of different length. For each target of known length, the hybridization intensity is recorded for each probe. Thus, each target size is defined by the relative hybridization signals of a series of probes of different lengths. The array is then hybridized to an unknown target sequence and the relative hybridization signals of the different sized-probes are determined. Comparison of the relative hybridization intensity profile for different probes with comparable data for targets of known size allows interpolation of the size of the unknown target. Optionally, hybridization of the unknown target is performed simultaneously with hybridization of a target of known size labelled with a different color.

C. Preparation of Target Samples

The target polynucleotide, whose sequence is to be determined, is usually isolated from a tissue sample. If the target is genomic, the sample may be from any tissue (except exclusively red blood cells). For example, whole blood, peripheral blood lymphocytes or PBMC, skin, hair or semen are convenient sources of clinical samples. These sources are also suitable if the target is RNA. Blood and other body fluids are also a convenient source for isolating viral nucleic acids. If the target is mRNA, the sample is obtained from a tissue in which the mRNA is expressed. If the polynucleotide in the sample is RNA, it is usually reverse transcribed to DNA. DNA samples or cDNA resulting from reverse transcription are usually amplified, e.g., by PCR. Depending on the selection of primers and amplifying enzyme(s), the amplification product can be RNA or DNA. Paired primers are selected to flank the borders of a target polynucleotide of interest. More than one target can be simultaneously amplified by multiplex PCR in which multiple paired primers are employed. The target can be labelled at one or more nucleotides during or after amplification. For some target polynucleotides (depending on size of sample), e.g., episomal DNA, sufficient DNA is present in the tissue sample to dispense with the amplification step.

When the target strand is prepared in single-stranded form as in preparation of target RNA, the sense of the strand should of course be complementary to that of the probes on the chip. This is achieved by appropriate selection of primers. The target is preferably fragmented before application to the chip to reduce or eliminate the formation of secondary structures in the target. The average size of targets segments following hybridization is usually larger than the size of probe on the chip.

II. Biotransformation Gene Chips

A. Biotransformation Genes

Biotransformation genes tiled by the invention include any of the 481 known cytochrome P450 genes, particularly, the human P450 genes (see Nebert, *DNA & Cell Biol.* 10, 1-14 (1991); Nelson et al., Pharmacogenetics 6, 1-42 (1996), acetylase genes, monoamine oxidase genes, and genes known to specifically biotransform particular drugs, such as the gene encoding glucuronidase that participates in the pathway by which codeine or morphine are converted to active form. Paul et al., *J. Pharm. Exp. Ther.* 251, 477 (1989). Other genes of particular interest include P450 2D6, P450 2C19, N-acetyl transferase II, glucose 6-phosphate dehydrogenase, pseudocholinesterase, catechol-O-methyl transferase, thiopurine methyltransferase and dihydropyridine dehydrogenase. cDNA and at least partial genomic DNA sequences are available for these genes, e.g., from data bases such as GenBank and EMBL (see Table 3).

TABLE 3

ACCESSION NUMBER CYP LIST

| GENE | ACCESSION NUMBER(S) | IMPORTANCE |
|---|---|---|
| CYP1A1 | D12525 | Cancer Susceptibility |
|  | D01198 |  |
| CYP1A2 | M31664 |  |
|  | M31665 |  |
|  | M31666 |  |
|  | M31667 |  |
|  | U02993 |  |
| CYP2A | X13897 |  |
| CYP2A3 | M33318 | Coumarin 7-hydroxylation |
|  | M33316 |  |
| CYP2A4 | X13930 |  |
| CYP2C8 | X54807 |  |
|  | X54808 |  |
| CYP2C9 | M61855 | Warfarin Metabolism |
|  | J05326 |  |
|  | M61857 |  |
|  | J05326 |  |
|  | L16877 |  |
| CYP2C17 | M61858 |  |
|  | J05326 |  |
| CYP2C18 | M61853 | Drug Metabolism |
|  | J05326 |  |
|  | M61856 |  |
| CYP2C19 | L07093 | S-mephenytoin 4-hydroxylase |
|  | M61854 |  |
|  | J05326 |  |
|  | M15331 |  |
| CYP2D6 | M20403 | Debrisoquin/Sparteine Polymorphism |
|  | M19697 |  |
|  | M24499 |  |
|  | X16866 |  |
|  | X58467 | CYP2D7P pseudogene |
|  | X58468 | CYP2D8P pseudogene |
| CYP2E1 | D10014 | Ethanol Inducible |
|  | J02843 |  |
| CYP3A4 | D11131 | Polymorphic Drug Metabolism |
|  | M14096 |  |
| CYP4F2 | U02388 | Leukotriene B4 omega hydroxylase |
| NAT2 | U23052 | Drug Acetylation/Drug Induced Disease |
|  | U23434 |  |
| TPMT | U11424 | Thiopurine Methyl Transferase-transplantation and childhood leukemia |
|  | U12387 |  |

Additional genomic sequence flanking the regions already sequenced are easily determined by PCR-based gene walking. See Parker et al., *Nucl. Acids Res.* 19:3055-3060. A specific primer for the sequenced region is primed with a general primer that hybridizes to the flanking region.

The CYP2D6 enzyme has debrisoquine oxidase activity. See e.g., Kimura et al., Am. *J. Human. Genet.* 45, 889-904. (1989).

Several therapeutically important compounds are metabolized by CYP2D6. The list includes cardioactive drugs: β-blockers (bufuralol, propranolol, metoprolol, timolol) and antiarrhythmics (sparteine, encainide, flecainide, mexiletine) (Buchert & Woosley, *Pharmacogenetics* 2, 2-11 (1992); Birgersdotter et al., *Brit. J. Clin. Pharmacol.* 33, 275-280 (1992)); psychoactive drugs including tricyclic antidepressants (imipramine, desipramine, nortriptyline) and antipsychotics (clozapine and haloperidol) (Dahl & Bertilsson, *Pharmacogenetics* 3, 61-70 (1993); Fischer et al., *J. Pharmacol. Exp. Ther.* 260, 1355-1360 (1992); Lerena et al., *Drug Monitor* 14, 92-97 (1992)); as well as a variety of other commonly used drugs including codeine and dextromethorphan (Eichelbaum & Gross, *Pharmac. Ther.* 46, 377-394 (1990)) as well as amphetamine, and cocaine. Ten percent of the general population is defective in P450 2D6, an enzyme that demethylates codeine at an earlier stage in the activation pathway, and therefore derives no analgesic benefit from codeine (see Sindrup & Brosen, *Pharmacogenetics* 5, 335-346 (1995))

At least seven different polymorphic variants of the CYP2D6 gene demonstrating autosomal recessive inheritance are associated with a poor drug metabolizer phenotype (see Table 4). These alleles are designated CYP2D6A, CYP2D6B, CYP2D6C, CYP2D6D, CYP2D6E, CYP2D6F, and CYP2D6J (Gonzales & Idle, *Clin. Pharmacokinet.* 26(1), 59-70(1994); Nelson et al., *DNA & Cell Biol.* 12(1), 1-51 (1993)). CYP2D6A, CYP2D6E and CYP2D6F are minor variants of the wild type gene. CYP2D6A has a single nucleotide deletion in exon S with a consequent frame shift (Kagimoto et al., *J. Biol. Chem.* 265, 17209-17214 (1990)). CYP2D6E and CYP2D6F are rare, recently described variants (Gonzales & Idle, supra). CYP2D6B accounts for about 70% of defective alleles. This variant has point mutations in exons 1, 3, 8 and 9 as well as a base change at the third intron splice site that results in aberrant transcript splicing (Gonzales et al., *Nature* 331, 442-446 (1988); Kagimoto et al., *J. Biol. Chem.* 265, 17209-17214 (1990)). CYP2D6C has a three base deletion in exon 5 (Broly and Meyer, *Pharmacogenetics* 3, 123-130 (1993)) and, on the CYP2D6D allele, the entire functional gene is deleted although the pseudogenes remain intact (Gaedigk et al., *Am. J. Hum. Genet.* 48, 943-950 (1991)). The CYP2D6J allele has base changes in both the first and ninth exons that result in amino acid changes (Yokota et al., *Pharmacogenetics* 3, 256-263 (1993). The CYP2D6 gene clusters with other CYP2D genes on human chromosome 22. Also present in this region are two or three highly conserved pseudogenes. Of these, CYP2D7P (three variant forms) and CYP2D8P have been isolated and sequenced (Kimura et al., supra; Helm & Meyer, supra).

TABLE 4

| ALLELE | (EXON) NUCLEOTIDE CHANGES | XBAI HAPLOTYPE | ENZYME ACTIVITY | REF. |
|---|---|---|---|---|
| CYP2D6-wt |  | 29 kb | NORMAL | (97) |
|  |  |  |  | (9) |
| CYP2D6-LI | (3) 1726 G → C | 29 kb |  | (12) |
|  | (6) 2938 C → |  |  | (11) |
|  | T/296 Arg → Cys |  |  | (13) |
|  | (9) 4268 G → |  |  |  |
|  | C/486 Ser → Thr |  |  |  |
|  | (6) 2938 C → |  |  |  |
|  | T/296 Arg → Cys |  |  |  |
|  | (6) 2938 C → |  |  |  |
|  | T/296 Arg → Cys |  |  |  |
| CYP2D6-A | (5) 2637 ΔA | 29 kb | ABSENT | (15) |
| CYP2D6-B | (4) 1934A (+ 6 other mutations) | 29 kb | | (15) |
|  |  | 44 kb |  | (14) |
|  |  | 9 + 16 kb |  | (99) |
| CYP2D6-D | Deletion | 11.5 kb |  |  |
|  |  | (13 kb) |  |  |
| CYP2D6-E | (6) 3023 A → | 29 kb |  |  |
|  | C/324 His → Pro |  |  |  |
| CYP2D6-ΔT1795 | (3) 1795 ΔT/ 152 Try → Gly 153 Stop | 29 kb |  | (98, 100) |
| CYP2D6-C | (5) 2703-5 ΔAAG/281 ΔLys | 29 kb | DECREASED | (44) (101) |

TABLE 4-continued

| ALLELE | (EXON) NUCLEOTIDE CHANGES | XBAI HAPLOTYPE | ENZYME ACTIVITY | REF. |
|---|---|---|---|---|
| CYP2D6-J | (1) 188 C → T/Pro 34 Pro → Ser | 29 kb | | (16) |
| | | 44 kb | | |
| | (3) 1749 G → C | | | |
| | (9) 4268 G → C/486 Ser → Thr | | | |
| CYP2D6-W | (1) 188 C → T/34 Pro → Ser | 29 kb | | (102) |
| | | 44 kb | | |
| | (9) 4268 G → C/486 Ser → Thr | | | |
| CYP2D6-Ch1 | (1) 188 C → T/34 Pro → Ser | 29 kb | | (103) |
| | | 44 kb | | |
| | (2) 1127 C → T | | | |
| | (3) 1749 G → C | | | |
| | (9) 4268 G → C/486 Ser → Thr | | | |
| (CYP2D6-L)$_{12}$ | Amplification of D6-L | 175 kb | INCREASED | (12) |
| | | 42 kb | | (12) |
| (CYP2D6-L)$_2$ | Duplication of D6-L | | | |

Presently used trivial names of CYP2D6 alleles, summary of CYP2D6-Alleles, haplotypes and their phenotypic consequences (modified from U.A. Meyer).
(9) Kimura et al. Am J Hum Genet 45: 889-904 (1989)
(11) Armstrong et al. Hum Genet 91: 616-617 (1993)
(12) Johansson et al. PNAS 90: 11825-11829 (1993)
(13) Tsuneoka et al. J. Biochem Tokyo 114: 263-266 (1993)
(14) Gaedigk et al. Am J Hum Genet 48: 943-950 (1991)
(15) Kagimoto et al. J Biol Chem 265: 17209-17214 (1990)
(16) Yokota et al. Pharmacogenet 3: 256-263 (1993)
(44) Tyndale et al. Pharmacogenet 1: 26-32 (1991)
(97) Gonzales et al. Nature 331: 442-446 (1988)
(98) Evert et al. Pharmacogenet 4: 271-274 (1994)
(99) Evert et al. Naunyn-Schmiedebergs Arch Pharmacol 350: 434-439 (1994)
(100) Saxena et al. Hum Mol Genet 3: 923-926 (1994)
(101) Broly et al. Pharmacogenet 3: 123-130 (1993)
(102) Wang et al. Clin Pharmacol Ther 53: 410-418 (1993)
(103) Johansson et al. Mol Pharmacol 46: 452-459 (1994)

The 2C19 gene is the principal human determinant of S-mephenytoin hydroxylase. Drugs metabolized by this enzyme in addition to mephenytoin include antidepressants and neuroleptics. Variant alleles are described in de Morais et al., J. Biol. Chem. 269(22), 15419-15422 (1994); de Morais et al., Molecular Pharmacology 46, 594-598 (1994). Mutations are known to occur at nucleotides 636 (G-A) and 681 (G-A) of the coding sequence.
CYP2E1 is responsible for metabolizing several anesthetics including ethanol. CYP2A6 metabolizes nicotine. CYP2C9 metabolizes warfarin. A table showing other pairs of drugs and cytochromes P450 that either metabolize the drug or are inhibited by it appears below.

TABLE 5

Cytochrome P450 (CYP) Isoenzyme

| Drug | Class | Metabolizing Enzymes | Inhibited Enzymes | Comments |
|---|---|---|---|---|
| Roxithromycin | Antibiotic | | 3A4 | Clin Pharm and Ther 1991, 49, 158 |
| Spiramycin | Antibiotic | | 3A4 | Clin Pharm and Ther 1991, 49, 158 |
| Taxol | Antitumor | 6a-hydroxylation - 3A | | J Pharm Exp Ther 1994, 268, 1160-1165 |
| Tiracizine | Antiarrhythmic | Urethane cleavage - 2D6 | | Abstracts - 10th Int Symp Mic & Drug Oxid 1994, p 590 |
| Trimipramine | Antidepressant | Hydroxylation - 2D6 | | Chem Path Pharm 1993, 82, 111-120 |
| Tropisetron | 5-HT3 antogonist | 5,6,7-hydroxylation - 2D6 | | Drug Met Disp 1994, 22, 269-274 |
| Zanoterone | Anticancer | Hydroxylation - 3A4/5 | | Abstracts - 10th Int Symp Mic & Drug Oxid 1994, p 593 |
| Econazole | Antifungal | | 3A4 > 1A2 > 2C, 2D6 | Clin Pharm and Ther 1991, 49, 158 (abstract P11-37) |
| Ethosuximide | Anticonvulsant | 3A | | Xenobiotic 1993, 23, 307-315 |
| Finasteride | 5α-Reductase Inhibitor | 3A4 | | Abstracts - 10th Int Symp Mic & Drug Oxide 1994, p 594 |
| FK 506 | Immunosuppressant | 3A4 (major), 2D6 (<10%) | | Abstracts - 10th Int Symp Mic & Drug Oxid 1994, p 587 |
| Flexeril | Muscle relaxant | N-demethylation - 1A2, 3A4, 2D6 (minor) | | Abstracts - 10th Int Symp Mic & Drug Oxid 1994, p 592 |
| Haloperidol | Neuroleptic Agent | 3A | | Abstracts - 10th Int Symp Mic & Drug Oxid 1994, p 179 |
| Ibuprofen | NSAID | 2C8, 2C9, 2C18 | | Clin Pharmacokinetics 1994, 26, 59-70 |
| Ifosfamide | Anticancer | 4-hydroxylation, N-dechloroethylation - 3A4 | | Biochem Pharmacol 1994, 47, 1157-1163 |
| Itraconazole | Antifungal | | 3A4 > 1A2 > 2C, 2D6 | Clin Pharm and Ther 1991, 49, 158 (abstract PII-37) |

TABLE 5-continued

Cytochrome P450 (CYP) Isoenzyme

| Drug | Class | Metabolizing Enzymes | Inhibited Enzymes | Comments |
|---|---|---|---|---|
| Labetalol | Antihypertensive | 2D6 | | Drug Met Disp 1985, 13, 443-448 |
| Ondansetron | 5-HT3 antongonist | 7,8-hydroxylation - 3A, 2D6 | | Drug Met Disp 1994, 22, 269-274 |
| Oxodipine | Antihypertensive | 3A4 | | J Pharm Exp Ther 1992, 261, 381-386 |
| Prednisolone | Corticosteroid | 3A4 | | Drug Met Disp 1990, 18, 595-606 |
| Alfentanil | Analgesic | 3A4 | | Anesthesiology 1992, 77, 467-474 |
| Amiflamine | MAO-A Inhibitor | 2D6 | | Clin Pharmacol Ther 1984, 36, 515-519 |
| Azithromycin | Antibiotic | 3A4 | | Clin Pharm and Ther 1991, 49, 158 |
| Benzphetamine | Anorectic | 2C8, 2C9, 2C18, 3A4 | | Clin Pharmacokinetics 1994, 26, 59-70 |
| Captopril | Antihypertensive | 2D6 | | Eur J Clin Pharm 1987, 31, 633-641 |
| Citalopram | Antidepressant | 2C18, 2C19 | | Ther Drug Monit 1993, 15, 11-17 |
| Clarithromycin | Antibiotic | 3A4 | | Clin Pharm and Ther 1991, 49, 158 |
| Clonazepam | Anticonvulsant | Nitroreduction - 3A4 | | Fundam Clin Pharm 1993, 7, 69-75 |
| Clotramizole | Antifungal | | 3A4 > 1A2 > 2C, 2D6 | Clin Pharm and Ther 1991, 49, 158 (abstract PII-37) |
| Cocaine | | N-demethylation - 3A4 | | Pharmacol 1993, 46, 294-300 |
| Dapsone | Antibacterial | N-hydroxylation - 3A4 | | Mol Pharmacol 1992, 41, 975-980 |
| Delavirdine | HIV-1 Reverse transcriptase Inhibitor | Hydroxylation - 3A4 N-dealkylation - 3A4, 2D6 | | Abstracts - 10th Int Symp Mic & Drug Oxid 1994, p 240 |
| Dextromethorphan | Antitussive | O-demethylation - 2D6 N-demethylation - 3A4, 3A5 | | Biochem Pharm 1994, 48, 173-182 |
| Diazepam | CNS Depressant | 2C8, 2C9, 2C18 | | Clin Pharmacokinetics 1994, 26, 59-70 |
| Diclofenac | NSAID | 2C8, 2C9, 2C18 | | Clin Pharmacokinetics 1994, 26, 59-70 |
| Tamoxifen | Antiestrogen | 3A4, 1A1 | | ISSX Proceedings Vol. 3, 44 |
| Taxotere | Antimitotic | 3A | | ISSX Proceedings Vol. 3, 36 |
| Tenoxicam | NSAID | 2C | | Life Sci 1992, 51, 575-581 |
| Terfenadine | Antihistamine | 3A4 | | Drug Met Diap 1993, 21, 403-409 |
| Timolol | β-blocker | 2D6 | | TiPS 1992, 13, 434-439 |
| Thioridazine | Neuroleptic | 2D6 | | TiPS 1992, 13, 434-439 |
| Tolbutamide | Blood glucose lowering agent | 2C18 | | |
| Tomoxetine | Antidepressant | 2D6 | | TiPS 1992, 13, 434-439 |
| Toremifene | Antiestrogen | 3A4/3A5 - (N-demethylation), 1A | | ISSX Proceedings Vol 3, 22 |
| Triazolam | Hypnotic | 3A4 | | |
| Trifluperidol | Neuroleptic | 2D6 | | TiPS 1992, 13, 434-439 |
| Troleandomycin | Antibiotic | | 3A4 | |
| Verapamil | Antihypertensive | 3A4 (mainly), also 1A2 for D-617 metabolite | | Arch pharmacol 1993, 348, 332-337 |
| Vinblastine | Antitumor | 3A4 | | |
| Warfarin | Anticoagulant | 3A, 2C, 1A2 | | |
| Zonisamide | Anticonvulsant | 3A | | Molec Pharm 1993, 44, 216-221 |
| Acetaminophen | Antipyretic | 3A4, 2E1, 1A2 | | Chem Res Tox 1993, 6, 511 |
| Amiodarone | Antiarrhythmic | 3A - deethylatin, 1A2 | 1A2, 2C18, 2D6, 3A4 | Drug Met Disp 1993, 21, 978-985 |
| Amitriptyline | Antidepressant | 2C18, 2D6 | | |
| Astemizole | Anthistamine | 3A4 | | |
| Bufuralol | β-Blocker | 2D6 | | TiPS 1992, 13, 434-439 |
| Carbamazepine | Anticonvulsant | 3A | | Inducer of 3A4; Clin Pharmacokin 1993, 25, 450-482 |
| Chlorzoxazone | Muscle relaxant | 2E1 - 6-OH metabolite | | Chem Res Tox 1990, 3, 566-573 |
| Cimetidine | Antiulcer | | 3A4, 2D6 > 1A2, 2E1 | Gastroent 1991, 101, 1680-1691 |

TABLE 5-continued

Cytochrome P450 (CYP) Isoenzyme

| Drug | Class | Metabolizing Enzymes | Inhibited Enzymes | Comments |
|---|---|---|---|---|
| Ciprofloxacin | Antimicrobial | | 3A4 | Clin Pharmacokinet 1992, 23, 132-146 |
| Clomipramine | Antidepressant | 2C18, 2F6 | | |
| Clozapine | Neuroleptic | 2D6 | | TiPS 1992, 13, 434-439 |
| Codeine | Analgesic | 2D6 - demethylation | | |
| Cyclosporin | Immunospressant | 3A4 | | hydroxylated and N-demethylated metabolites |
| Dapsone | Antibacterial | 3A4 | | |
| Debrisoquine | Antihypertensive | 2D6 | | |
| Desipramine | Antidepressant | 2D6 | | TiPS 1992, 13, 434-439 |
| Dextromethorphan | Antitussive | 2D6 | | |
| Diazepam | CNS Depressant | 2C18 | | |
| Diltiazam | Antihypertensive | 3A4 | | |
| Ebastine | Antihistamine | 3A4, 2D6 | | Structure similar to terfenadine |
| Encainide | Antiarrhythmic | 2D6 | | |
| Erythromycin | Antibiotic | 3A4 | 3A, 1A2 | noncompetitive inhibitor |
| Felodipine | Antihypertensive | 3A4 | | |
| Flecainde | Antiarrhymic | 2D6 | | |
| Fluoxetine | Antidepressant | 2D6, 3A? - Demethylation | 2D6 (S > R) | J Pharm Exp Ther 1993, 266, 964-971) |
| Fluphenazine | Neuroleptic | 2D6 | | TiPS 1992, 13, 434-439 |
| Guanoxan | Antihypertensive | 2D6 | | TiPS 1992, 13, 434-439 |
| Hydrocortisone | Antiinflammatory | 3A4 | | |
| Imipramine | Antidepressant | 2D6-hydroxylation 3A4, 2C19 - demethylation | | Biol Pharm Bull 1993, 16, 571 |
| Indoramin | Antihypertensive | 2D6 | | TiPS 1992, 13, 434-439 |
| Ketoconazole | Antifungal | | 3A4 > 1A2 > 2C, 2D6 | |
| Lidocane | Anesthetic | 3A4 | | Clin Pharm Ther 1989, 46, 521-527 |
| Loratadine | Antihistamine | 3A4, 2D6 | | formation of SCH 34117 |
| Lovastatin | Cholesterol lowing agent | 3A4 | | Arch Biochem Biophys 1991, 290, 355 |
| Mephenytoin | Anticonvulsant | 2C18 | | |
| Metoprolol | Antihypertensive | 2D6 | | |
| Mexiletine | Antiarrhythmic | 2D6 | | TiPS 1992, 13, 434-439 |
| Nifedipine | Antihypertensive | 3A | | J Biol Chem 1986, 261, 5051-50601 |
| Nitrendipine | Antihypertensive | 3A4 | | |
| Nortriptylin | Antidepressant | 2D6 | | TiPS 1992, 13, 434-439 |
| Omeprazole | Antiulcer | 3A4 (major), 2C18 | 2C18 | ISSX Proceedings Vol 3, 45-46; Inducer of 1A2, Clin Pharmacokin 1993, 25, 450-482 |
| Perphenazine | Neurologic | 2D6 | | TiPS 1992, 13, 434-439 |
| Phenytoin | Antiepileptic | 3A, 2C18 | | Probable inducer of 3A4; Clin Pharmacokin 1993, 25, 450-482 |
| Propafenone | Antiarrhythmic | 3A4, 1A2 - demethylation, 2D6 | | Molec Pharm 1993, 43, 120-126 |
| Propanalol | Antihypertensive | 2C18, 2D6 | | |
| Quinidine | Antiarrhymic | 3A4 | 2D6 | |
| Ranitidine | Antiulcer | 2D6 | | |
| Bunitrolol | antihypertensive | 4-hydroxylation - 2D6 | | |

B. Tissue Sample Preparation

The source of target DNA for detecting mutations in biotransformation genes is usually genomic. In adults, samples can conveniently be obtained from blood or mouthwash or cheek scraping epithelial cells. cDNA can be obtained only from tissues in which biotransformation genes are expressed. The liver is a good source, but a surgical biopsy is required to remove a sample from living patients.

C. Amplification

The target DNA is usually amplified by PCR. Primers can be readily devised from the known genomic and cDNA sequences of biotransformation genes. The selection of primers, of course, depends on the areas of the target sequence that are to be screened. The choice of primers also depends on the strand to be amplified. Because some nonallelic P450 genes show a high degree of sequence identity, selection of primers can be important in determining whether one or more nonallelic segments is amplified. Usually, primers will be selected to be perfectly complementary to a unique sequence within a selected target resulting in amplification of only that target. Examples of suitable primers are shown in Table 6 (F=forward primer, R=reverse primer).

TABLE 6

| SEQUENCE NAME | SEQUENCE (SEQ ID NOS: 133-150) |
|---|---|
| CYP2DE1F | GCCAGGTGTGTCCAGAGGAGCCCAT |
| CYP2DE1R | CTGGTAGGGGAGCCTCAGCACCTCT |
| CYP2DE2F | TAGGACTAGGACCTGTAGTCTGGGGT |
| CYP2DE2R | GGTCCCACGGAAATCTGTCTCTGT |
| CYP2DE34F | CTAATGCCTTCATGGCCACGCGCA |
| CYP2DE34R | TCGGGAGCTCGCCCTGCAGAGA |
| CYP2DE5F | GGGCCTGAGACTTGTCCAGGTGAA |
| CYP2DE5R | CCCTCATTCCTCCTGGGACGCTCAA |
| CYP2DE6F | CCCGTTCTGTCCCGAGTATGCTCT |
| CYP2DE6R | TCGGCCCTGCACTGTTTCCCAGA |
| CYP2DE7F | GCTGACCCATTGTGGGGACGCAT |
| CYP2DE7R | CTATCACCAGGTGCTGGTGCTGAGCT |
| CYP2DE89F | GGGAGACAAACCAGGACCTGCCAGA |
| CYP2DE89R | CTCAGCCTCAACGTACCCCTGTCT |
| CYP2D678-F | TGAGAGCAGCTTCAATGATGAGAACCT |
| CYP2D678-R | GTAGGATCATGAGCAGGAGGCCCCA |
| CYP-PCR8-F | TCCCCCGTGTGTTTGGTGGCA |
| CYP-PCR9-R | TGCTTTATTGTACATTAGAGC |

For analysis of mutants through all or much of a gene, it is often desirable to amplify several segments from several paired primers. The different segments may be amplified sequentially or simultaneously by multiplex PCR. Frequently, fifteen or more segments of a gene are simultaneously amplified by PCR. The primers and amplifications conditions are preferably selected to generate fluorescently labelled DNA targets. Double stranded targets are enzymically degraded to fragments of about 100 bp and denatured before hybridization.

D. Tiling Strategies

Mutations in biotransformation genes can be detected by any of the tiling strategies noted above. For detection of hitherto uncharacterized mutations, the basic tiling strategy is one suitable strategy. The chips contain-probes tiling across some or all of a reference sequence.

For detecting precharacterized mutations, which account for the large majority of poor metabolizers in the preferred reference genes described above, the block tiling strategy is one particularly useful approach. In this strategy, a group (or block) of probes is used to analyze a short segment of contiguous nucleotides (e.g., 3, 5, 7 or 9) from a biotransformation gene centered around the site of a mutation.

In a preferred embodiment, a first group of probes is tiled based on a wildtype reference sequence and a second group is tiled based a mutant version of the wildtype reference sequence. The mutation can be a point mutation, insertion or deletion or any combination of these. The presence of first and second groups of probes facilitates analysis when multiple target sequences are simultaneously applied to the chip, as is the case when a patient being diagnosed is heterozygous in a biotransformation gene. The principles of chip design and analysis are as described for the CFTR chip.

E. Modifications for Determining Gene Copy Number

As discussed in connection with the CFTR chip, the tiling arrays of the invention are usually capable of simultaneously analyzing heterozygous alleles of a target sequence. The presence of heterozygous alleles is signalled by two probes having interrogations positions aligned with the mutation showing specific hybridization, rather than one, as would be the case for homozygous alleles. Interpretation of hybridization patterns is, however, sometimes complicated by the presence of less than, or more than, the two expected copies of a biotransformation gene in an individual.

For example, an individual having one wildtype copy of the gene, and a wholly deleted second copy of the gene would show a similar hybridization pattern to an individual with two wildtype copies (other than for possible differences in overall intensity of the pattern). In fact, complete gene deletions of one or both copies of a gene account for approximately 15% of slow metabolizers having defective biotransformation enzymes. Analogous loss of heterozygosity occurs in other diseases such as cancer (p53) and muscular dystrophy (dystrophin gene).

Further, an individual with three wildtype copies of a biotransformation gene would show a similar hybridization pattern to an individual with two copies of the gene, other than for a difference in overall intensity. Individuals having multiple copies of a biotransformation gene are referred to as super metabolizers, because of their elevated levels of enzymes.

Additional complications in interpreting a hybridization pattern can result from the presence of pseudogenes in an individual. A pseudogene is an analog of a true gene that shows strong sequence identity to the true gene but is not expressed. Most pseudogenes having counterparts among the biotransformation genes have been sufficiently well characterized that their presence can be avoided by appropriate selection of amplification primers (i.e., primers are selected that hybridize to the true gene of interest without hybridizing to the pseudogene). For example, 5' TGA GAG CAG CTT CAA TGA TGA GAA CCT 3' and 5' GTA GGA TCA TGA GCA GGA GGC CCC A 3', can be used for amplifying exon 6. However, occasionally a pseudogene might be unexpectedly amplified together with a true gene, and the presence of mutations in the psuedogene (which in fact have no phenotypic effect) might be mistakenly thought to occur in the true gene.

The invention provides tiling arrays to overcome these difficulties by indicating how many copies of a target are present in a sample. In addition to containing the probes required for the tiling strategies described above, these arrays contain probes for analyzing polymorphic sites of a target gene, which do not exert any phenotypic effect (i.e., silent polymorphic sites). The frequency and diversity of such sites is usually greater than that of mutations whose presence does exert a phenotypic effect. Silent sites are predominantly found in intronic regions and in flanking regions (i.e., within about 20 kb of transcribed regions), where selective pressure is generally lower relative to the coding regions. Any number of additional polymorphic sites can be tiled using the same strategies as previously described. For any particular polymorphic site, each form of the polymorphism at that sites serves as a reference sequence for a separate tiling. In some instances, silent polymorphic sites can be amplified from the same primers and on the same amplicon as the sites of potential mutations. In other instances, separate amplification is required.

Silent polymorphic regions can be identified by comparing segments of target DNA, particularly introns and flanking.

regions, from different individuals. Comparison can be performed using the general tiling strategies disclosed above or by conventional techniques such as single-stranded conformational analysis. See, e.g., Hayashi, *PCR Methods & Applications* 1, 34-38 (1991); Orita, *Proc. Natl. Acad. Sci. USA* 86, 2766-2270 (1989); Orita et al., *Genomics* 5, 874-879 (1989). This method has been successfully employed in dystrophin gene analysis coupled with heteroduplex formation to scan for new mutations. Prior et al., *Human Molecular Genetics* 2, 311-313 (1993).

Analysis of the hybridization pattern of a probe array tiling a silent polymorphic region indicates which of the polymorphic forms are present at this region. Consider a polymorphism constituting a single base change. If the polymorphism and flanking sequences are tiled according to the basic strategy using four probe sets, there are four probes having an interrogation position aligned with the single base at which the polymorphism occurs. The number of these four probes to show specific hybridization indicates the number of different polymorphic forms present, and hence, the minimum number of copies of a gene present. For example, if two probes show specific hybridization, at least two polymorphic forms are present. There may be more copies of the gene than polymorphic forms observed at any one site, because the same polymorphic form may be present in more than one copy of the gene. However, if sufficient polymorphic sites are examined, it is likely that a site will be found at which each copy of the gene exists in a different polymorphic form. Thus, the copy number of a gene can be deduced from the number of polymorphic forms present at the polymorphic site(s) showing the greatest number of polymorphic forms.

If a silent polymorphism is more complicated than a single-base change (e.g., deletion or insertion), the number of polymorphic forms can be determined from alternative tilings to the different forms, as generally described in §I.B.1. For example, if all the perfectly matched probes in a first tiling hybridize, it is concluded that the polymorphic form constituting the reference sequence for the first tiling is present. If, all the perfectly matched probes in two (or more) tilings hybridize, it is concluded that two (or more) polymorphic forms are present.

F. Applications

In general, the biotransformation genes described above are inherited in an autosomal recessive fashion. The presence of a homozygous mutation or two heterozygous mutations in an individual signals that the individual is a poor metabolizer of any drug metabolized by the biotransformation gene in which the mutation occurs. Some individuals with one mutant and one normal gene show a near wildtype phenotype, but other such individuals show an intermediate phenotype between normal and homozygous mutant. Individuals having additional copies of a biotransformation gene usually express the gene product at higher levels than a wildtype individual.

The screening methods can be routinely applied as precaution before administering a drug to a patient for the first time. If the patient is found to lack both copies of a gene expressing an enzyme required for detoxification of a particular drug, the patient generally should not be administered the drug or, should be administered the drug in smaller doses compared with patients having normal levels of the enzyme. The latter course may be necessary if no alternative treatment is available. If the patient is found to lack both copies of a gene expressing an enzyme required for activation of a particular drug, the drug will have no beneficial effect on the patient and should not be administered. Patients having one wildtype copy of a gene and one mutant copy of a gene, and who are at risk of having lower levels of an enzyme, should be administered drugs metabolized by that enzyme only with some caution, again depending on whether alternatives are available. If the drug is detoxified by the enzyme in question, the patient should in general be administered a lower dose of the drug. If the drug is activated by the enzyme, the heterozygous patient should be administered a higher dosage of the drug. The reverse applies for patients having additional copy(ies) of a particular biotransformation gene, who are at risk of having elevated levels of an enzyme. The more rational selection of therapeutic agents that can be made with the benefit of screening results in fewer side effects and greater drug efficacy in poor metabolizer patients.

The methods are also useful for screening populations of patients who are to be used in a clinical trial of a new drug. The screening identifies a pool of patients, each of whom has wildtype levels of the full complement of biotransformation enzymes. The pool of patients are then used for determining safety and efficacy of the drugs. Drugs shown to be effective by such trials are formulated for therapeutic use with a pharmaceutical carrier such as sterile distilled water, physiological saline, Ringer's solution, dextrose solution, and Hank's solution.

The chips are also useful for screening patients for increased risk of cancer in similar manner to the p53 chips of the invention. Some biotransformation enzymes have roles in activating environmental procarcinogens to carcinogenic form (e.g., 1A1, 2D6, 2E1 and N-acetyltransferase). Mutations in genes encoding these enzymes are associated with reduced cancer risk. Other biotransformation enzymes have roles in detoxifying environmental carcinogens, e.g., glutathione S-transferase M1. Mutations in one, and especially both, copies of genes encoding such enzymes are associated with enhanced susceptibility to cancer. See Shields, *Environmental Health Perspectives* 102 (sup. 11), 81-87 (1994).

CYP genotype information can be useful to prevent drug-drug interactions in two main ways. First, some drugs are known to inhibit specific CYP enzymes. When such a drug is given, care should be taken not to give a second drug handled by the inhibited pathway (see Table 4). Second, when a person is genotyped as a poor metabolizer, not only should drug doses be decreased, second drugs handled by the poor metabolizing pathway should not be added to the therapy.

Example

Figure 10:
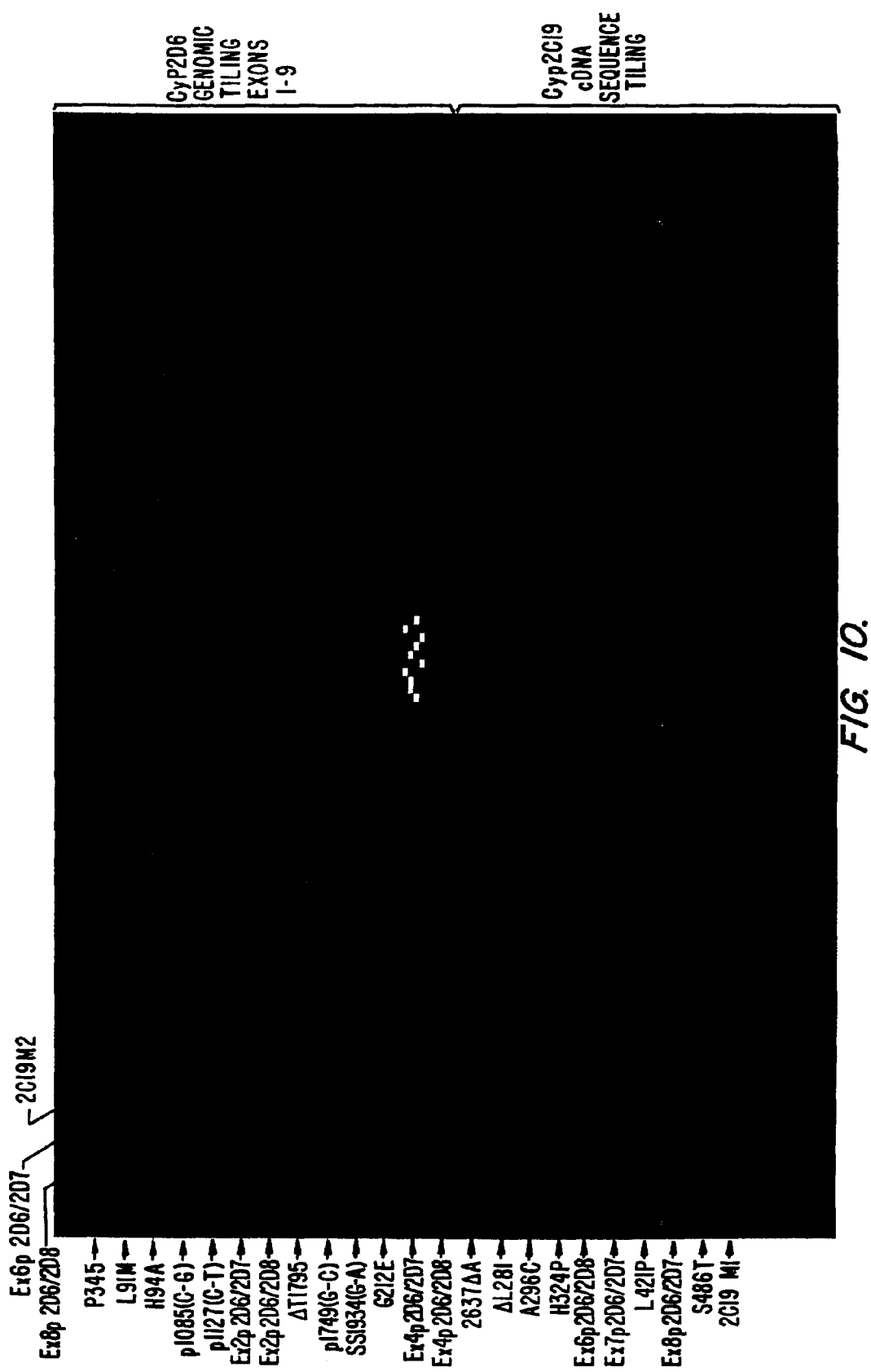
FIG. 10: Layout of probes on chip for analysis of cytochrome P450 2D6 and cytochrome P450 2C19.

FIG. 10 shows the layout of probes and a computer-simulated hybridization pattern for an exemplary chip containing tilings for CYP2D6 and CYP2C19 (wildtype). The chip contains a number of separate tilings as follows.

(1) A tiling (basic strategy) of all 9 exons plus 5 nucleotides of each intron bordering the exons of the CYP2D6 gene. The probes were 14 mers with the interrogation position at nucleotide 7. This tiling is the upper right of the figure (excluding the eleven columns of probe sets on the left of the chip). Each lane of probes is divided into four columns, occupied by probes differing at the interrogation position. At any one column, a nucleotide in the target sequence aligned with the column position is identified as the complement of the nucleotide in the column having the highest fluorescent intensity.

(2) A tiling (basic strategy) of the complete coding sequence (cDNA/mRNA) of CYP2C19 (wildtype). The probes were 15 mers with the interrogation position at nucleotide 7. This tiling is in the lower half of the figure (excluding the eleven columns of probes at the left of the figure).

(3) A series of "opti-block" tilings for analysis of known mutations in CYP2D6 and CYP2C19. These blocks run down the lefthand eleven columns of the figure. These blocks are labelled 2C19 m2 (mutation in cytochrome P450 2C19), p34S, L91M, H94A, p1085, p1127, Delta T 1795, p1749, ss 1934, G212E, 2637DeltaA, delta281, 296C, H324P, L421P, S486T, 2C19 m1 (mutation in cytochrome P450 2C19). Unless otherwise indicated, the mutations occur in cytochrome P450 2D6.

(4) A series of alternative tilings for analysis of known polymorphic differences between CYP2D6 and its pseudogenes CYP2D7P, CYP2D7AP and CYP2DAP. These tilings are also in the lefthand column of the figure. These tilings are labelled Ex6p 2D6/2D7, Ex2p 2D6/2D7, Ex2p 2D6/2D8, Ex4p 2D6/2D7, Ex4p 2D6/2D8, Ex6p 2D6/2D8, Ex7p 2D6/2D7, and Exp 2D6/2D7.

Figure 11:
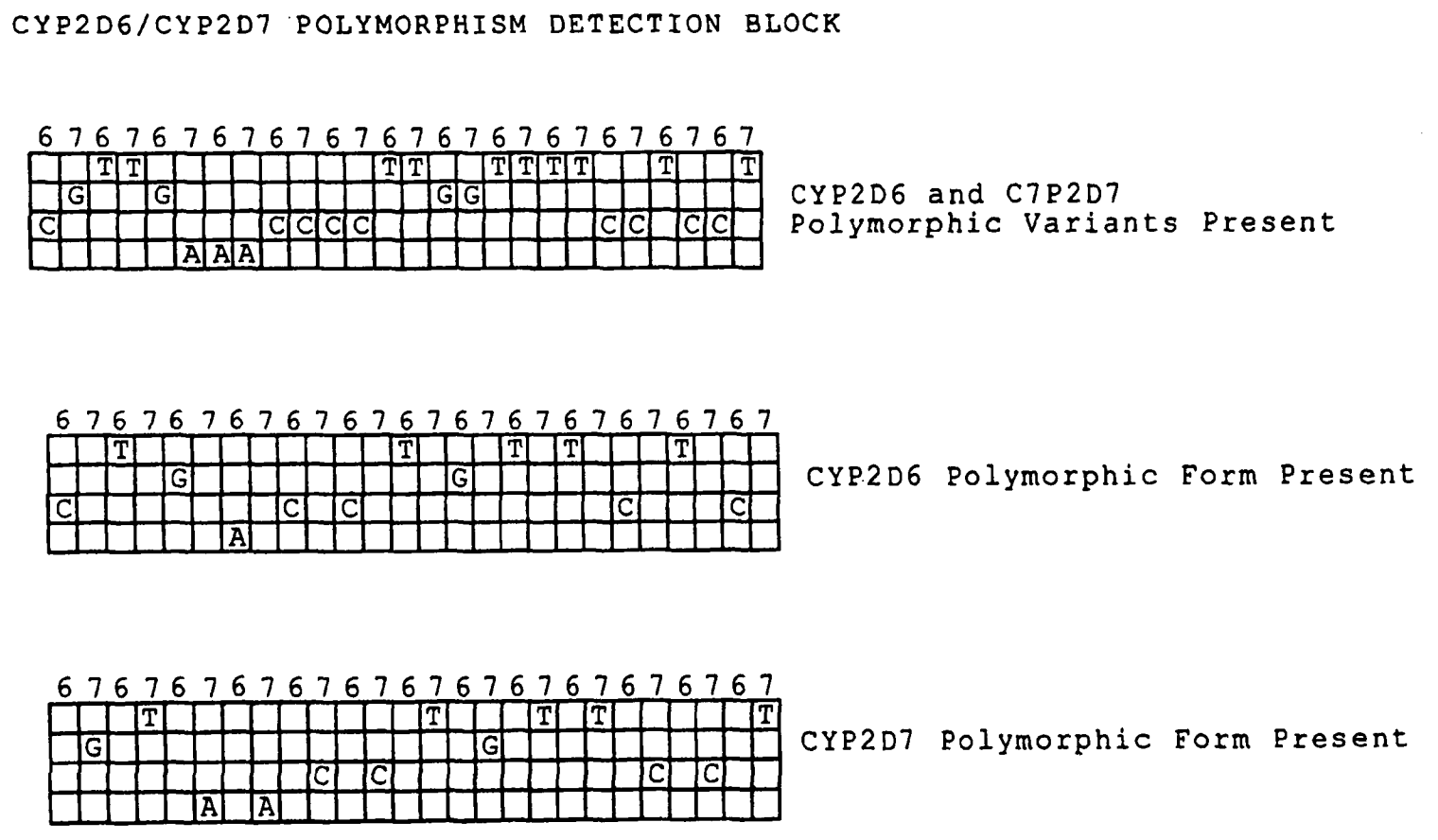

FIG. 11 shows an alternative tiling designed to distinguish 2D6 from the pseudogene 2D7 in CYP2D6. Alternative tilings are formed from two interdigitated tilings, each designed according to the basic tiling strategy based on two different reference sequences, in this case 2D6 and 2D7. The first column contains four probes complementary to the CYP2D6 sequence except at the interrogation position. The second column contains four probes complementary to the CYP2D7 sequence except at the interrogation position. The interrogation positions of the first and second columns of probes align with the same positions of the target sequence. The same strategy of alternating probes from the respective 2D6 and 2D7 reference sequences continues throughout the alternative tiling. When the tiling is hybridized to only the CYP2D6 form, only probes complementary to CYP2D6 (i.e., the columns labelled 6) light up. Conversely when the tiling is hybridized to only the CYP2D7 form, only probes in the columns labelled 7 light up. When the tiling is hybridized to a mixture of CYP2D6 and CYP2D7, the pattern is the sum of the pattern for the two individual forms. The characteristic patterns throughout the tiling allow distinction of whether CYP2D6, CYP2D7 or both are present.

FIG. 12 shows an optiblock of probes for distinguishing the P34S mutation from the wildtype sequence of CYP2D6. In an optiblock, probes are selected based on the block tiling strategy. That is all probes align with the same segment of target DNA but differ in the location of the interrogation position and in whether the probes are tiled based on a wildtype or mutant reference sequence. The notation "n" above the chip indicates that the interrogation position is aligned with the site of the P34S mutation in the target DNA and, the notation n−1 and n+1 indication interrogation positions aligned one base either side of the site of mutation and so forth. As in the alternate tiling, probes tiled on wildtype and mutant sequences (sometimes referred to as wildtype and mutant probes) are interdigitated. The result of hybridizing the optiblock to wildtype target is that all columns containing probes tiled based on the wildtype sequence light up. In addition, one column of probes based on the mutant sequence lights up, this being the column of probes having an interrogation position aligned with the "n" nucleotide in the target. The result of hybridizing the optiblock to the mutant target is the reverse; that is all columns of probes tiled based on the mutant target sequence light up, and a single column of probes tiled based on the wildtype sequence lights up. When the optiblock is hybridized to a heterozygous target containing wildtype and mutant forms, the pattern is the sum of those obtained with the individual targets alone. Thus, all three possible targets, homozygous wildtype, homozygous mutant and heterozygote give distinct patterns of hybridization and can be distinguished.

The chip was hybridized with fluorescein-labelled-dGTP double-stranded DNA made by PCR from a plasmid template containing the genomic clone of CYP2D6-B. The entire gene is amplified as 4 separate PCR products, all of which were present during hybridization. dUTP was incorporated during PCR and the PCR products were treated with uracil DNA glycosylase, then heated to 95° C. for 5 min before hybridization to fragment and denature double-stranded material. Hybridization was for 30 min at 37° C. in 0.5 M LiCl plus 0.0005% NaLauroylSarkosine. Washing was performed prior to scanning the same solution without target DNA for 5 min at room temperature.

Figure 13:
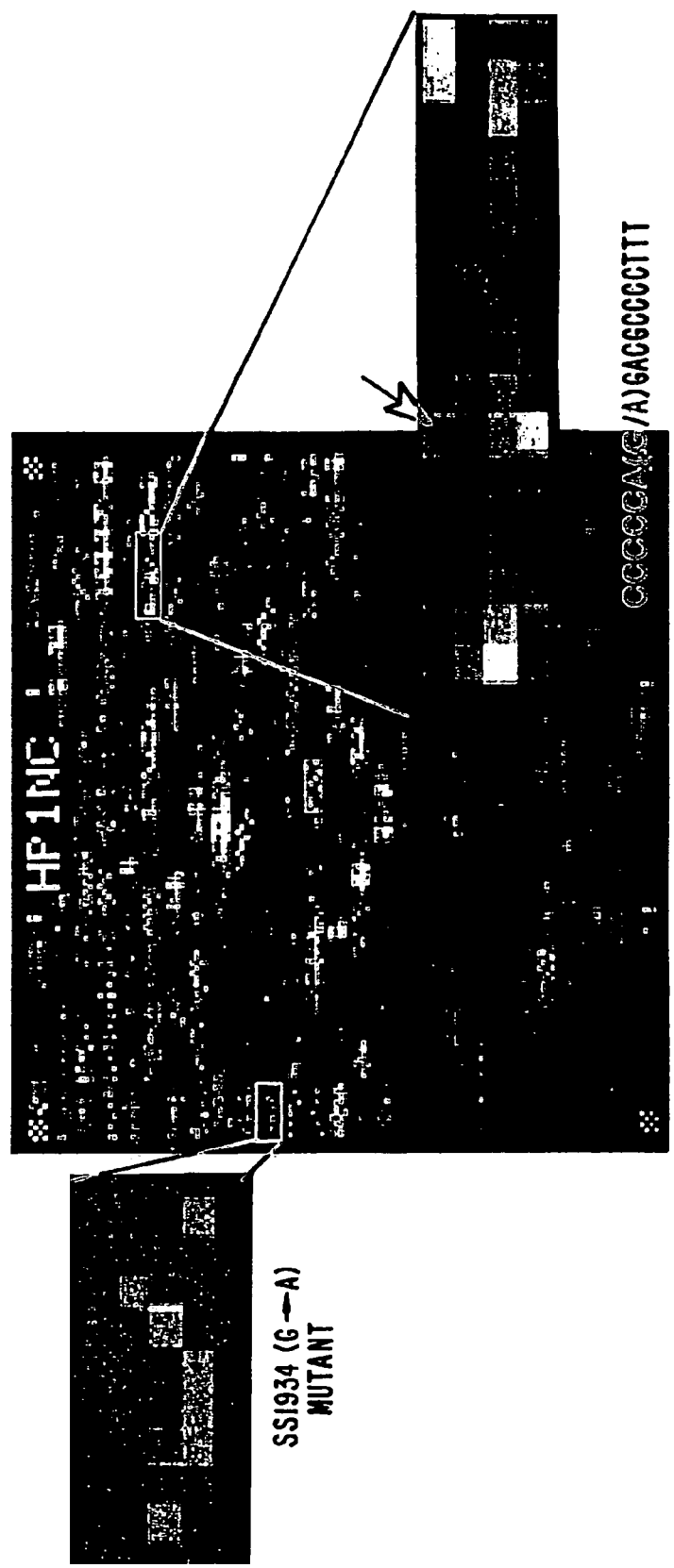
FIG. 13 (SEQ ID NO: 22): The chip shown in FIG. 10 hybridized to a CYP2D6-B target.

FIG. 13 shows the chip hybridized to a CYP2D6-B target. A portion of the basic tiling pattern is shown magnified in the lower right hand corner. Successive nucleotides in the target sequence can be read by eye by comparing the sequence intensities of the four squares in a column. From top to bottom, these squares are respectively occupied by probes having A, C, G and T at the interrogation position. The nucleotide occupying the position in the target sequence aligned with the interrogation position of a column of probes is the complement of the interrogation position of the probe showing the highest signal. The SS1934 mutation in CYP2D6-B results in a G-A transition and loss of function. The enlarged hybridization pattern in the lower right of the figure has an arrow in the column corresponding to nucleotide 1934. In this column, the probe hybridizing most strongly has a T in the interrogation position. This implies that the corresponding nucleotide in the target is the complement of T, i.e., A, indicating that the mutant form of the target is present. The same result is apparent from the optiblock shown in the upper left of the figure. This block shows three consecutive columns in which the T-probe lights up. Two of these columns are from wildtype and mutant probes having interrogation positions aligned with nucleotide 1934. The third column (the leftmost of the three) is the mutant probe having an interrogation position aligned with nucleotide 19.33.

Figure 14:
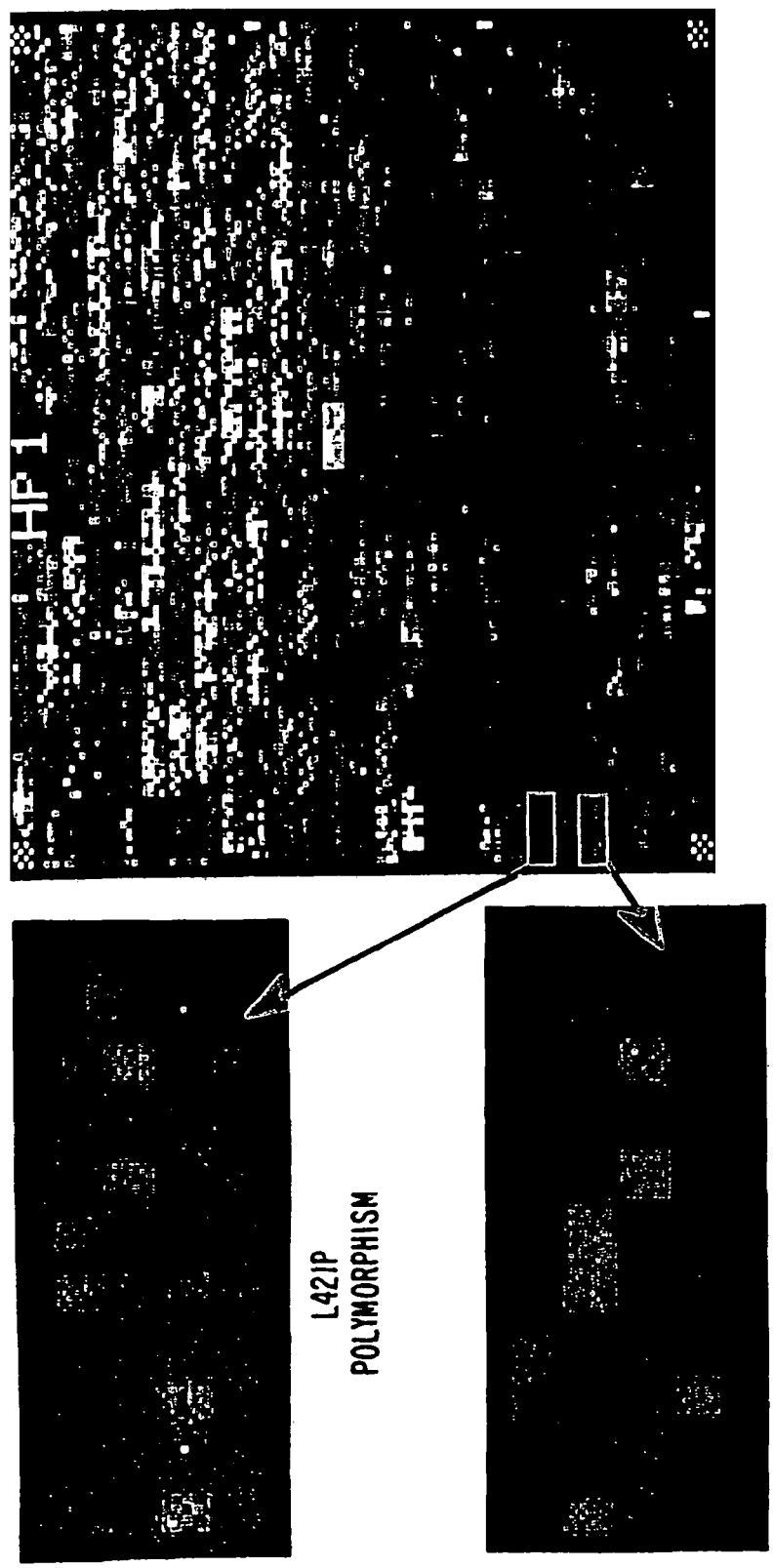
FIG. 14: Magnification of the hybridization patterns of the cytochrome P450 2D6 L421P and S486 polymorphism optitiling blocks.

FIG. 14 shows magnifications of the hybridization patterns of L421P and S486 opti-tiling blocks. In each case, the first, third, fifth, sixth, seventh, and ninth columns light up. This pattern indicates that homozygous wildtype sequence is present (see the idealized pattern for homozygous wildtype in FIG. 12).

Figure 15:
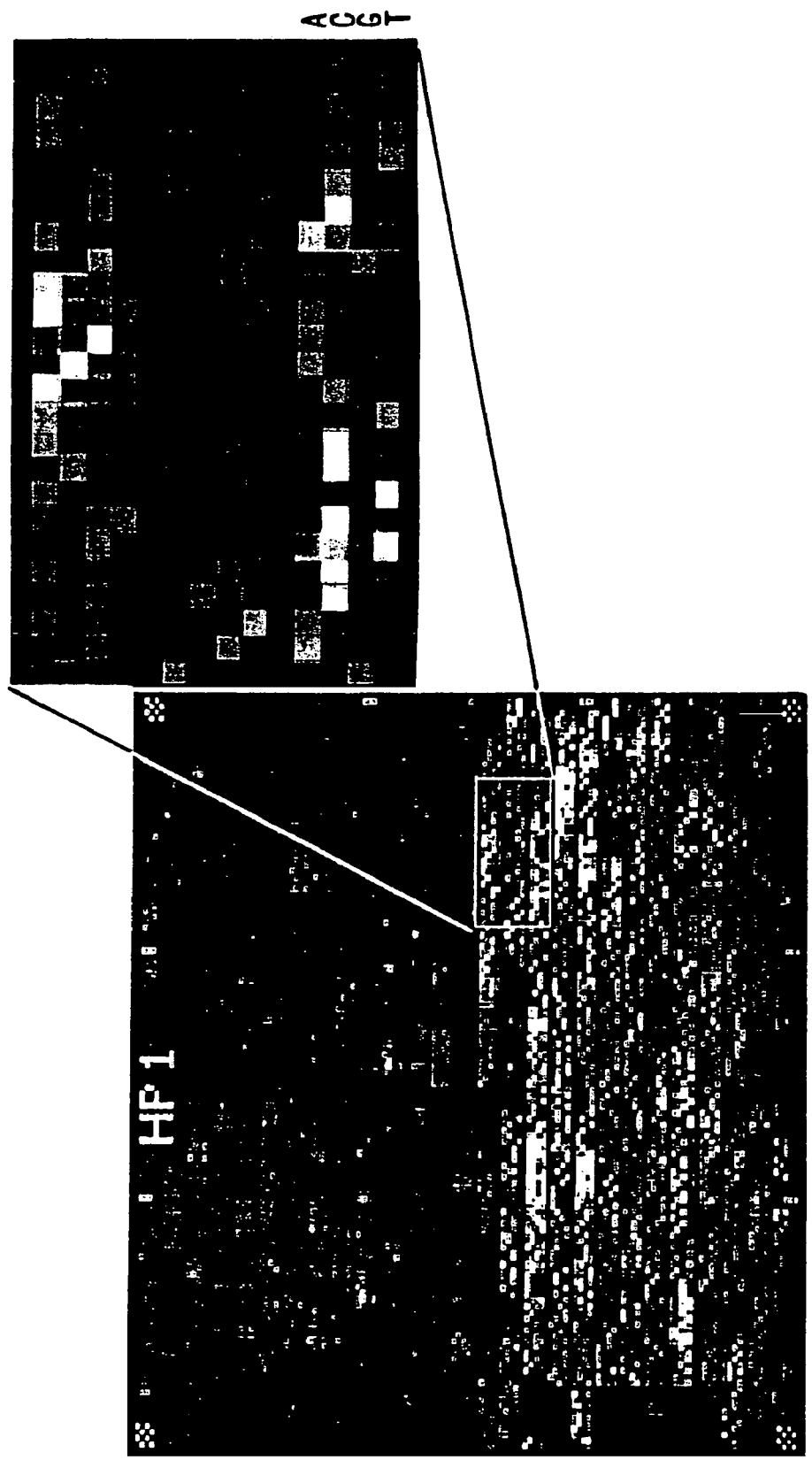
FIG. 15: Hybridization of the chip shown in FIG. 10 to cytochrome P450 2C19.

In a separate experiment, the chip was hybridized to CYP2C19 cDNA, as shown in FIG. 15. The Figure shows that the lower portion of the chip containing the 2C19 tiles is lit. A magnification of part of the hybridization pattern from the basic tiling sequence is shown in the upper right of the Figure. Again, the sequence can be read by eye by comparing the intensities of the four probes forming a column.

III. Modes of Practicing the Invention

A. VLSIPS™ Technology

Figure 16:
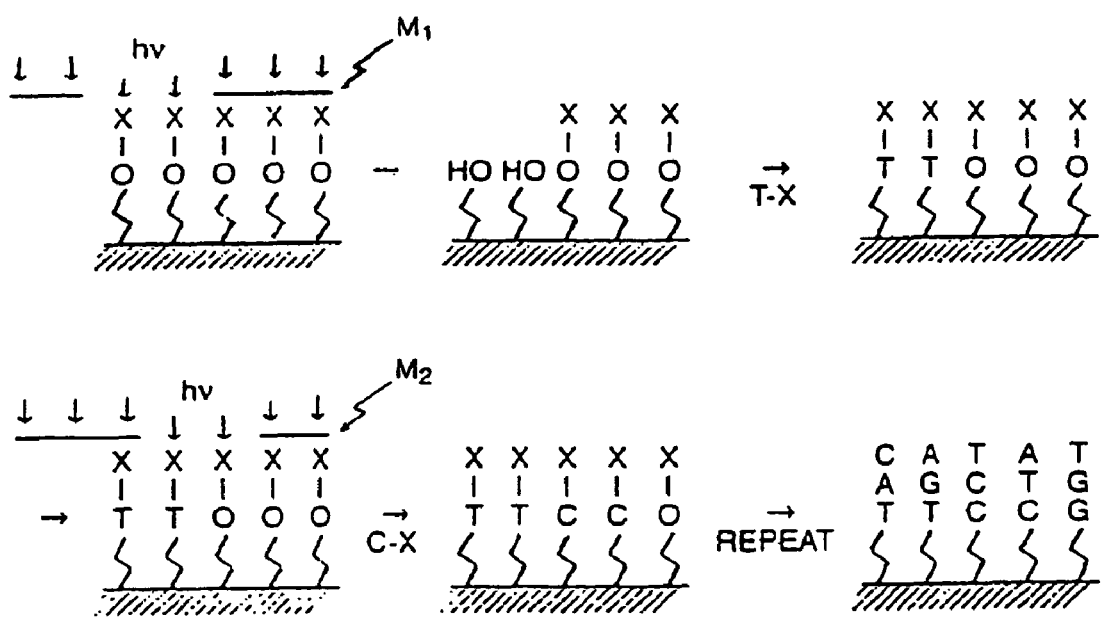
FIG. 16: VLSIPS™ technology applied to the light directed synthesis of oligonucleotides. Light (hv) is shone through a mask (M$_1$) to activate functional groups (—OH) on a surface by removal of a protecting group (X). Nucleoside building blocks protected with photoremovable protecting groups (T-X, C-X) are coupled to the activated areas. By repeating the irradiation and coupling steps, very complex arrays of oligonucleotides can be prepared.

As noted above, the VLSIPS™ technology is described in a number of patent publications and is preferred for making the oligonucleotide arrays of the invention. A brief description of how this technology can be used to make and screen DNA chips is provided in this Example and the accompanying Figures. In the VLSIPS™ method, light is shone through a mask to activate functional (for oligonucleotides, typically an —OH) groups protected with a photoremovable protecting group on a surface of a solid support. After light activation, a nucleoside building block, itself protected with a photoremovable protecting group (at the 5'-OH), is coupled to the activated areas of the support. The process can be repeated, using different masks or mask orientations and building blocks, to prepare very dense arrays of many different oligonucleotide probes. The process is illustrated in FIG. 16; FIG. 17 illustrates how the process can be used to prepare "nucleoside combinatorials" or oligonucleotides synthesized by coupling all four nucleosides to form dimers, trimers and so forth.

New methods for the combinatorial chemical synthesis of peptide, polycarbamate, and oligonucleotide arrays have recently been reported (see Fodor et al., 1991, *Science* 251: 767-773; Cho et al., 1993, *Science* 261: 1303.-1305; and Southern et al., 1992, *Genomics* 13: 1008-10017, each of which is incorporated herein by reference). These arrays, or biological chips (see Fodor et al., 1993, *Nature* 364: 555-556, incorporated herein by reference), harbor specific chemical compounds at precise locations in a high-density, information rich format, and are a powerful tool for the study of biological recognition processes. A particularly exciting application of the array technology is in the field of DNA sequence analysis. The hybridization pattern of a DNA target to an array of shorter oligonucleotide probes is used to gain primary structure information of the DNA target. This format has important applications in sequencing by hybridization, DNA diagnostics and in elucidating the thermodynamic parameters affecting nucleic acid recognition.

Conventional DNA sequencing technology is a laborious procedure requiring electrophoretic size separation of labeled DNA fragments. An alternative approach, termed Sequencing By Hybridization (SBH), has been proposed (Lysov et al., 1988, *Dokl.Akad.Nauk SSSR* 303:1508-1511; Bains et al., *J. Theor. Biol.* 135:303-307; and Drmanac et al., 1989, *Genomics* 4:114-128, incorporated herein by reference and discussed in Description of Related Art, supra). This method uses a set of short oligonucleotide probes of defined sequence to search for complementary sequences on a longer target strand of DNA. The hybridization pattern is used to reconstruct the target DNA sequence. It is envisioned that hybridization analysis of large numbers of probes can be used to sequence long stretches of DNA. In immediate applications of this methodology, a small number of probes can be used to interrogate local DNA sequence. The strategy of SBH can be illustrated by the following example. A 12-mer target DNA sequence, AGCCTAGCTGAA (SEQ ID NO:151), is mixed with a complete set of octanucleotide probes. If only perfect complementarity is considered, five of the 65,536 octamer probes—TCGGATCG, CGGATCGA, GGATCGAC, GATCGACT, and ATCGACTT will hybridize to the target. Alignment of the overlapping sequences from the hybridizing probes reconstructs the complement of the original 12-mer target:

```
     TCGGATCG
      CGGATCGA
       GGATCGAC
        GATCGACT
         ATCGACTT
     TCGGATCGACTT          (SEQ ID NO: 152)
```

Hybridization methodology can be carried out by attaching target DNA to a surface. The target is interrogated with a set of oligonucleotide probes, one at a time (see Strezoska et al., 1991, *Proc. Natl. Acad. Sci. USA* 88:10089-10093, and Drmanac et al., 1993, *Science* 260:1649-1652, each of which is incorporated herein by reference). This approach can be implemented with well established methods of immobilization and hybridization detection, but involves a large number of manipulations. For example, to probe a sequence utilizing a full set of octanucleotides, tens of thousands of hybridization reactions must be performed. Alternatively, SBH can be carried out by attaching probes to a surface in an array format where the identity of the probes at each site is known. The target DNA is then added to the array of probes. The hybridization pattern determined in a single experiment directly reveals the identity of all complementary probes.

As noted above, a preferred method of oligonucleotide probe array synthesis involves the use of light to direct the synthesis of oligonucleotide probes in high-density, miniaturized arrays. Photolabile 5'-protected N-acyl-deoxynucleoside phosphoramidites, surface linker chemistry, and versatile combinatorial synthesis strategies have been developed for this technology. Matrices of spatially-defined oligonucleotide probes have been generated, and the ability to use these arrays to identify complementary sequences has been demonstrated by hybridizing fluorescent labeled oligonucleotides to the DNA chips produced by the methods. The hybridization pattern demonstrates a high degree of base specificity and reveals the sequence of oligonucleotide targets.

Figure 18:
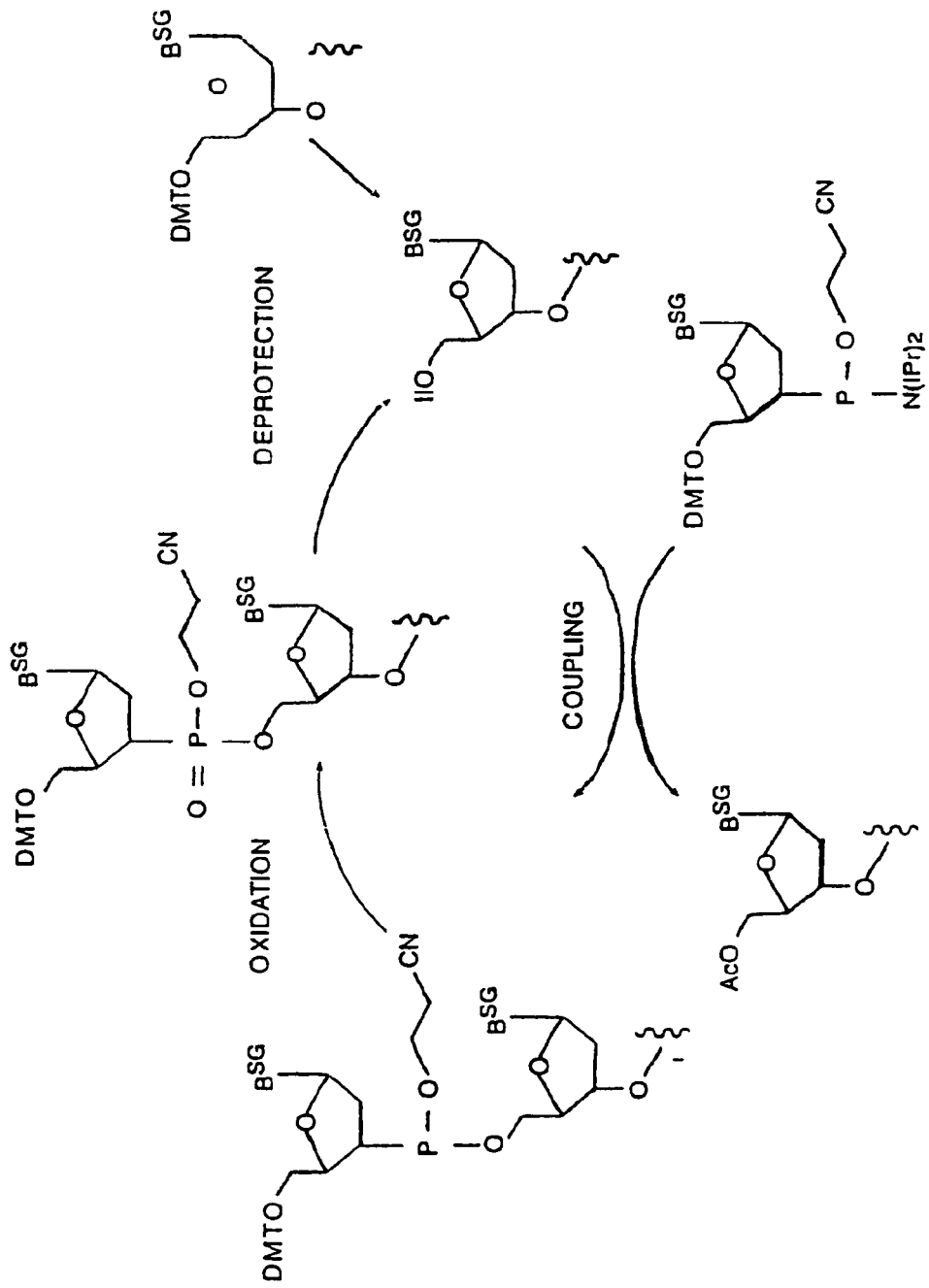
FIG. 18: Deprotection, coupling, and oxidation steps of solid phase DNA synthesis method.

The basic strategy for light-directed oligonucleotide synthesis (1) is outlined in FIG. 18. The surface of a solid support modified with photolabile protecting groups (X) is illuminated through a photolithographic mask, yielding reactive hydroxyl groups in the illuminated regions. A 3'-O-phosphoramidite activated deoxynucleoside (protected at the 5'-hydroxyl with a photolabile group) is then presented to the surface and coupling occurs at sites that were exposed to light. Following capping, and oxidation, the substrate is rinsed and the surface illuminated through a second mask, to expose additional hydroxyl groups for coupling. A second 5'-protected, 3'-O-phosphoramidite activated deoxynucleoside is presented to the surface. The selective photodeprotection and coupling cycles are repeated until the desired set of products is obtained.

Light directed chemical synthesis lends itself to highly efficient synthesis strategies which will generate a maximum number of compounds in a minimum number of chemical steps. For example, the complete set of $4^n$ polynucleotides (length n), or any subset of this set can be produced in only 4×n chemical steps. See FIG. 17. The patterns of illumination and the order of chemical reactants ultimately define the products and their locations. Because photolithography is used, the process can be miniaturized to generate high-density arrays of oligonucleotide probes. For an example of the nomenclature useful for describing such arrays, an array containing all possible octanucleotides of dA and dT is written as $(A+T)^8$. Expansion of this polynomial reveals the identity of all 256 octanucleotide probes from AAAAAAA to TTTTTTTT. A DNA array composed of complete sets of dinucleotides is referred to as having a complexity of 2. The array given by $(A+T+C+G)8$ is the full 65,536 octanucleotide array of complexity four. Computer-aided methods of laying down predesigned arrays of probes using VLSIPS™ technology are described in commonly-assigned co-pending application U.S. Ser. No. 08/249,188, filed May 24, 1994 (incorporated by reference in its entirety for all purposes).

In a variation of the VLSIPS™ methods, multiple copies of an array of probes are synthesized simultaneously. The multiple copies are effectively stacked in a pile during the synthesis process in a manner such that each copy is accessible to irradiation. For example, synthesis can occur through the volume of a slab of polymer gel that is transparent to the source of radiation used to remove photoprotective groups. Suitable polymers are described in U.S. Ser. No. 08/431,196, filed Apr. 27, 1995 (incorporated by reference in its entirety for all purposes). For example, a polymer formed from a 90:10% w/w mixture of acrylamide and N-2-aminoethylacrylamide is suitable.

After synthesis, the gel is sliced into thin layers (e.g., with a microtome). Each layer is attached to a glass substrate to constitute a separate chip. Alternatively, a pile can be formed from layers of gel separated by layers of a transparent substance that can be mechanically or chemically removed after synthesis has occurred. Using these methods, up to about 10, 100 or 1000 identical arrays can be synthesized simultaneously.

To carry out hybridization of DNA targets to the probe arrays, the arrays are mounted in a thermostatically controlled hybridization chamber. Fluorescein labeled DNA targets are injected into the chamber and hybridization is allowed to proceed for 5 min to 24 hr. The surface of the matrix is scanned in an epifluorescence microscope (Zeiss Axioscop 20) equipped with photon counting electronics using 50-100 µW of 488 nm excitation from an Argon ion laser (Spectra Physics Model 2020). Measurements may be made with the target solution in contact with the probe matrix or after washing. Photon counts are stored and image files are presented after conversion to an eight bit image format. See FIG. 21.

When hybridizing a DNA target to an oligonucleotide array, N=Lt–(Lp–1) complementary hybrids are expected, where N is the number of hybrids, Lt is the length of the DNA target, and Lp is the length of the oligonucleotide probes on the array. For example, for an 11-mer target hybridized to an octanucleotide array, N=4. Hybridizations with mismatches at positions that are 2 to 3 residues from either end of the probes will generate detectable signals. Modifying the above expression for N, one arrives at a relationship estimating the number of detectable hybridizations (Nd) for a DNA target of length Lt and an array of complexity C. Assuming an average of S positions giving signals above background:

$$Nd=(1+5(C-1))[Lt-(Lp-1)].$$

Arrays of oligonucleotides can be efficiently generated by light-directed synthesis and can be used to determine the identity of DNA target sequences. Because combinatorial strategies are used, the number of compounds increases exponentially while the number of chemical coupling cycles increases only linearly. For example, synthesizing the complete set of $4^8$ (65,536) octanucleotides will add only four hours to the synthesis for the 16 additional cycles. Furthermore, combinatorial synthesis strategies can be implemented to generate arrays of any desired composition. For example, because the entire set of dodecamers ($4^{12}$) can be produced in 48 photolysis and coupling cycles ($b^n$ compounds requires bxn cycles), any subset of the dodecamers (including any subset of shorter oligonucleotides) can be constructed with the correct lithographic mask design in 48 or fewer chemical coupling steps. In addition, the number of compounds in an array is limited only by the density of synthesis sites and the overall array size. Recent experiments have demonstrated hybridization to probes synthesized in 25 µm sites. At this resolution, the entire set of 65,536 octanucleotides can be placed in an array measuring 0.64 cm square, and the set of 1,048,576 dodecanucleotides requires only a 2.56 cm array.

Genome sequencing projects will ultimately be limited by DNA sequencing technologies. Current sequencing methodologies are highly reliant on complex procedures and require substantial manual effort. Sequencing by hybridization has the potential for transforming many of the manual efforts into more efficient and automated formats. Light-directed synthesis is an efficient means for large scale production of miniaturized arrays for SBH. The oligonucleotide arrays are not limited to primary sequencing applications. Because single base changes cause multiple changes in the hybridization pattern, the oligonucleotide arrays provide a powerful means to check the accuracy of previously elucidated DNA sequence, or to scan for changes within a sequence. In the case of octanucleotides, a single base change in the target DNA results in the loss of eight complements, and generates eight new complements. Matching of hybridization patterns may be useful in resolving sequencing ambiguities from standard gel techniques, or for rapidly detecting DNA mutational events. The potentially very high information content of light-directed oligonucleotide arrays will change genetic diagnostic testing. Sequence comparisons of hundreds to thousands of different genes will be assayed simultaneously instead of the current one, or few at a time format. Custom arrays can also be constructed to contain genetic markers for the rapid identification of a wide variety of pathogenic organisms.

Oligonucleotide arrays can also be applied to study the sequence specificity of RNA or protein-DNA interactions. Experiments can be designed to elucidate specificity rules of non Watson-Crick oligonucleotide structures or to investigate the use of novel synthetic nucleoside analogs for antisense or triple helix applications. Suitably protected RNA monomers may be employed for RNA synthesis. The oligonucleotide arrays should find broad application deducing the thermodynamic and kinetic rules governing formation and stability of oligonucleotide complexes.

Figure 19:
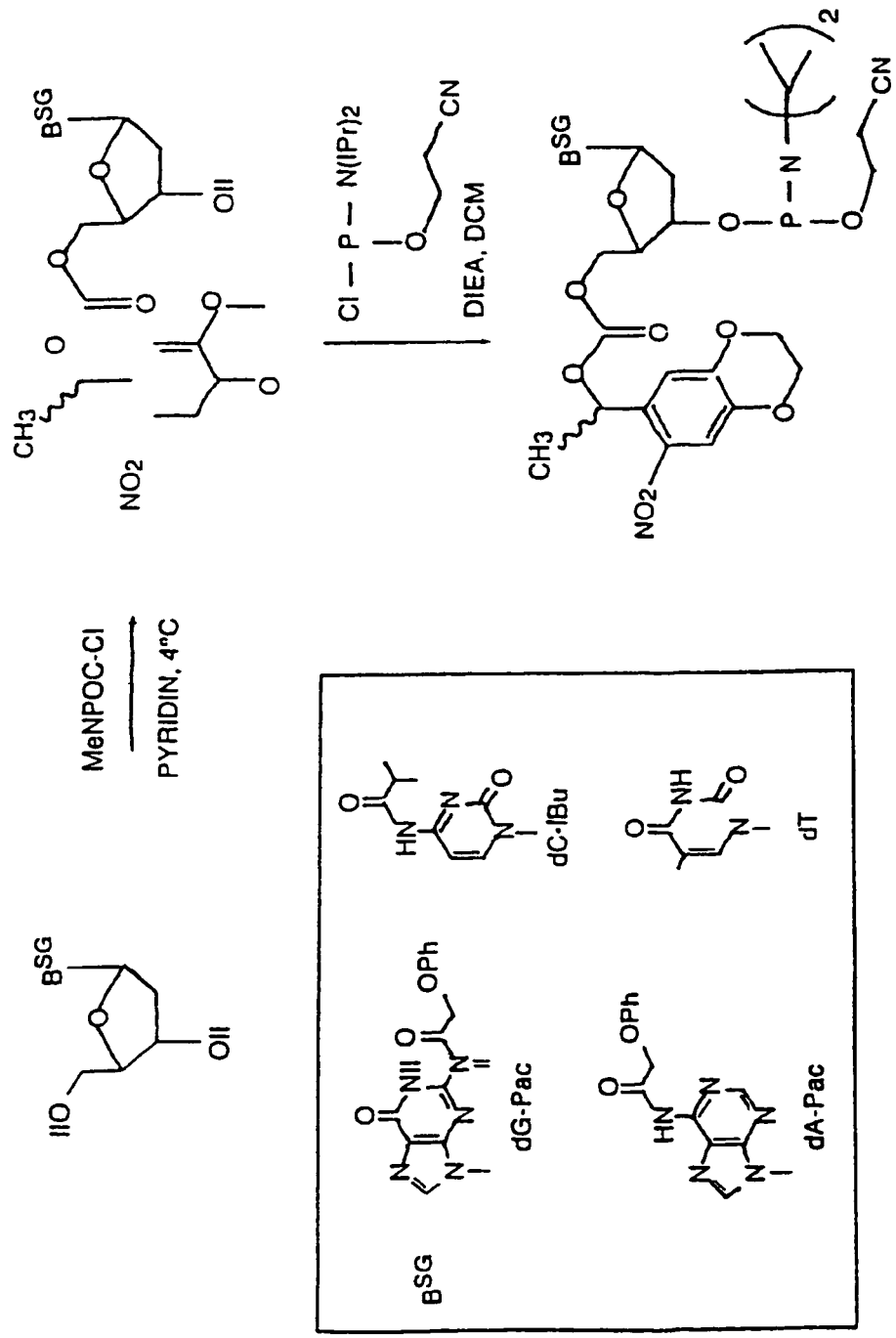
FIG. 19: An illustrative synthesis route for the nucleoside building blocks used in the VLSIPS™ method.
Figure 20:
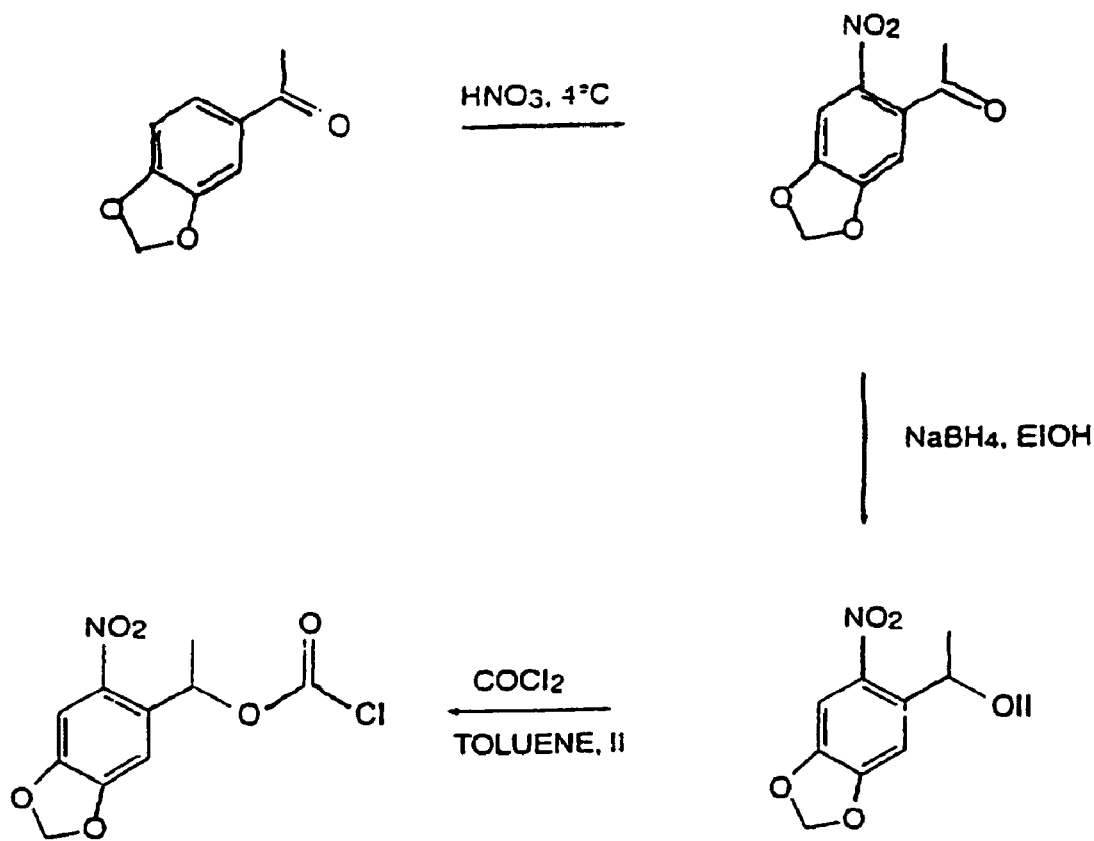
FIG. 20: A preferred photoremovable protecting group, MeNPOC, and preparation of the group in active form.

Other than the use of photoremovable protecting groups, the nucleoside coupling chemistry is very similar to that used routinely today for oligonucleotide synthesis. FIG. 18 shows the deprotection, coupling, and oxidation steps of a solid phase DNA synthesis method. FIG. 19 shows an illustrative synthesis route for the nucleoside building blocks used in the method. FIG. 20 shows a preferred photoremovable protecting group, MeNPOC, and how to prepare the group in active form. The procedures described below show how to prepare these reagents. The nucleoside building blocks are 5'-MeNPOC-THYMIDINE-3'-OCEP; 5'-MeNPOC-N$^4$-t-BUTYL PHENOXYACETYL-DEOXY-CYTIDINE-3'-OCEP; 5'-MeNPOC-N$^4$-t-BUTYL PHENOXYACETYL-DEOXYGUANOSINE-3'-OCEP; and 5'-MeNPOC-N$^4$-t-BUTYL PHENOXYACETYL-DEOXYADENOSINE-3'-OCEP.

1. Preparation of 4,5-methylenedioxy-2-nitroacetophenone

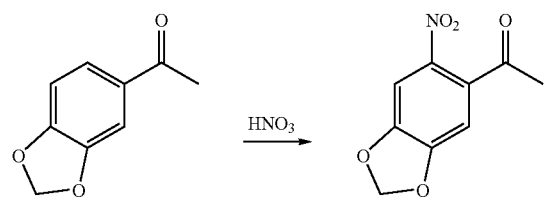

A solution of 50 g (0.305 mole) 3,4-methylenedioxy-acetophenone (Aldrich) in 200 mL glacial acetic acid was added dropwise over 30 minutes to 700 mL of cold (2-4° C.) 70% HNO$_3$ with stirring (NOTE: the reaction will overheat without external cooling from an ice bath, which can be dangerous and lead to side products). At temperatures below 0° C., however, the reaction can be sluggish. A temperature of 3-5° C. seems to be optimal). The mixture was left stirring for another 60 minutes at 3-5° C., and then allowed to approach ambient temperature. Analysis by TLC (25% EtOAc in hexane) indicated complete conversion of the starting material within 1-2 hr. When the reaction was complete, the mixture was poured into ~3 liters of crushed ice, and the resulting yellow solid was filtered off, washed with water and then suction-dried. Yield ~53 g (84%), used without further purification.

2. Preparation of 1-(4,5-Methylenedioxy-2-nitrophenyl)ethanol

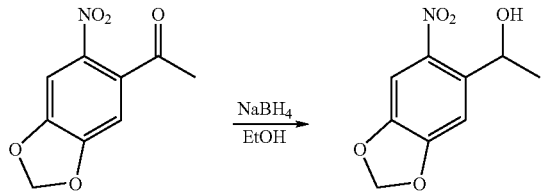

Sodium borohydride (10g; 0.27 mol) was added slowly to a cold, stirring suspension of 53 g (0.25 mol) of 4,5-methylenedioxy-2-nitroacetophenone in 400 mL methanol. The temperature was kept below 10° C. by slow addition of the NaBH₄ and external cooling with an ice bath. Stirring was continued at ambient temperature for another two hours, at which time TLC (CH₂Cl₂) indicated complete conversion of the ketone. The mixture was poured into one liter of ice-water and the resulting suspension was neutralized with ammonium chloride and then extracted three times with 400 mL CH₂Cl₂ or EtOAc (the product can be collected by filtration and washed at this point, but it is somewhat soluble in water and this results in a yield of only ~60%). The combined organic extracts were washed with brine, then dried with MgSO₄ and evaporated. The crude product was purified from the main byproduct by dissolving it in a minimum volume of CH₂Cl₂ or THF(~175 ml) and then precipitating it by slowly adding hexane (1000 ml) while stirring (yield 51g; 80% overall). It can also be recrystallized (e.g., toluene-hexane), but this reduces the yield.

3. Preparation of 1-(4,5-methylenedioxy-2-nitrophenyl)ethyl chloroformate (MeNPOC-Cl)

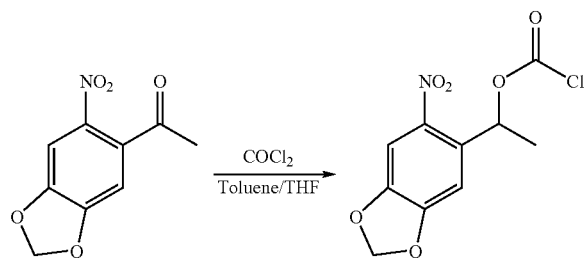

Phosgene (500 mL of 20% w/v in toluene from Fluka: 965 mmole; 4 eq.) was added slowly to a cold, stirring solution of 50 g (237 mmole; 1 eq.) of 1-(4,5-methylenedioxy-2-nitrophenyl)ethanol in 400 mL dry THF. The solution was stirred overnight at ambient temperature at which point TLC.(20% Et₂O/hexane) indicated >95% conversion. The mixture was evaporated (an oil-less pump with downstream aqueous NaOH trap is recommended to remove the excess phosgene) to afford a viscous brown oil. Purification was effected by flash chromatography on a short (9×13 cm) column of silica gel eluted with 20% Et₂O/hexane. Typically 55 g (85%) of the solid yellow MeNPOC-Cl is obtained by this procedure. The crude material has also been recrystallized in 2-3 crops from 1:1'ether/hexane. On this scale, ~100 ml is used for the first crop, with a few percent THF added to aid dissolution, and then cooling overnight at −20° C. (this procedure has not been optimized). The product should be stored desiccated at −20° C.

4. Synthesis of 5'- Menpoc-2'-deoxynucleoside-3'-(N,N-diisopropyl 2-cyanoethyl phosphoramidites

(a) 5'-MeNPOC-Nucleosides

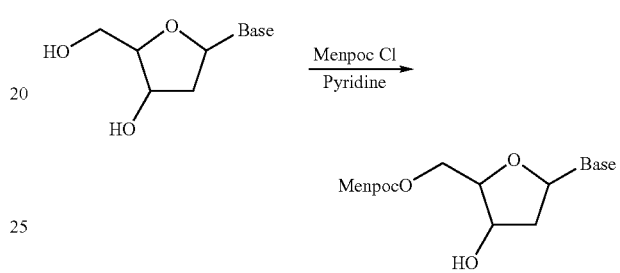

Base=THYMIDINE (T); N-4-ISOBUTYRYL 2'-DEOXYCYTIDINE (ibu-dC); N-2-PHENOXYACETYL 2'DEOXYGUANOSINE (PAC-dG); and N-6-PHENOXYACETYL 2'DEOXYADENOSINE (PAC-dA)

All four of the 5'-MeNPOC nucleosides were prepared from the base-protected 2'-deoxynucleosides by the following procedure. The protected 2'-deoxynucleoside (90 mmole) was dried by co-evaporating twice with 250 mL anhydrous pyridine. The nucleoside was then dissolved in 300 mL anhydrous pyridine (or 1:1 pyridine/DMF, for the dG$^{PAC}$ nucleoside) under argon and cooled to ~2° C. in an ice bath. A solution of 24.6 g (90 mmole) MeNPOC-Cl in 100 mL dry THF was then added with stirring over 30 minutes. The ice bath was removed, and the solution allowed to stir overnight at room temperature (TLC: 5-10% MeOH in CH₂Cl₂; two diastereomers). After evaporating the solvents under vacuum, the crude material was taken up in 250 mL ethyl acetate and extracted with saturated aqueous NaHCO₃ and brine. The organic phase was then dried over Na₂SO₄, filtered and evaporated to obtain a yellow foam. The crude products were finally purified by flash chromatography (9×30 cm silica gel column eluted with a stepped gradient of 2%-6% MeOH in CH₂Cl₂). Yields of the purified diastereomeric mixtures are in the range of 65-75%.

(b) 5'-Menpoc-2'-deoxynucleoside-3'-(N,N-diisopropyl 2-cyanoethyl phosphoramidites)

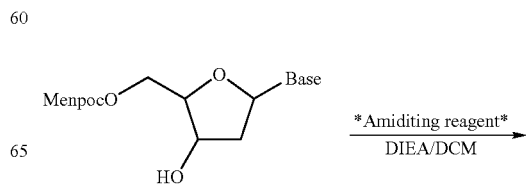

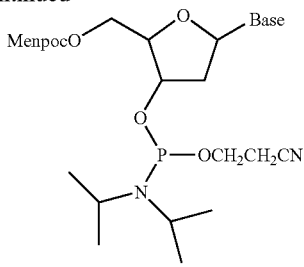

The four deoxynucleosides were phosphitylated using either 2-cyanoethyl-N,N-diisopropyl chlorophosphoramidite, or 2-cyanoethyl- N,N,N',N'-tetraisopropylphosphorodiamidite. The following is a typical procedure. Add 16.6 g (17.4 ml; 55 mmole) of 2- cyanoethyl-N,N,N',N'-tetraisopropylphosphoro-diamidite to a solution of 50 mmole 5'-MeN-POC-nucleoside and 4.3 g (25 mmole) diisopropylammonium tetrazolide in 250 mL dry $CH_2Cl_2$ under argon at ambient temperature. Continue stirring for 4-16 hours (reaction monitored by TLC: 45:45:10 hexane/$CH_2Cl_2$/$Et_3N$). Wash the organic phase with saturated aqueous $NaHCO_3$ and brine, then dry over $Na_2SO_4$, and evaporate to dryness. Purify the crude amidite by flash chromatography (9×25 cm silica gel column eluted with hexane/$CH_2Cl_2$/TEA—45:45:10 for A, C, T; or 0:90:10 for G). The yield of purified amidite is about 90%.

B. Preparation of Labeled DNA/Hybridization to Array

1. PCR

PCR amplification reactions are typically conducted in a mixture composed of, per reaction: 1 µl genomic DNA; 10 µl each primer (10 pmol/µl stocks); 10 µl 10×PCR buffer (100 mM Tris.Cl pH 8.5, 500 mM KCl, 15 mM $MgCl_2$); 10 µl 2 mM dNTPs (made from 100 mM dNTP stocks); 2.5 U Taq polymerase (Perkin Elmer AmpliTaq™, 5 U/µl); and $H_2O$ to 100 µl. The cycling conditions are usually 40 cycles (94° C. 45 sec, 55° C. 30 sec, 72° C. 60 sec) but may need to be varied considerably from sample type to sample type. These conditions are for 0.2 mL thin wall tubes in a Perkin Elmer 9600 thermocycler. See Perkin Elmer 1992/93 catalogue for 9600 cycle time information. Target, primer length and sequence composition, among other factors, may also affect parameters.

For products in the 200 to 1000 bp size range, check 2 µl of the reaction on a 1.5% 0.5×TBE agarose gel using an appropriate size standard (phiX174 cut with HaeIII is convenient). The PCR reaction should yield several picomoles of product. It is helpful to include a negative control (i.e., 1 µl TE instead of genomic DNA) to check for possible contamination. To avoid contamination, keep PCR products from previous experiments away from later reactions, using filter tips as appropriate. Using a set of working solutions and storing master solutions separately is helpful, so long as one does not contaminate the master stock solutions.

For simple amplifications of short fragments from genomic DNA it is, in general, unnecessary to optimize $Mg^{2+}$ concentrations. A good procedure is the following: make a master mix minus enzyme; dispense the genomic DNA samples to individual tubes or reaction wells; add enzyme to the master mix; and mix and dispense the master solution to each well, using a new filter tip each time.

2. Purification

Removal of unincorporated nucleotides and primers from PCR samples can be accomplished using the Promega Magic PCR Preps DNA purification kit. One can purify the whole sample, following the instructions supplied with the kit (proceed from section IIIB, 'Sample preparation for direct purification from PCR reactions'). After elution of the PCR product in 50 µl of TE or $H_2O$, one centrifuges the eluate for 20 sec at 12,000 rpm in a microfuge and carefully transfers 45 µl to a new microfuge tube, avoiding any visible pellet. Resin is sometimes carried over during the elution step. This transfer prevents accidental contamination of the linear amplification reaction with 'Magic PCR' resin. Other methods, e.g., size exclusion chromatography, may also be used.

3. Linear Amplification

In a 0.2 mL thin-wall PCR tube mix: 4 µl purified PCR product; 2 µl primer (10 pmol/µl); 4. µl 10×PCR buffer; 4 µl dNTPs (2 mM dA, dC, dG, 0.1 mM dT); 4 µl 0.1 mM dUTp; 1 µl 1 mM fluorescein dUTP (Amersham RPN 2121); 1 U Taq polymerase (Perkin Elmer, 5 U/µl); and add H2O to 40 µl. Conduct 40 cycles (92° C. 30 sec, 55° C. 30 sec, 72° C. 90 sec) of PCR. These conditions have been used to amplify a 300 nucleotide mitochondrial DNA fragment but are applicable to other fragments. Even in the absence of a visible product band on an agarose gel, there should still be enough product to give an easily detectable hybridization signal. If one is not treating the DNA with uracil DNA glycosylase (see Section 4), dUTP can be omitted from the reaction.

4. Fragmentation

Purify the linear amplification product using the Promega Magic PCR Preps DNA purification kit, as per Section 2 above. In a 0.2 mL thin-wall PCR tube mix: 40 µl purified labeled DNA; 4 µl 10×PCR buffer; and 0.5 µl uracil DNA glycosylase (BRL 1 U/µl). Incubate the mixture 15 min at 37° C., then 10 min at. 97° C.; store at −20° C. until ready to use.

5. Hybridization, Scanning & Stripping

A blank scan of the slide in hybridization buffer only is helpful to check that the slide is ready for use. The buffer is removed from the flow cell and replaced with 1 ml of (fragmented) DNA in hybridization buffer and mixed well.

Optionally, standard hybridization buffer can be supplemented with tetramethylammonium chloride (TMACL) or betaine (N,N,N-trimethylglycine; $(CH3)_3N+CH_2COO^-$) to improve discrimination between perfectly matched targets and single-base mismatches. Betaine is zwitterionic at neutral pH and alters the composition-dependent stability of nucleic acids without altering their polyelectrolyte behavior. Betaine is preferably used at a concentration between 1 and 10 M and, optimally, at about 5 M. For example, 5 M betaine in 2×SSPE is suitable. Inclusion of betaine at this concentration lowers the average hybridization signal about four fold, but increases the discrimination between matched and mismatched probes.

Figure 21:
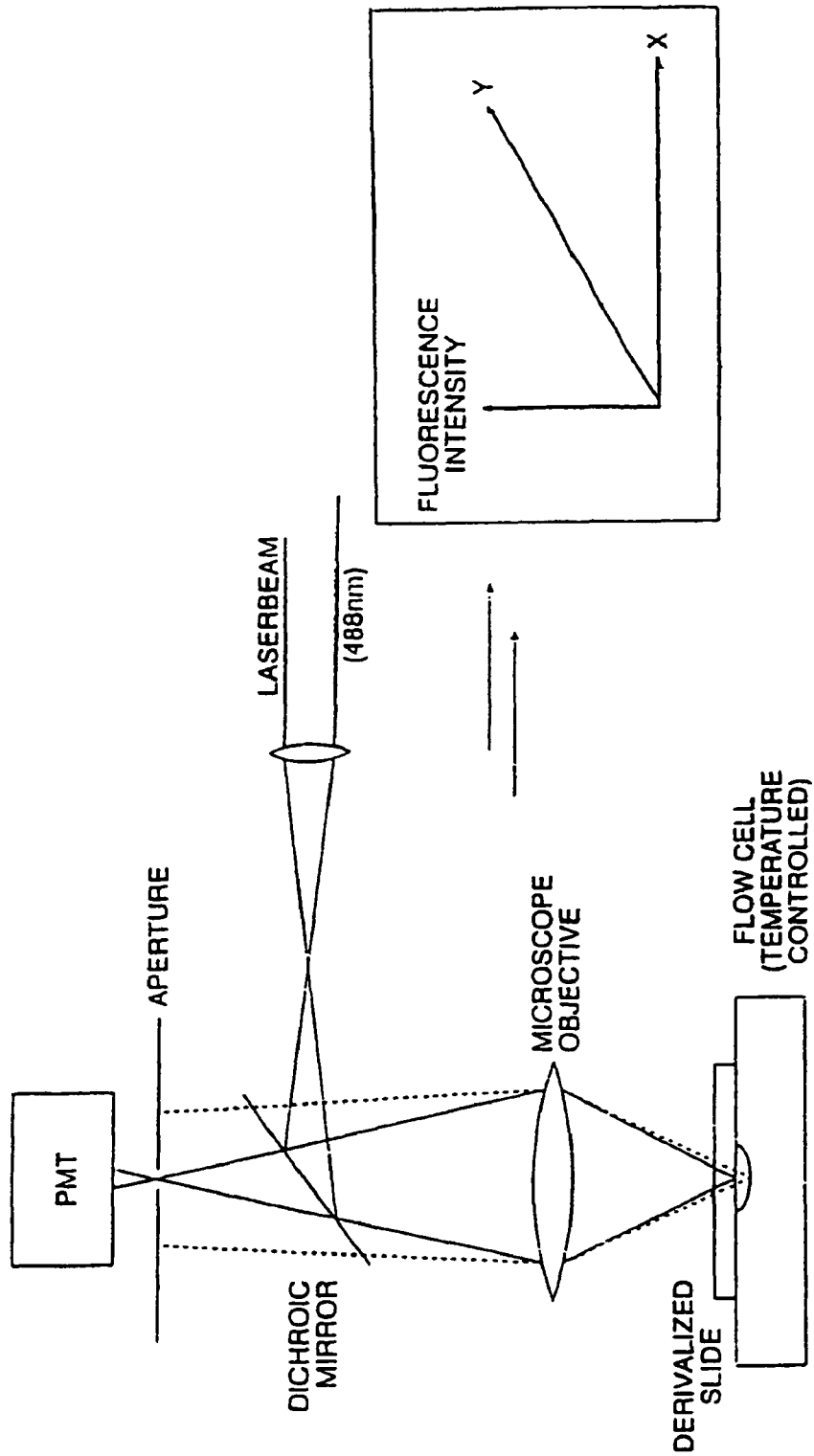
FIG. 21: Detection system for scanning a DNA chip.

The scan is performed in the presence of the labeled target. FIG. 21 illustrates an illustrative detection system for scanning a DNA chip. A series of scans at 30 min intervals using a hybridization temperature of 25° C. yields a very clear signal, usually in at least 30 min to two hours, but it may be desirable to hybridize longer, i.e., overnight. Using a-laser power of 50 µW and 50 µm pixels, one should obtain maximum counts in the range of hundreds to low thousands/pixel for a new slide. When finished, the slide can be stripped using 50% formamide. rinsing well in deionized $H_2O$, blowing dry, and storing at room temperature.

C. Preparation of Labeled RNA/Hybridization to Array

1. Tagged Primers

The primers used to amplify the target nucleic acid should have promoter sequences if one desires to produce RNA from the amplified nucleic acid. Suitable promoter sequences are shown below and include:

(1) the T3 promoter sequence:
5'-CGGAATTAACCCTCACTAAAGG         (SEQ ID NO: 153)

5'-AATTAACCCTCACTAAAGGGAG;        (SEQ ID NO: 154)

(2) the T7 promoter sequence:
5' TAATACGACTCACTATAGGGAG;        (SEQ ID NO: 155)
and
(3) the SP6 promoter sequence:
5' ATTTAGGTGACACTATAGAA.          (SEQ ID NO: 156)

The desired promoter sequence is added to the 5' end of the PCR primer. It is convenient to add a different promoter to each primer of a PCR primer pair so that either strand may be transcribed from a single PCR product.

Synthesize PCR primers so as to leave the DMT group on. DMT-on purification is unnecessary for PCR but appears to be important for transcription. Add 25 µl 0.5M NaOH to collection vial prior to collection of oligonucleotide to keep the DMT group on. Deprotect using standard chemistry—55° C. overnight is convenient.

HPLC purification is accomplished by drying down the oligonucleotides, resuspending in 1 mL 0.1 M TEAA (dilute 2.0 M stock in deionized water, filter through 0.2 micron filter) and filter through 0.2 micron filter. Load 0.5 mL on reverse phase HPLC (column can be a Hamilton PRP-1 semi-prep, #79426). The gradient is 0->50% $CH_3CN$ over 25 min (program 0.2 mol.prep.0-50, 25 min). Pool the desired fractions, dry down, resuspend in 200 µl 80% HAc. 30 min RT. Add 200 µl EtOH; dry down. Resuspend in 200 µl $H_2O$, plus 20 µl NaAc pH5.5, 600 µl EtOH. Leave 10 min on ice; centrifuge 12,000 rpm for 10 min in microfuge. Pour off supernatant. Rinse pellet with 1 mL EtOH, dry, resuspend in 200 µl H2O. Dry, resuspend in 200 µl TE. Measure A260, prepare a 10. pmol/µl solution in TE (10 mM Tris.Cl pH 8.0, 0.1 mM EDTA). Following HPLC purification of a 42 mer, a yield in the vicinity of 15 nmol from a 0.2 µmol scale synthesis is typical.

2. Genomic DNA Preparation

Add 500 µl (10 MM Tris.Cl pH8.0, 10 mM EDTA, 100 mm NaCl, 2% (w/v) SDS, 40 mM DTT, filter sterilized) to the sample. Add 1.25 µl 20 mg/ml proteinase K (Boehringer) Incubate at 55° C. for 2 hours, vortexing once or twice. Perform 2×0.5 mL 1:1 phenol:$CHCl_3$ extractions. After each extraction, centrifuge 12,000 rpm 5 min in a microfuge and recover 0.4 mL supernatant. Add 35 µl NaAc pH5.2 plus 1 mL EtOH. Place sample on ice 45 min; then centrifuge 12,000 rpm 30 min, rinse, air dry 30 min, and resuspend in 100 µl TE.

3. PCR

PCR is performed in a mixture containing, per reaction: 1 µl genomic DNA; 4 µl each primer (10 pmol/µl stocks); 4 µl 10×PCR buffer (100 mM Tris.Cl pHB.5,500 mM KCl, 15 mM $MgCl_2$); 4 µl 2 mM dNTPs (made from 100 mM dNTP stocks); 1 U Taq polymerase (Perkin Elmer,. 5 U/µl); $H_2O$ to 40 µl. About 40 cycles (94° C. 30 sec, 55° C. 30 sec, 72° C. 30 sec) are performed, but cycling conditions may need to be varied. These conditions are for 0.2 mL thin wall tubes in Perkin Elmer 9600. For products in the 200 to 1000 bp size range, check 2 µl of the reaction on a 1.5% 0.5×TBE agarose gel using an appropriate size standard. For larger or smaller volumes (20-100 µl), one can use the same amount of genomic DNA but adjust the other ingredients accordingly.

4. In Vitro Transcription

Mix: 3 µl PCR product; 4 µl 5×buffer; 2 µl DTT; 2.4 µl 10 mM rNTPs (100 mM solutions from Pharmacia); 0.48 µl 10 mM fluorescein-UTP (Fluorescein-12-UTP, 10 mM solution, from Boehringer Mannheim); 0.5 µl RNA polymerase (Promega T3 or T7 RNA polymerase); and add H2O to 20 µl. Incubate at 37° C. for 3 h. Check 2 µl of the reaction on a 1.5% 0.5×TBE agarose gel using a size standard. 5×buffer is 200 mM Tris pH 7.5, 30 MM MgCl2, 10 mM spermidine, 50 mM NaCl, and 100 mM DTT (supplied with enzyme). The PCR product needs no purification and can be added directly the transcription mixture. A 20 µl reaction is suggested for an initial test experiment and hybridization; a 100 µl reaction is considered "preparative" scale (the reaction can be scaled up to obtain more target). The amount of PCR product to add is variable; typically a PCR reaction will yield several picomoles of DNA. If the PCR reaction does not produce that much target, then one should increase the amount of DNA added to the transcription reaction (as well as optimize the PCR). The ratio of fluorescein-UTP to UTP suggested above is 1:5, but ratios from 1:3 to 1:10—all work well. One can also label with biotin-UTP and detect with streptavidin-FITC to obtain similar results as with fluorescein-UTP detection.

For nondenaturing agarose gel electrophoresis of RNA, note that the RNA band will normally migrate somewhat faster than the DNA template band, although sometimes the two bands will comigrate. The temperature of the gel can effect the migration of the RNA band. The RNA produced from in vitro transcription is quite stable and can be stored for months (at least) at −20° C. without any evidence of degradation. It can be stored in unsterilized 6×SSPE 0.1% triton X-100 at −20° C. for days (at least) and reused twice (at least) for hybridization, without taking any special precautions in preparation or during use. RNase contamination should of course be avoided. When extracting RNA from cells, it is preferable to work very rapidly and to use strongly denaturing conditions. Avoid using glassware previously contaminated with RNases. Use of new disposable plasticware (not necessarily sterilized) is preferred, as new plastic tubes, tips, etc., are essentially RNase free. Treatment with DEPC or autoclaving is typically not necessary.

5. Fragmentation

Heat, transcription mixture at 94 degrees for forty min. The extent of fragmentation is controlled by varying $Mg^{2+}$ concentration (30 mM is typical), temperature, and duration of heating.

6. Hybridization, Scanning & Stripping

A blank scan of the slide in hybridization buffer only is helpful to check that the slide is ready for use. The buffer is removed from the flow cell and replaced with 1 mL of (hydrolysed) RNA in hybridization buffer and mixed well. Incubate for 15-30 min at 18° C. Remove the hybridization solution, which can be saved for subsequent experiments. Rinse the flow cell 4-5 times with fresh changes of 6×SSPE 0.1% Triton X-100, equilibrated to 18° C. The rinses can be performed rapidly, but it is important to empty the flow cell before each new rinse and to mix the liquid in the cell thoroughly. A series of scans at 30 min intervals using a hybridization temperature of 25° C. yields a very clear signal, usually in at least 30 min to two hours, but it may be desirable to hybridize longer, i.e., overnight. Using a laser power of 50 µW and 50 µm pixels, one should obtain maximum counts in the range of hundreds to low thousands/pixel for a new slide. When finished, the slide can be stripped using warm water.

These conditions are illustrative and assume a probe length of ~15 nucleotides. The stripping conditions suggested are fairly severe, but some signal may remain on the slide if the washing is not stringent. Nevertheless, the counts remaining after the wash should be very low in comparison to the signal in presence of target RNA. In some cases, much gentler stripping conditions are effective. The lower the hybridization temperature and the longer the duration of hybridization, the more difficult it is to strip the slide. Longer targets may be more difficult to strip than shorter targets.

7. Amplification of Signal

A variety of methods can be used to enhance detection of labelled targets bound to a probe on the array. In one embodiment, the protein MutS (from *E. coli*) or equivalent proteins such as yeast MSH1,. MSH2, and MSH3; mouse Rep-3, and Streptococcus Hex-A, is used in conjunction with target hybridization to detect probe-target complex that contain mismatched base pairs. The protein, labeled directly or indirectly, can be added to the chip during or after hybridization of target nucleic acid, and differentially binds to homo- and heteroduplex nucleic acid. A wide variety of dyes and other labels can be used for similar purposes. For instance, the dye YOYO-1 is known to bind preferentially to nucleic acids containing sequences comprising runs of 3 or more G residues.

8. Detection of Repeat Sequences

In some circumstances, i.e., target nucleic acids with repeated sequences or with high G/C content, very long probes are sometimes required for optimal detection. In one embodiment for detecting specific sequences in a target nucleic acid with a DNA chip, repeat sequences are detected as follows. The chip comprises probes of length sufficient to extend into the repeat region varying distances from each end. The sample, prior to hybridization, is treated with a labelled oligonucleotide that is complementary to a repeat region but shorter than the full length of the repeat. The target nucleic is labelled with a second, distinct label. After hybridization, the chip is scanned for probes that have bound both the labelled target and the labelled oligonucleotide probe; the presence of such bound probes shows that at least two repeat sequences are present.

While the foregoing invention has been described in some detail for purposes of clarity and understanding, it will be clear to one skilled in the art from a reading of this disclosure that various changes in form and detail can be made without departing from the true scope of the invention. All publications and patent documents cited in this application are incorporated by reference in their entirety for all purposes to the same extent as if each individual publication or patent document were so individually denoted.

What is claimed is:

1. An array of oligonucleotide probes immobilized on a solid support, the array comprising at least two sets of oligonucleotide probes, (1) a first probe set comprising a plurality of probes, each probe comprising a segment of at least three nucleotides exactly complementary to a subsequence of a reference sequence, the segment including at least one interrogation position complementary to a corresponding nucleotide in the reference sequence, (2) a second probe set comprising a corresponding probe for each probe in first probe set, the corresponding probe in the second probe set being identical to a sequence comprising the corresponding probe from the first probe set or a subsequence of at least three nucleotides thereof that includes the at least one interrogation position, except that the at least one interrogation position is occupied by a different nucleotide in each of the two corresponding probes from the first and second probe sets; wherein the probes in the first probe set have at least three interrogation positions respectively corresponding to each of three contiguous nucleotides in the reference sequence; provided that the array does not contain a complete set of probes of a given length, wherein a complete set is all permutations of nucleotides A,C, G and T/U: and wherein the reference sequence is from a biotransformation gene, wherein said biotransformation gene encodes an enzyme that is a reductase, an oxidase, a hydrolase or a transferase.

2. An array of oligonucleotide probes immobilized on a solid support, the array comprising at least four sets of oligonucleotide probes, (1) a first probe set comprising a plurality of probes, each probe comprising a segment of at least three nucleotides exactly complementary to a subsequence of a reference sequence, the segment including at least one interrogation position complementary to a corresponding nucleotide in the reference sequence, (2) second, third and fourth probe sets, each comprising a corresponding probe for each probe in the first probe set, the probes in the second, third and fourth probe sets being identical to a sequence comprising the corresponding probe from the first probe set or a subsequence of at least three nucleotides thereof that includes the at least one interrogation position, except that the at least one interrogation position is occupied by a different nucleotide in each of the four corresponding probes from the four probe sets;

provided the array lacks a complete set of probes of a given length, wherein a complete set is all permutations of nucleotides A, C, G and T/U; and wherein the reference sequence is from a biotransformation gene, wherein said biotransformation gene encodes an enzyme that is a reductase, an oxidase, a hydrolase or a transferase.

3. The array of claim 1 wherein the reference sequence is from a biotransformation gene encoding an enzyme selected from the group consisting of a cytochrome P450, N-acetyl transferase II, glucose 6-phosphate dehydrogenase, pseudocholinesterase, catechol-O-methyl transferase, and dihydropyridine dehydrogenase.

4. The array of claim 2, wherein the reference sequence is from a biotransformation gene encoding an enzyme selected from the group consisting of a cytochrome P450, N-acetyl transferase II, glucose 6-phosphate dehydrogenase, pseudocholinesterase, catechol-O-methyl transferase, and dihydropyridine dehydrogenase.

5. The array of claim 4, wherein the enzyme is P450 2D6 or P450.

6. The array of claim 2, wherein the reference sequence includes a site of a mutation and a site of a silent polymorphism.

7. The array of claim 6, wherein the silent polymorphism is in an intron or flanking region of a gene.

8. The array of claim 2, wherein the first probe set has at least 3 interrogation positions respectively corresponding to each of 3 contiguous nucleotides in the reference sequence.

9. The array of claim 2, wherein the array has between 100 and 100,000 probes.

10. The array of claim 2, wherein the probes are linked to the support via a spacer.

11. The array of claim 2, wherein the segment in each probe of the first probe set that is exactly complementary to the subsequence of the reference sequence is 9-21 nucleotides.

12. A method of comparing a target nucleic acid with a reference sequence comprising a predetermined sequence of nucleotides, the method comprising:
(a) hybridizing a sample comprising the target nucleic acid to an array of oligonucleotide probes immobilized on a solid support, the array comprising:
(1) a first probe set comprising a plurality of probes, each probe comprising a segment of at least three nucleotides exactly complementary to a subsequence of the reference sequence, the segment including at least one interrogation position complementary to a corresponding nucleotide in the reference sequence, wherein the reference sequence is from a biotransformation gene, wherein said biotransformation gene encodes an enzyme that is a reductase, an oxidase, a hydrolase or a transferase;
(2) a second probe set comprising a corresponding probe for each probe in the first probe set, the corresponding probe in the second probe set being identical to a sequence comprising the corresponding probe from the first probe set or a subsequence of at least three nucleotides thereof that includes the at least one interrogation position, except that the at least one interrogation position is occupied by a different nucleotide in each of the two corresponding probes from the first and second probe sets; wherein, the probes in the first probe set have at least three interrogation positions respectively corresponding to each of at least three nucleotides in the reference sequence, and
(b) determining which probes, relative to one another, in the first and second probe sets specifically bind to the target nucleic acid, the relative specific binding of corresponding probes in the first and second probe sets indicating whether a nucleotide in the target sequence is the same or different from the corresponding nucleotide in the reference sequence.

13. The method of claim 12, wherein the determining step comprises:
(1) comparing the relative specific binding of two corresponding probes from the first and second probe sets;
(2) assigning a nucleotide in the target sequence as the complement of the interrogation position of the probe having the greater specific binding; and
(3) repeating (1) and (2) until each nucleotide of interest in the target sequence has been assigned.

14. The method of claim 12, wherein the array further comprises third and fourth probe sets, each comprising a corresponding probe for each probe in the first probe set, the probes in the second, third and fourth probe sets being identical to a sequence comprising the corresponding probe from the first probe set or a subsequence of at least three nucleotides thereof that includes the at least one interrogation position, except that the at least one interrogation position is occupied by a different nucleotide in each of the four corresponding probes from the four probe sets;
and the determining step comprises determining which probes, relative to one another, in the first, second, third and fourth probe sets specifically bind to the target nucleic acid, the relative specific binding of corresponding probes in the first, second, third and fourth probe sets indicating whether a nucleotide in the target sequence is the same or different from the corresponding nucleotide in the reference sequence.

15. The method of claim 14, wherein: the reference sequence includes a site of a mutation in the biotransformation gene and a silent polymorphism in or flanking the biotransformation gene; the target nucleic acid comprises one or more different alleles of the biotransformation gene; and the relative specific binding of probes having an interrogation position aligned with the silent polymorphism indicates the number of different alleles and the relative specific binding of probes having an interrogation position aligned with the mutation indicates whether the mutation is present in at least one of the alleles.

16. The method of claim 14, wherein the determining comprises:
(1) comparing the relative specific binding of four corresponding probes from the first, second, third and fourth probe sets;
(2) assigning a nucleotide in the target sequence as the complement of the interrogation position of the probe having the greatest specific binding; and
(3) repeating (1) and (2) until each nucleotide of interest in the target sequence has been assigned.

* * * * *